(12) United States Patent
Sugiyama et al.

(10) Patent No.: US 6,991,634 B2
(45) Date of Patent: Jan. 31, 2006

(54) CLIP DEVICE OF ENDOSCOPE

(75) Inventors: Akira Sugiyama, Kanagawa (JP); Ichiro Ninomiya, Saitama (JP); Masahiro Takano, Tokyo (JP); Keiji Kunii, Tokyo (JP)

(73) Assignee: PENTAX Corporation, Tokyo (JP)

( * ) Notice: Subject to any disclaimer, the term of this patent is extended or adjusted under 35 U.S.C. 154(b) by 554 days.

(21) Appl. No.: 10/151,105

(22) Filed: May 21, 2002

(65) Prior Publication Data

US 2002/0177861 A1 Nov. 28, 2002

(30) Foreign Application Priority Data

| May 23, 2001 | (JP) | ............................ P2001-153658 |
| May 24, 2001 | (JP) | ............................ P2001-154804 |
| Jun. 13, 2001 | (JP) | ............................ P2001-177831 |
| Jun. 19, 2001 | (JP) | ............................ P2001-184360 |
| Aug. 17, 2001 | (JP) | ............................ P2001-247927 |
| Aug. 21, 2001 | (JP) | ............................ P2001-249834 |
| Nov. 9, 2001 | (JP) | ............................ P2001-343985 |
| Nov. 13, 2001 | (JP) | ............................ P2001-346965 |
| Nov. 15, 2001 | (JP) | ............................ P2001-349642 |
| Nov. 19, 2001 | (JP) | ............................ P2001-353218 |

(51) Int. Cl.
*A61B 17/10* (2006.01)

(52) U.S. Cl. ........................ 606/142; 606/151; 606/157
(58) Field of Classification Search ................ 606/151, 606/157, 158, 221, 142, 200; 600/104; 24/535–537
See application file for complete search history.

(56) References Cited

U.S. PATENT DOCUMENTS

| 3,958,576 | A | * | 5/1976 | Komiya ...................... 606/142 |
| 5,015,249 | A | * | 5/1991 | Nakao et al. ................ 606/142 |
| 5,520,701 | A | * | 5/1996 | Lerch .......................... 606/142 |
| 5,634,932 | A | * | 6/1997 | Schmidt ...................... 606/157 |
| 5,766,184 | A | | 6/1998 | Matsuno et al. |
| 5,766,189 | A | | 6/1998 | Matsuno |
| 5,993,474 | A | | 11/1999 | Ouchi |
| 6,090,129 | A | | 7/2000 | Ouchi |
| 6,267,776 | B1 | * | 7/2001 | O'Connell ................... 606/200 |

FOREIGN PATENT DOCUMENTS

| JP | 53-11589 | 3/1978 |
| JP | 62170010 | 10/1987 |
| JP | 2-6011 | 1/1990 |
| JP | 7-1905 | 1/1995 |
| JP | 8-17778 | 2/1996 |
| JP | 8-126648 | 5/1996 |
| JP | 9-289989 | 11/1997 |
| JP | 335631 | 12/2000 |

* cited by examiner

*Primary Examiner*—Julian W. Woo
(74) *Attorney, Agent, or Firm*—Greenblum & Bernstein, P.L.C.

(57) ABSTRACT

A forceps of endoscope comprises a clip that is provided with at least three arms and a base end portion. The arms are connected to the base end portion. Each of the arms has an open-close deforming portion located close to the base end portion. A core member is provided inside the clip to be in contact with an inner surface of the open-close deforming portion at least when the arms are open. A clip open-close ring is operated by remote control performed from the base end of the sheath. The clip open-close member is engaged with the open-close deforming portion to open and close the arms with a substantially equivalent angular interval and so as to prevent each of the arms from crossing each other.

58 Claims, 72 Drawing Sheets

CLIP DEVICE OF ENDOSCOPE

BACKGROUND OF THE INVENTION

1. Field of the Invention

The present invention relates to a clip device of an endoscope, which is inserted through a treatment tool insert channel of an endoscope and is used for performing tasks such as stopping bleeding, ligation, and a marking in a human body.

2. Description of the Related Art

Conventionally, a clip of a clip device is constructed in such a manner that a pair of arms is connected to each other at a base end thereof and is opened and closed by a clip open-close ring, which is fit and engaged with the outside surfaces of the arms. Namely, the clip open-close ring is moved relative to the clip to open and close the arms by deforming a portion of the arms near to the base end and it maintains the closed condition of the arms by engaging the base end. The clip device is inserted into an inlet opening of a treatment tool insert channel, and positioned at a portion close to another opening thereof.

The clip is formed of a metal plate strip, such as stainless steel, having elasticity. Namely, the metal plate strip is bent in an α-shape, and the extending portions are the arms.

However, the breadth of a boundary portion between the base end and each of the arms is less than a half the other portion, and therefore, the strength of the boundary portion is weak and it may be accidentally damaged or deformed, causing the clip to become useless.

SUMMARY OF THE INVENTION

Therefore, an object of the present invention is to provide a clip device, in which a clip has sufficient strength so as not to be accidentally damaged during use, and which can be stably opened and closed.

According to the present invention, there is provided a clip device of an endoscope, comprising a clip, a core member, and an open-close member.

The clip is provided with at least three arms and a base end portion to which the arms are connected. Each of the arms has an open-close deforming portion located near the base end portion, the clip being inserted in a sheath, in a state in which the arms are closed, and positioned at a distal end of the sheath. The core member is provided inside the clip to be in contact with an inner surface of the open-close deforming portion at least when the arms are open. The open-close member is operated by remote control performed from the base end of the sheath, which is opposite to the distal end. The open-close member is engaged with the open-close deforming portion to open and close the arms with a substantially equivalent angular interval and so as to prevent the arms from crossing each other.

Further, according to the present invention, there is provided a clip device of an endoscope, comprising a clip and an open-close member.

The clip is provided with a pair of arms and a base end portion to which the arms are connected. Each of the arms has an open-close deforming portion located close to the base end portion. The clip is obtained by bending a single plate member without crossing at any portion in such a manner that a boundary portion, between the base end portion and the arms, is formed into a constriction. The clip is inserted in a sheath, in a state in which the arms are closed, and positioned at a distal end of the sheath. The open-close member is operated by remote control performed from the base end of the sheath, which is opposite to the distal end. The open-close member is engaged with the open-close deforming portion to open and close the arms with a substantially equivalent angular interval and so as to prevent the arms from crossing each other.

BRIEF DESCRIPTION OF THE DRAWINGS

The objects and advantages of the present invention will be better understood from the following description, with reference to the accompanying drawings in which.

DESCRIPTION OF THE PREFERRED EMBODIMENTS

Figure 1:
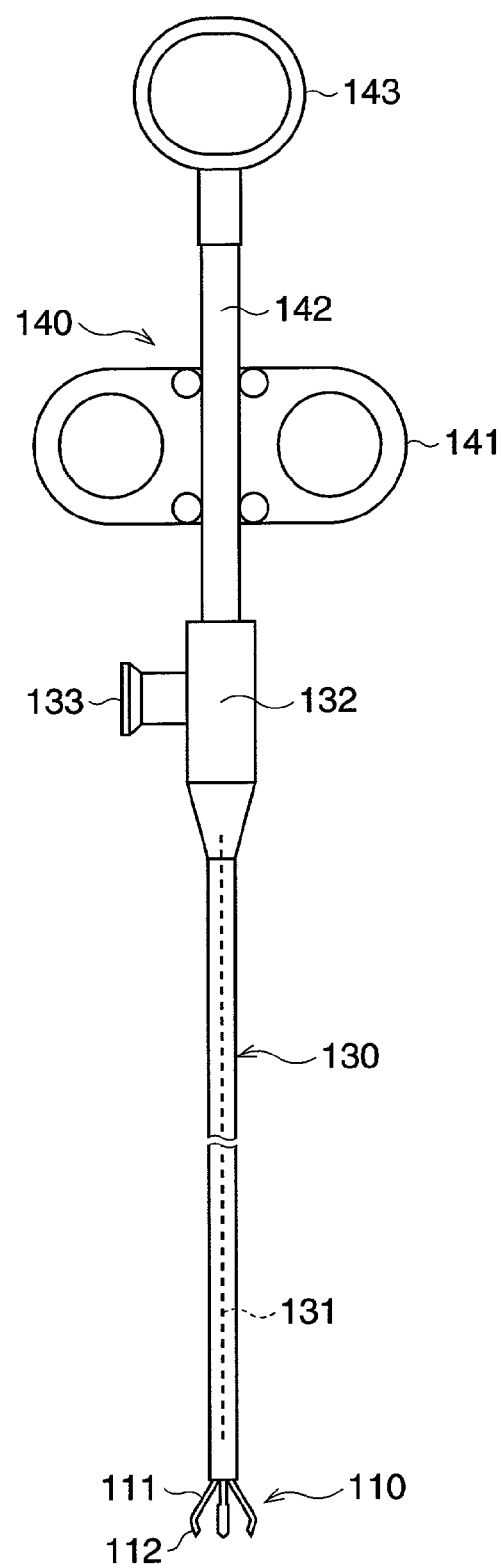
FIG. 1 is an external view showing a general construction of a clip device, to which a first embodiment of the present invention is applied.

The present invention will be described below with reference to the embodiments shown in the drawings.

FIG. 1 shows a general construction of a clip device, in which a clip 110 is disposed at a distal end of a flexible outer sheath (i.e., cover tube) 130 which is formed from tetrafluorinated ethylene resin, super-elastic alloy, and so on.

A base end portion (not shown) of the clip 110 is housed in the distal end of the outer sheath 130, and arms 111, which are open in the drawing, and claw portions 112, which are bent inwardly at the tips of the arms 111, are exposed from the distal end of the outer sheath 130.

An operating unit 140 is connected to the outer sheath 130. In the operating unit 140, a slider 141 is connected to a tip of an operating wire 131 which will be described later, and is slidably provided to a shaft 142 which has a finger-ring 143 at an end thereof.

A base end cylinder 132 of the outer sheath 130 is slidably connected to the shaft 142, and is moved relative to the slider 141. Namely, the slider 141, the shaft 142, and the outer sheath 130 are independently moved from each other along the longitudinal axis of the outer sheath 130. A water supply tube 133 is projected from the base end cylinder 132 so that water can be supplied into the outer sheath 130 through the water supply tube 133.

Figure 2:
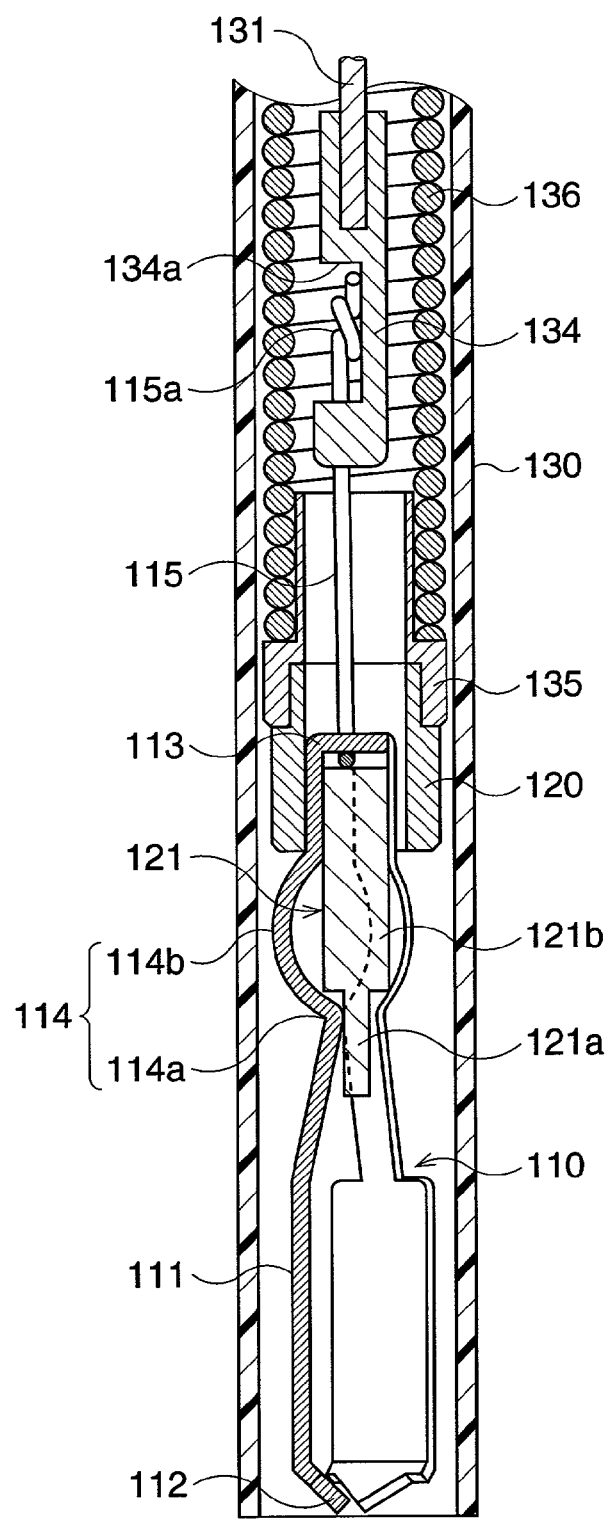
FIG. 2 is a longitudinal sectional view of a distal end of the clip device of the first embodiment.
Figure 3:
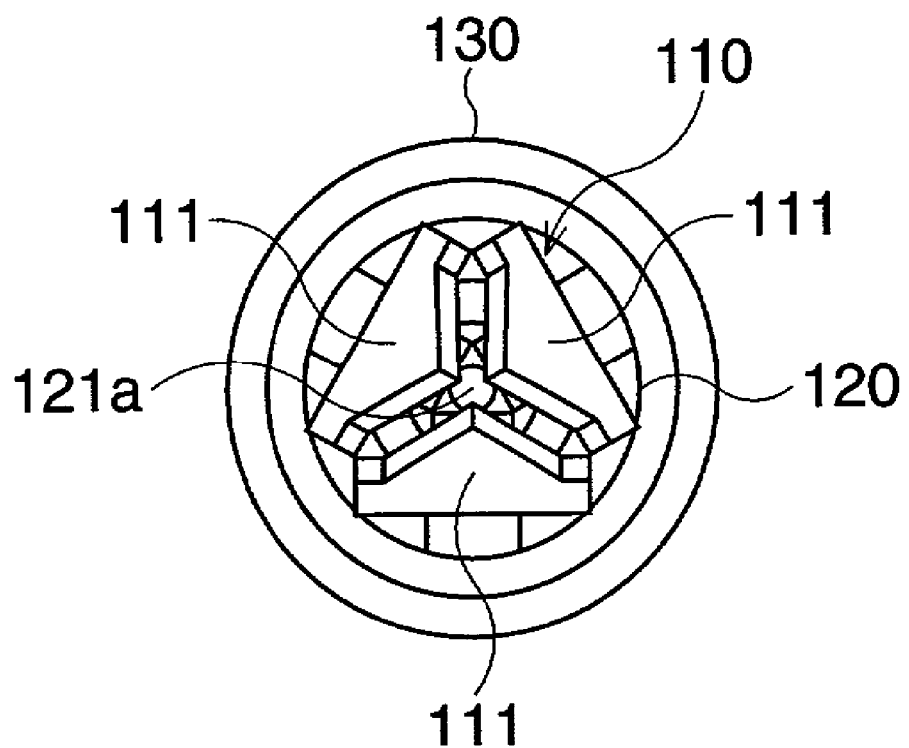
FIG. 3 is a front view of the distal end of the clip device.

FIG. 2 is a longitudinal sectional view in which the distal end of the outer sheath 130 is enlarged, and FIG. 3 is a front view of the end portion. Note that, in these drawings, the clip 110 which is closed, is almost completely housed in the outer sheath 130.

The clip 110 is integrally formed from stainless steel for a spring, for example. Namely, the clip 110 is obtained by bending the stainless steel plate, and the three arms 111 connected to the base end portion 113 are provided at equivalent angular intervals (i.e., approximately 120 degrees), and open and close without crossing each other.

Each of the arms 111 has an open-close deforming portion 114 located close to the base end portion 113. The open-close deforming portion 114 has a constriction 114a and a bulge portion 114b formed between the constriction 114a and the base end portion 113. The bulge portion 114b is bulged outward and formed in an arc shape in section. The arms 111 are open and closed by deforming the open-close deforming portion 114. Note that the shape of the bulge portion 114b may be other than the arc shape, if the arms 111 can be open and closed.

The operating wire 131 is disposed in the axial position of the outer sheath 130. The operating wire 131 is operated by the slider 141 to move along the axis of the outer sheath 130. A clip connecting hook 134 is attached to the tip of the operating wire 131. A clip connecting string 115, which is connected to the base end portion 113 of the clip 110, can be engaged with and disengaged from the clip connecting hook 134. The clip connecting string 115 is a strand wire or a normal single wire made of stainless steel, for example.

The rear end half of the clip connecting hook 134 is connected to the operating wire 131 with solder and so on, and the clip connecting string 115 can be engaged with and disengaged from a recess 134a formed on a side surface of the front end half of the clip connecting hook 134. The clip connecting string 115 is tied in a knot 115a, which is engagable with the recess 134a.

A clip open-close ring 120 is mounted in the outer sheath 130, so that the bulge portion 114b of the clip 110 is pressed from the outside to deform the bulge portion 114b. The clip open-close ring 120 is movable along the axial direction of the outer sheath 130 relative to the clip 110.

A core member 121, which is made of metal, for example, is provided inside the arms 111 of the clip 110. The core member 121 is extended from the open-close deforming portion 114 to the base end portion 113. The core member 121 has a small diameter portion 121a positioned inside the constriction 114a and a large diameter portion 121b positioned closer to the base end portion 113 in comparison with the small diameter portion 121a. Thus, the large diameter portion 121b cannot pass through the constriction 114a, to prevent the core member 121 from dropping off from the inside of the arms 111.

A base end portion of the clip open-close ring 120 is fit in a ring receiving cylinder 135, which is connected to a tip portion of an inner sheath 136. The inner sheath 136 is a coil pipe, which is tightly wound, and is connected to the shaft 142 of the operating unit 140 with solder, for example.

Figure 4:
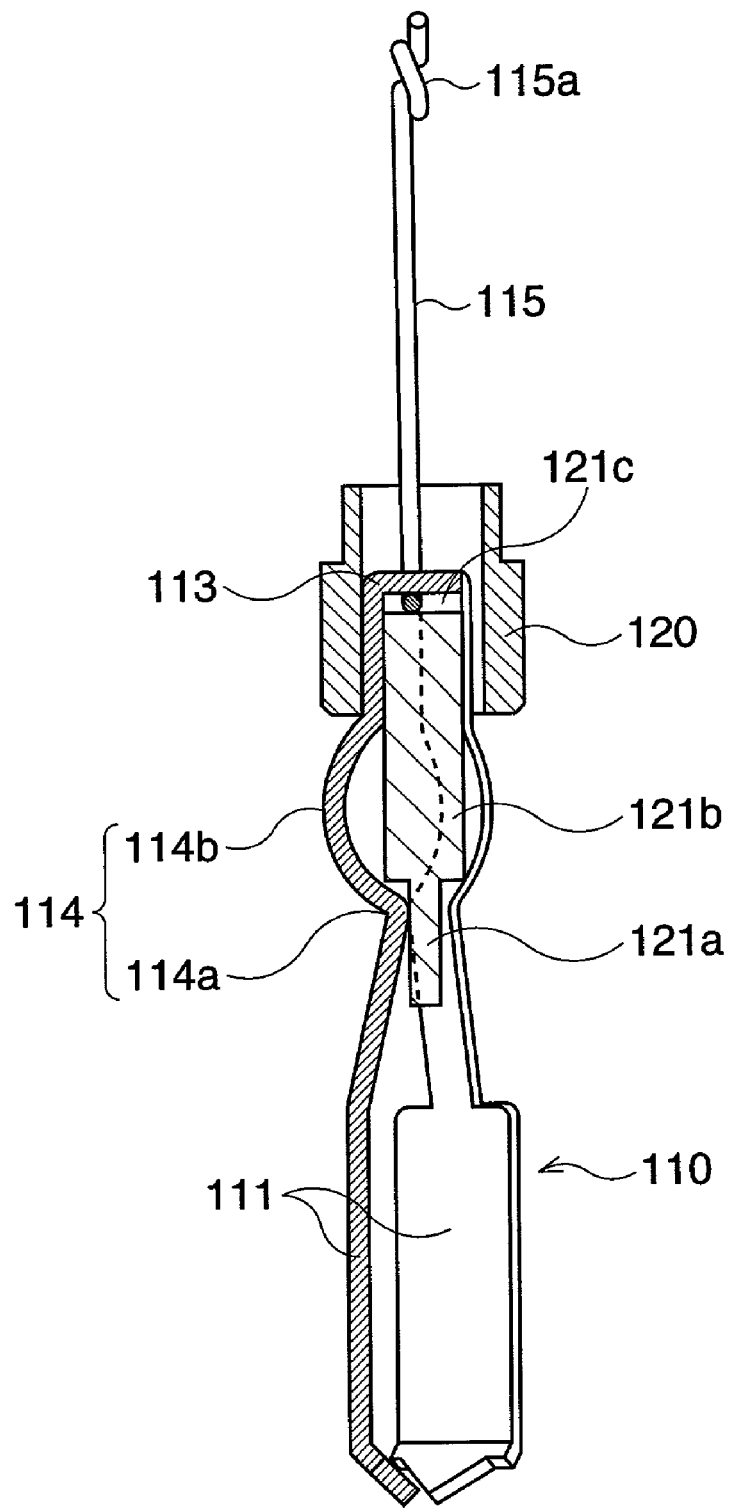
FIG. 4 is a longitudinal sectional view of a clip unit.
Figure 5:
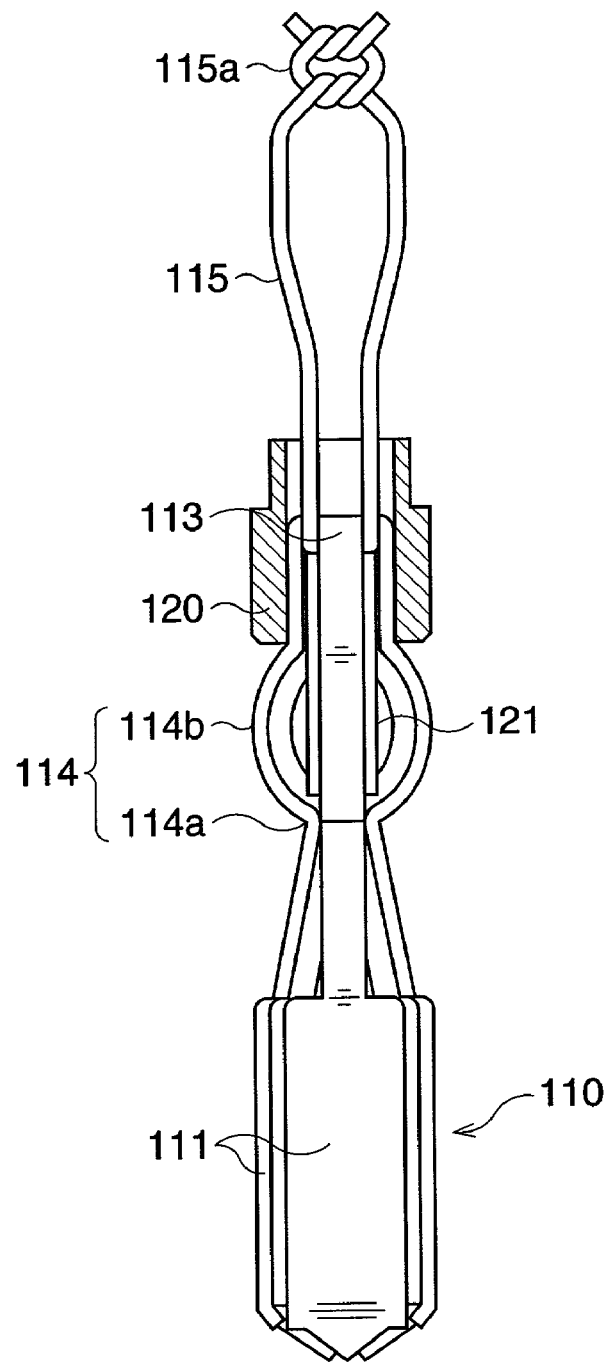
FIG. 5 is a partially sectional plan view of the clip unit.

Thus, as shown in FIGS. 4 and 5, the clip 110 forms a single unit containing the clip connecting string 115, the clip open-close ring 120, and the core member 121. The clip connecting string 115 is passed between the base end portion 113 of the clip 110 and a rear end surface 121c of the core member 121. The clip open-close ring 120 is fit on an outer surface of the base end portion 113 of the clip 110, and is fixed there with a frictional force.

Figure 6:
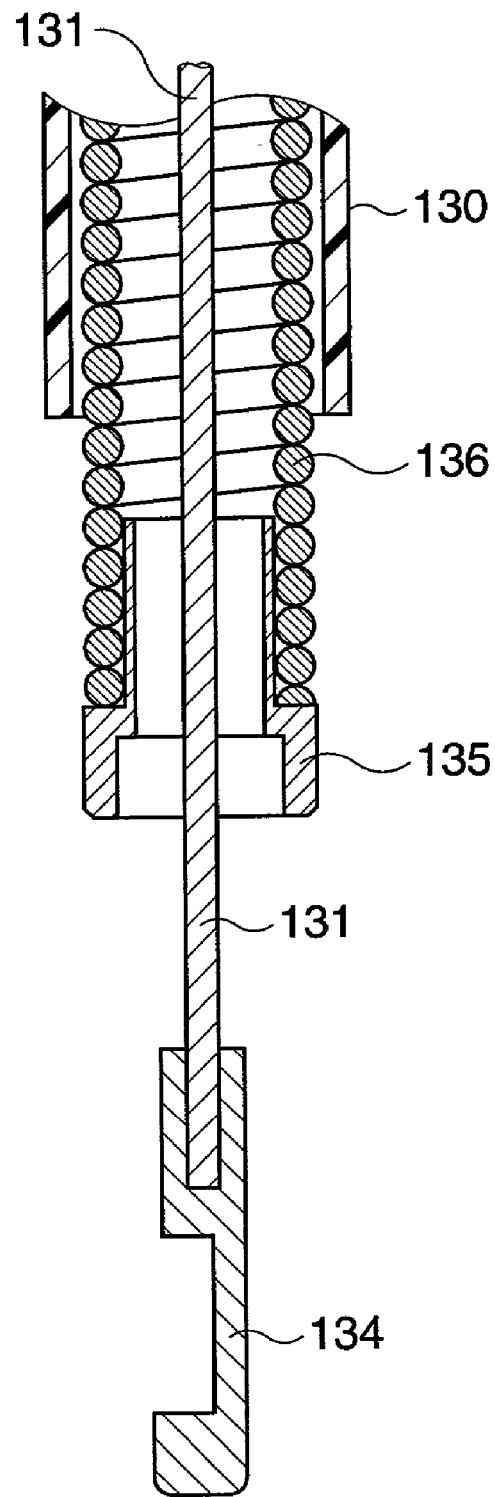
FIG. 6 is a longitudinal sectional view showing the distal end of the clip device when the clip unit is not attached to a clip connecting hook.
Figure 7:
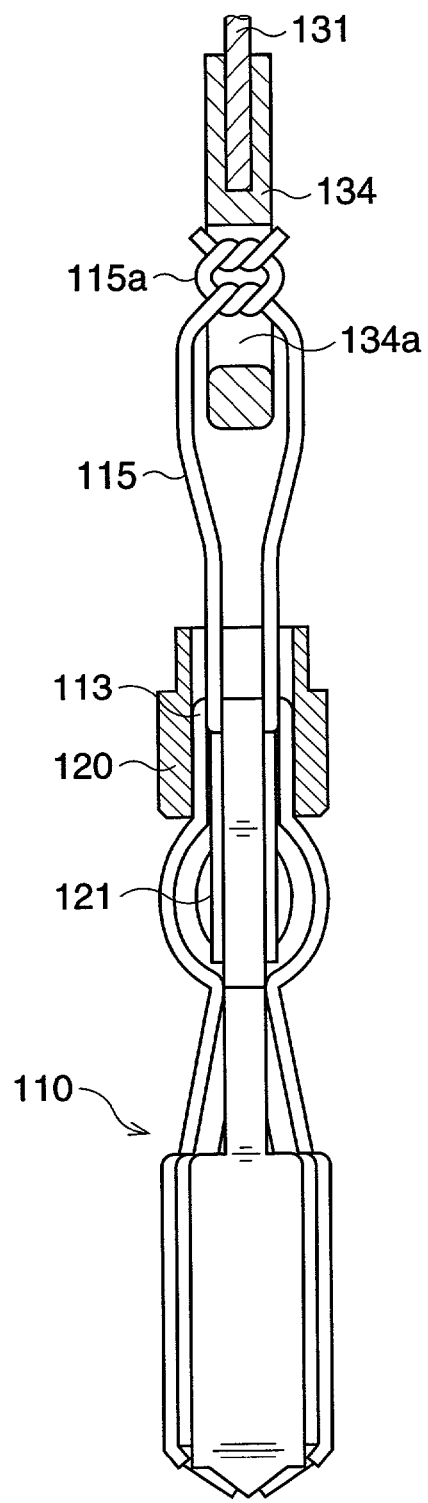
FIG. 7 is a partially sectional plan view of the clip unit which is attached to the clip connecting hook.
Figure 8:
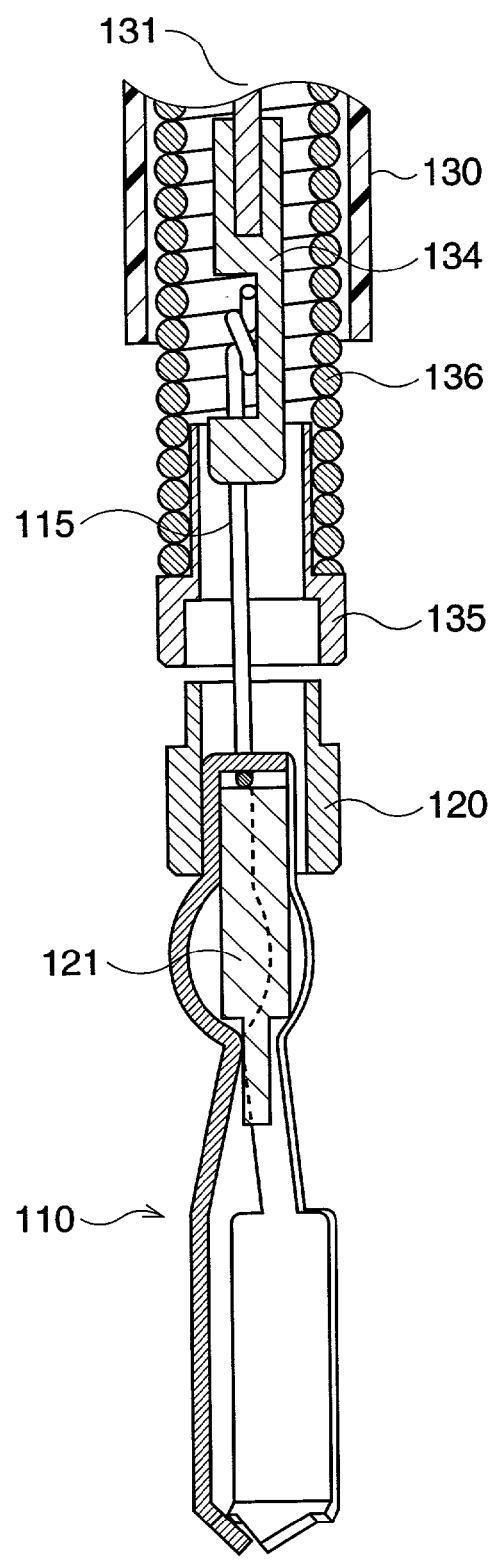
FIG. 8 is a longitudinal sectional view showing the distal end of the clip device, when the clip unit is attached to the clip connecting hook and is pulled by an operating wire.

When in use, as shown in FIG. 6, the tip portion of the inner sheath 136 is projected from the distal end of the outer sheath 130, and the clip connecting hook 134 is projected from the tip portion of the inner sheath 136. Then, as shown in FIG. 7, the knot 115a of the clip connecting string 115 is engaged with the recess 134a of the clip connecting hook 134. Note that the arms 111 are closed due to the clip open-close ring 120 being engaged with the base end portion 113. Then, maintaining the state in which the clip connecting string 115 is engaged with the clip connecting hook 134, as shown in FIG. 8, the operating wire 131 is pulled from the operating unit 140, so that the clip connecting hook 134 is retracted into the inner sheath 136.

As a result, as shown in FIG. 2, the clip open-close ring 120 is received by the ring receiving cylinder 135, so that the outer sheath 130 is moved forward relative to the clip 110, and the clip 110 is inserted and housed in the distal end of the outer sheath 130, in a state in which said arms are closed.

Keeping the state shown in FIG. 2, the outer sheath 130 is inserted into a treatment tool insert channel of an endoscope not shown. The knot 115a of the clip connecting string 115 is preferably formed larger than the gap between the inner sheath 136 and the clip connecting hook 134 so that the clip connecting string 115 is disengaged from the clip connecting hook 134 during the inserting operation.

Figure 9:
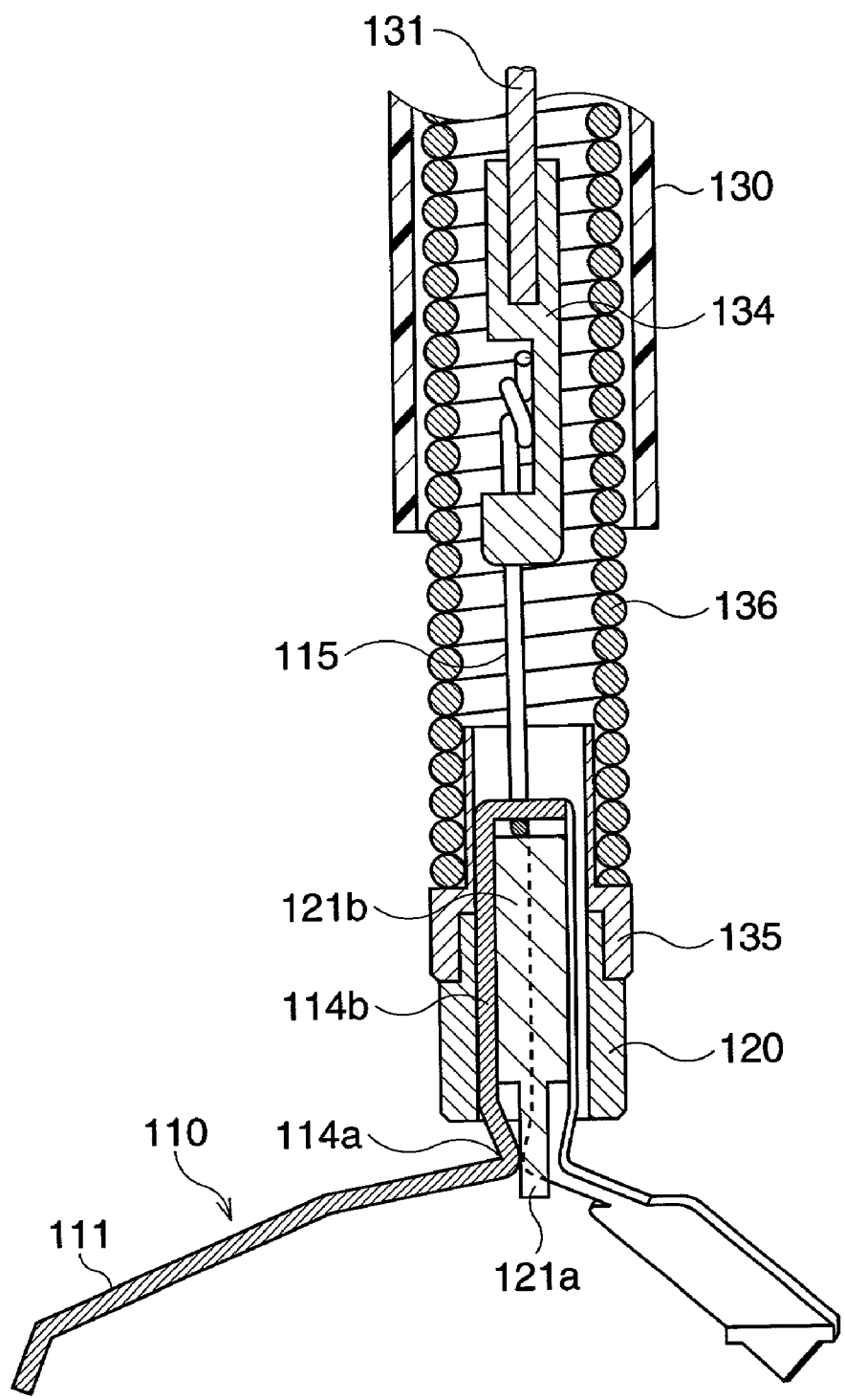
FIG. 9 is a longitudinal sectional view showing the distal end of the clip device when the clip is open.
Figure 10:
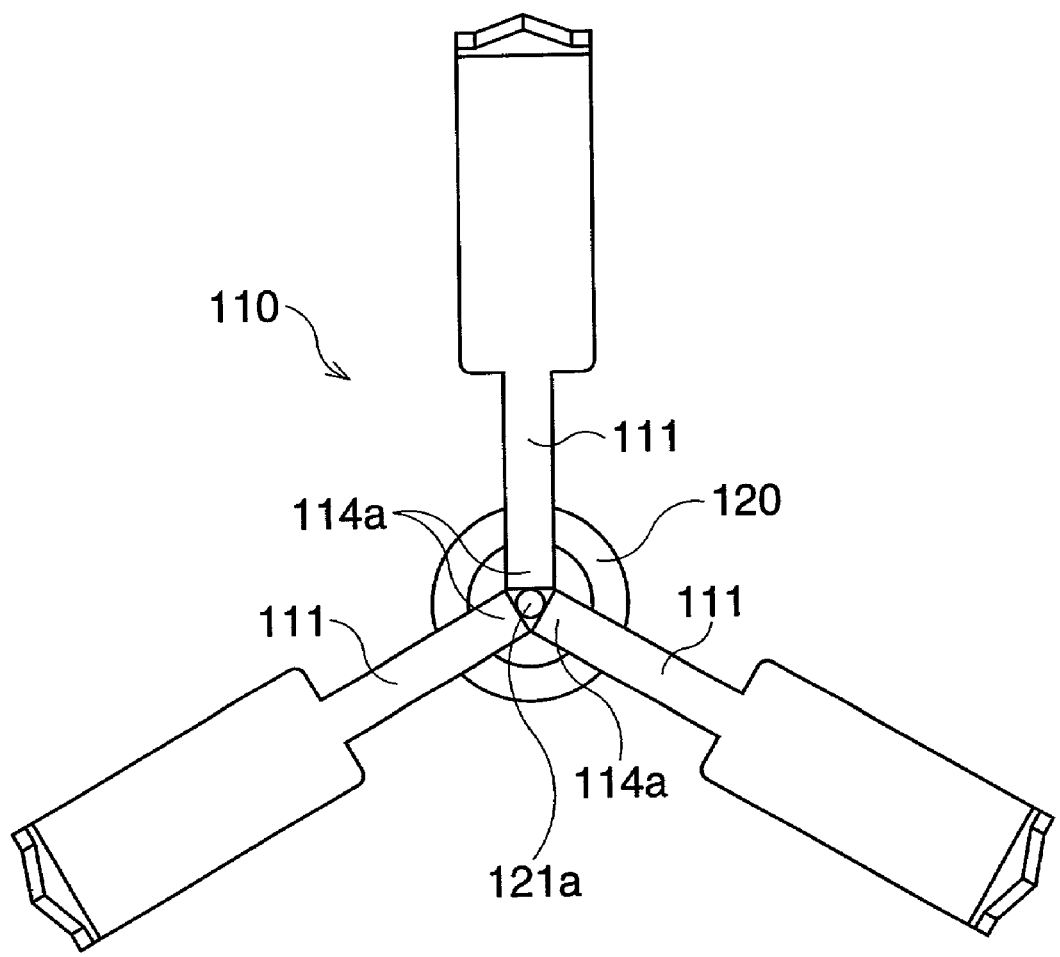
FIG. 10 is a front view of the distal end of the clip device when the clip is open.

When the distal end of the outer sheath 130 is led to the diseased part to be clipped, as shown in FIG. 9, the outer sheath 130 is moved rearward (upward in the drawing), and the operating wire 131 is then pulled. As a result, the bulge portion 114b of the clip 110 is pulled into the clip open-close ring 120, and is deformed, so that the arms 111 are open. In this state, although the constriction 114a of the clip 110 is pressed inward, since the constriction 114a is uniformly pressed onto the small diameter portion 121a of the core member 121 as shown in FIG. 10, the three arms 111 can open widely at approximately 120-degree intervals, while maintaining stability.

Figure 11:
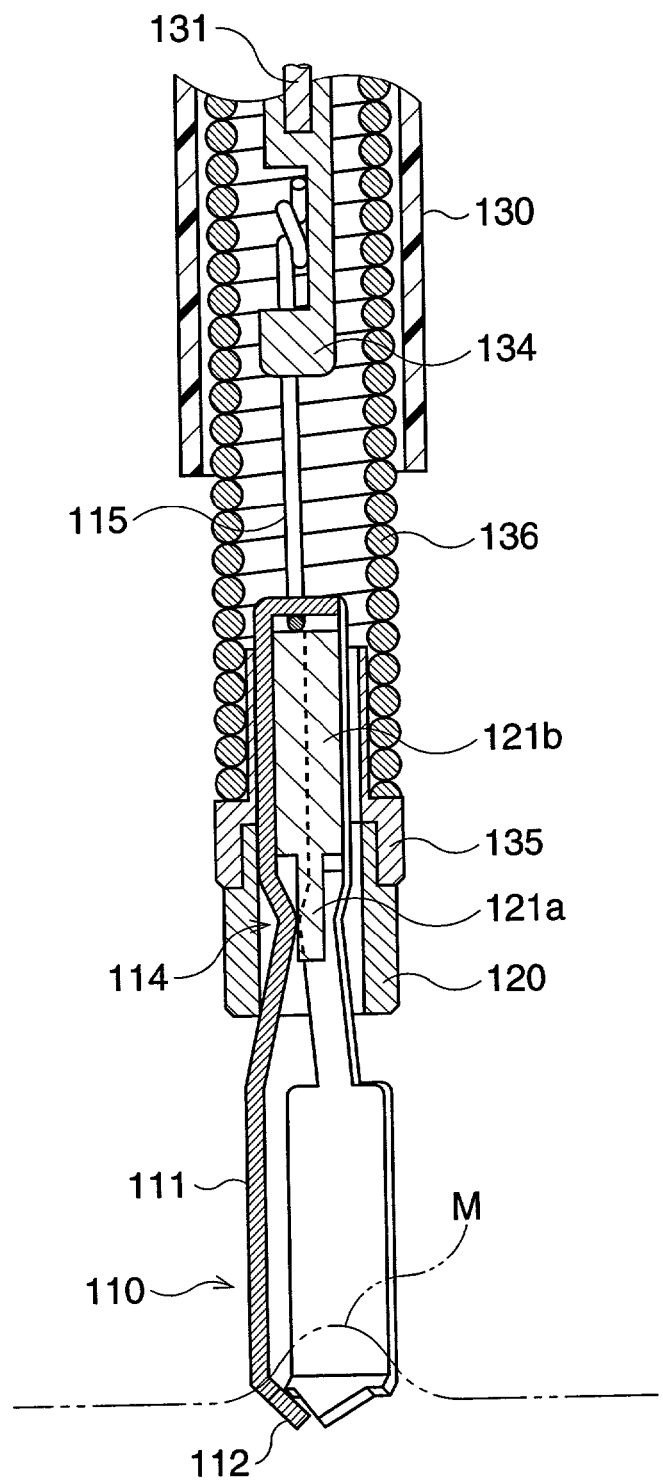
FIG. 11 is a longitudinal sectional view showing the distal end of the clip device, when the clip is closed.

Then, when the operating wire 131 is further pulled from the operating unit, as shown in FIG. 11, the opening parts of the arms 111 of the clip 110 are pulled into the clip open-close ring 120 and squeezed, so that the claw portions 112 formed at the tip portions of the arms 111 bite into a mucous membrane, enveloping the diseased portion M.

Figure 12:
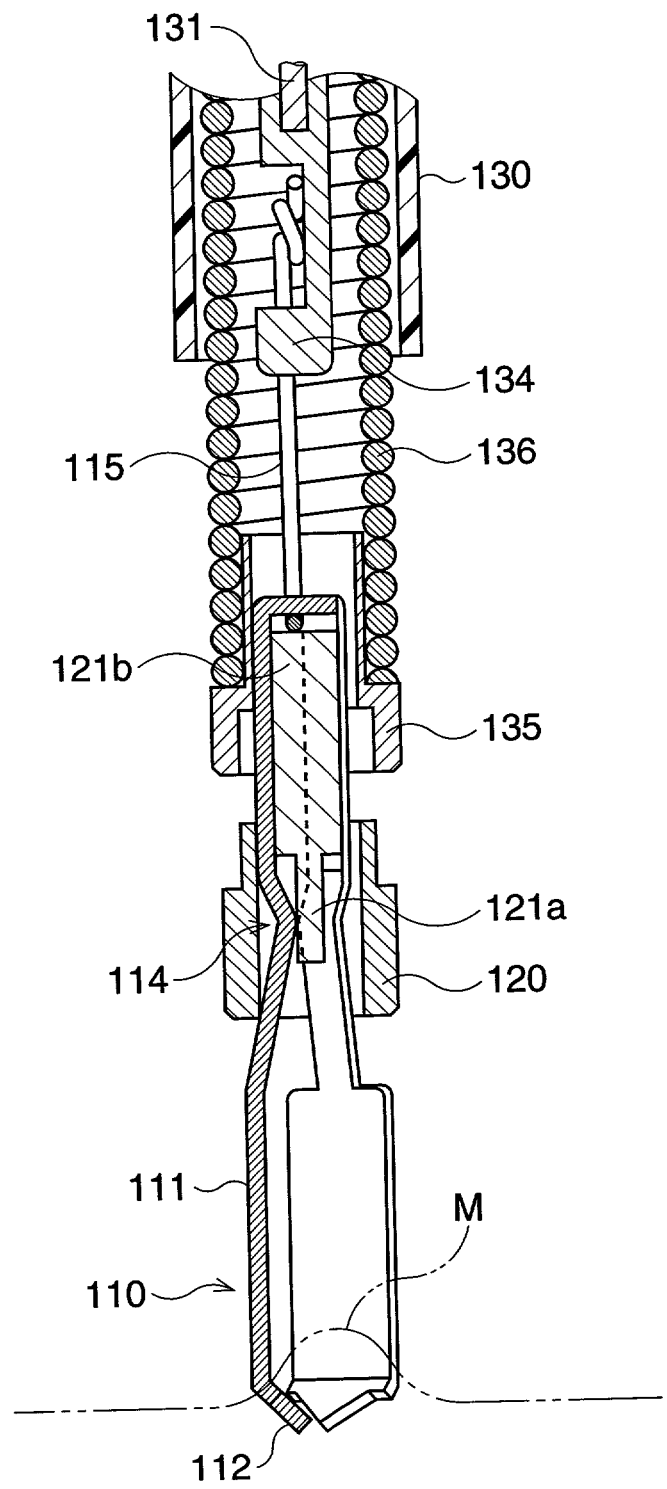
FIG. 12 is a longitudinal sectional view showing the distal end of the clip device, after the clipping operation shown in FIG. 11.
Figure 13:
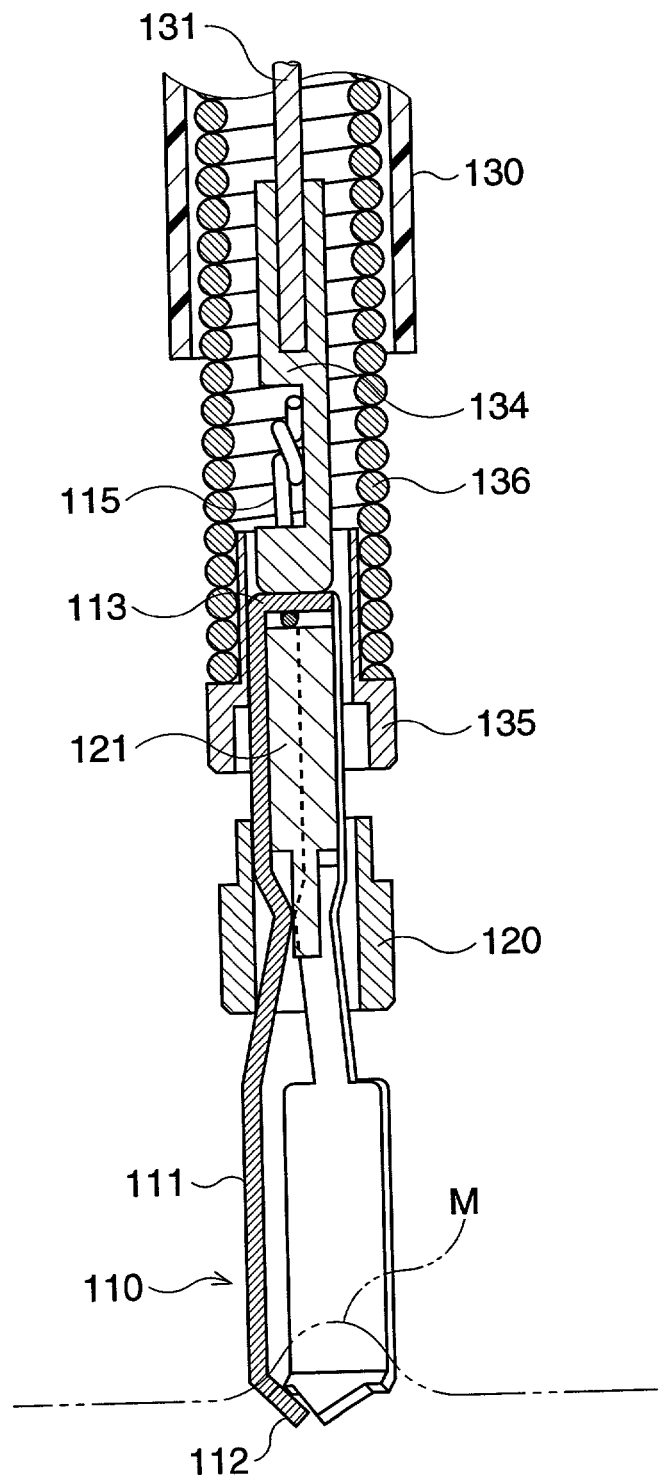
FIG. 13 is a longitudinal sectional view showing the distal end of the clip device, when a top surface of the clip is pressed by a clip connecting hook.

Therefore, as shown in FIG. 12, when the inner sheath 136 is slightly moved rearward (i.e., upward in the drawing), the ring receiving cylinder 135 is released from the clip open-close ring 120. At this time, as shown in FIG. 13, if the top surface of the clip connecting hook 134 is pressed onto the base end portion 113 of the clip 110, the ring receiving cylinder 135 is more easily released from the clip open-close ring 120.

Figure 14:
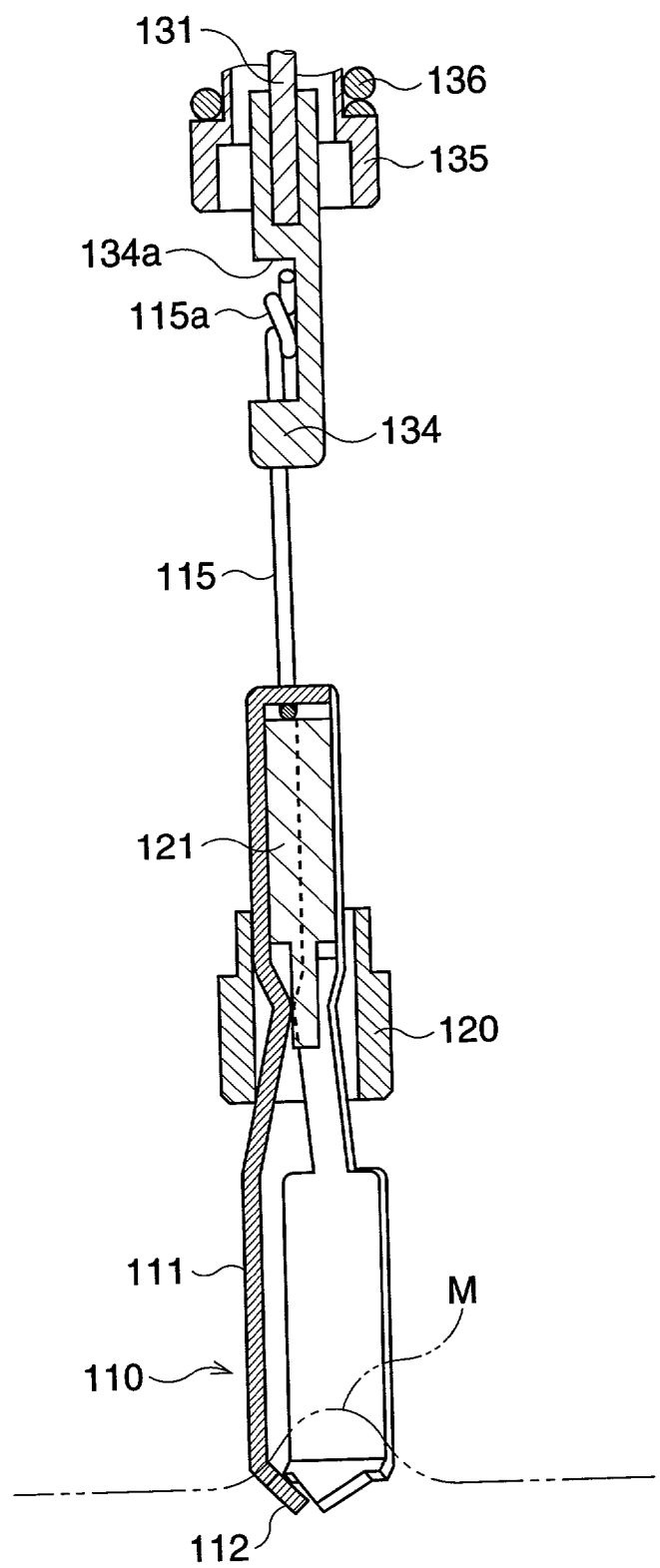
FIG. 14 is a longitudinal sectional view showing the distal end of the clip device, when the clip connecting hook is exposed from the sheath.

Then, as shown in FIG. 14, when the inner sheath 136 is moved rearward to project the clip connecting hook 134 forward, the recess 134a of the clip connecting hook 134 is exposed from the inner sheath 136. Accordingly, only by moving the clip connecting hook 134 properly, can the clip connecting hook 134 be disengaged from the clip connecting string 115. Thus, the clip 110, in which the arms 111 are kept in the closed condition by the clip open-close ring 120, is clamped on the diseased portion M.

As described above, in the first embodiment, the core member 121 is provided inside the clip 110 and is in contact with an inner surface of the open-close deforming portion 114 at least when the arms 111 are open, and the open-close ring 120 is operated by remote control performed from the base end of the outer sheath 130, which is opposite to the distal end. The open-close ring 120 is engaged with the open-close deforming portion 121 to open and close the arms 111 with a substantially equivalent angular interval and so as to prevent the arms 111 from crossing each other. Therefore, the arms 110 are stably opened and closed to perform tasks such as stopping bleeding, ligation, and marking in a human body.

Figure 15:
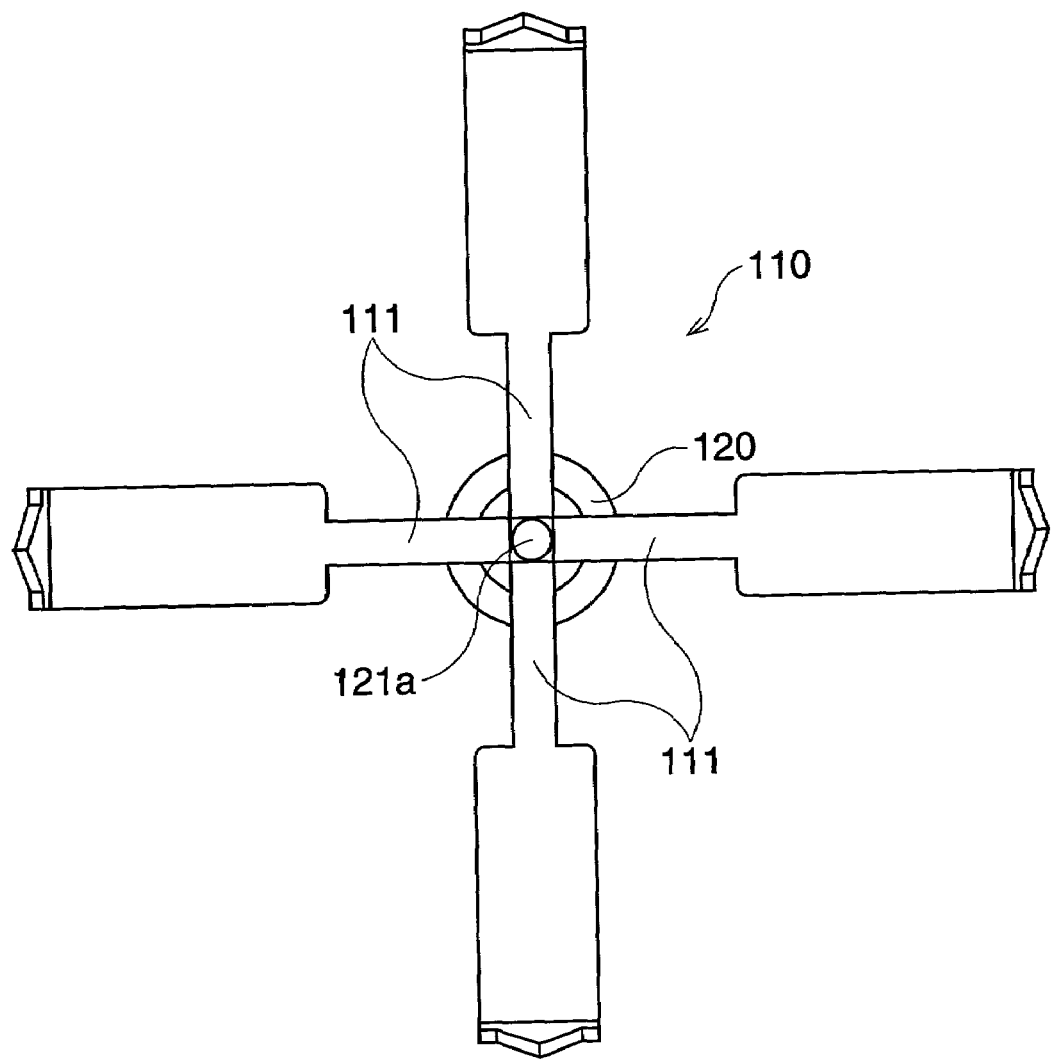
FIG. 15 is a front view of the distal end of the clip device when a clip having four arms is open.
Figure 16:
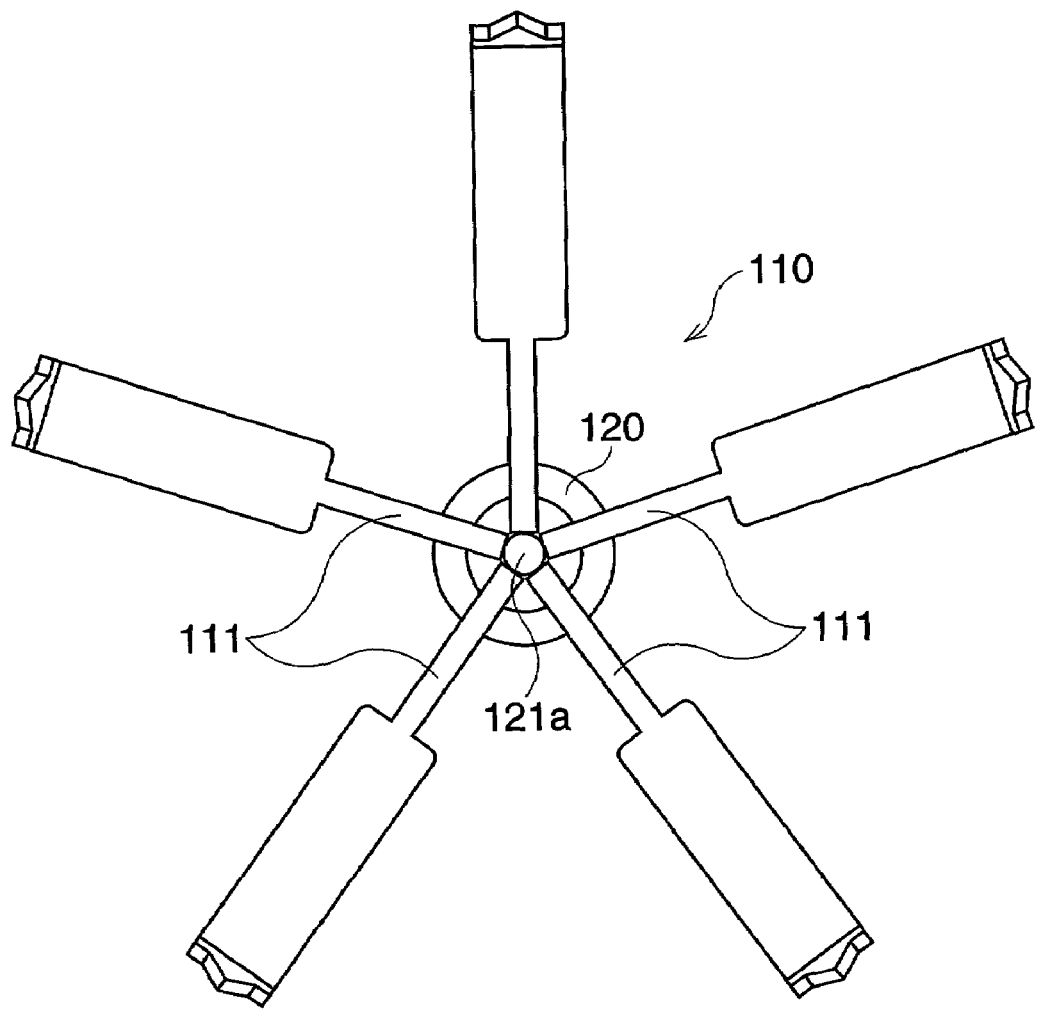
FIG. 16 is a front view of the distal end of the clip device when a clip having five arms is open.
Figure 17:
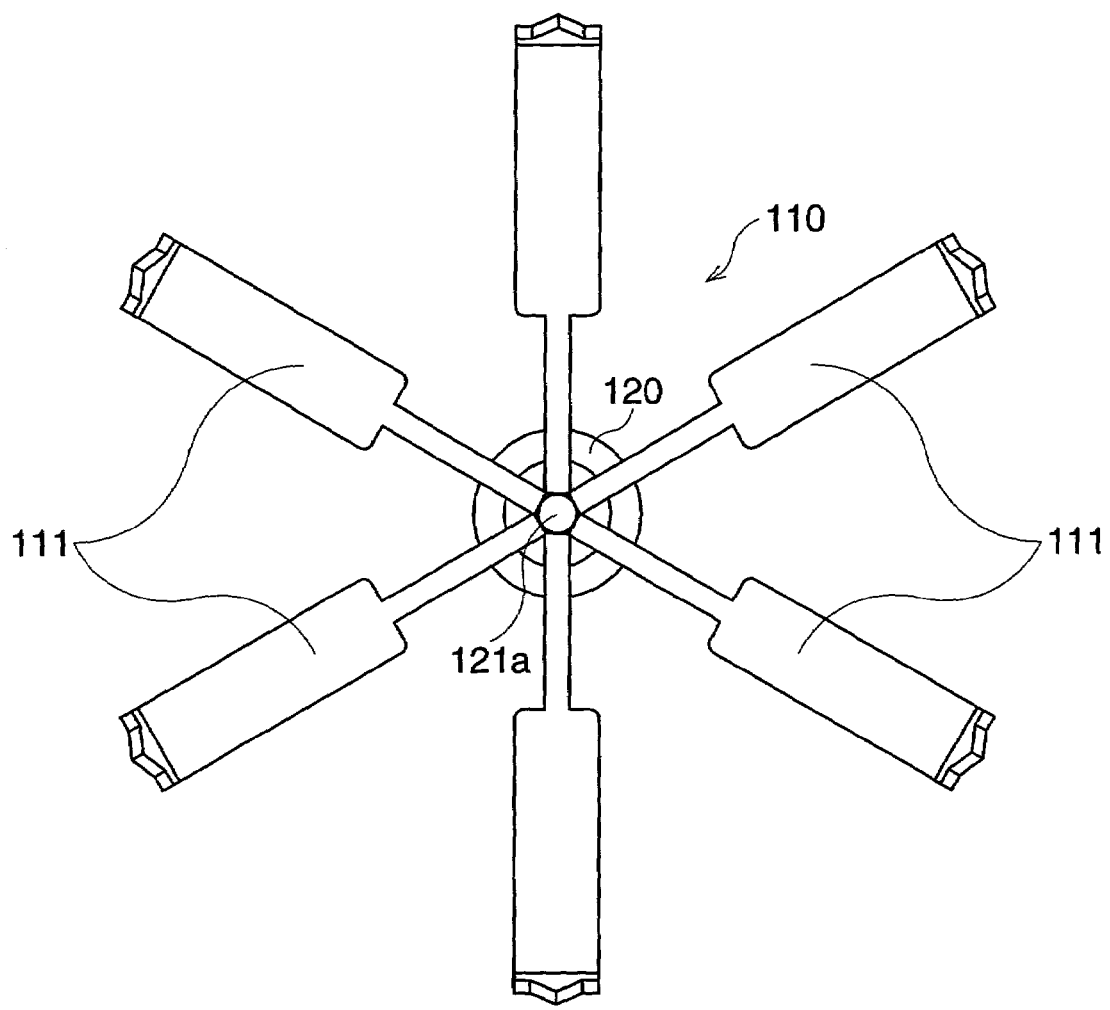
FIG. 17 is a front view of the distal end of the clip device when a clip having six arms is open.

Note that the number of arms 111 of the clip 110 is not restricted to three, there can be two or more as shown in FIGS. 15, 16, and 17.

Figure 18:
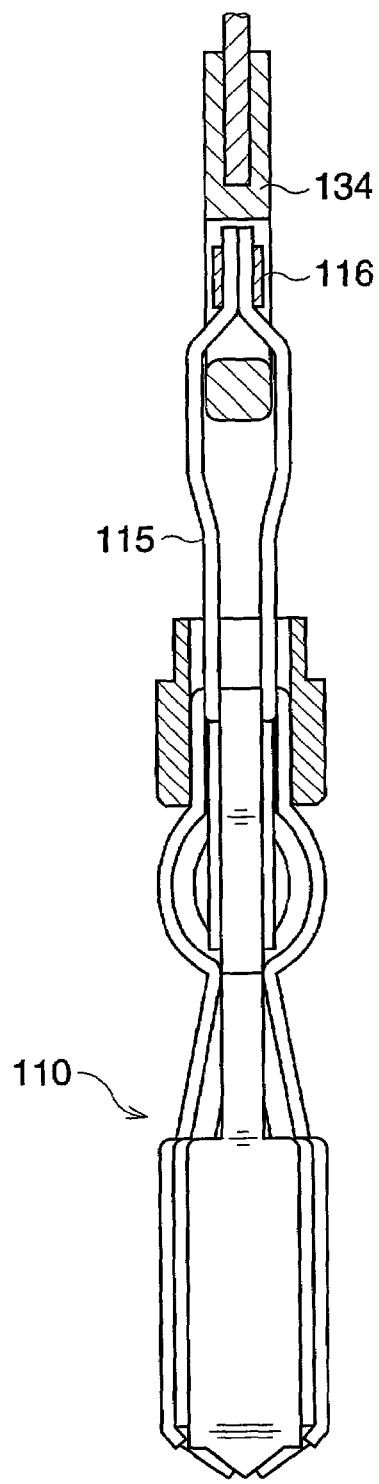
FIG. 18 is a partially sectional plan view showing a clip of a second embodiment.

FIG. 18 shows a second embodiment, in which both ends of the clip connecting string 115 are bundled in a pipe 116, for example, which adheres to the ends, to form a ring, instead of tying the ends as in the first embodiment. It is preferable that the outer diameter of the pipe 116 is greater than the gap between the inner sheath 136 and the clip connecting hook 134 to prevent the clip connecting string 115 from releasing from the clip connecting hook 134 during the inserting operation.

Figure 19:
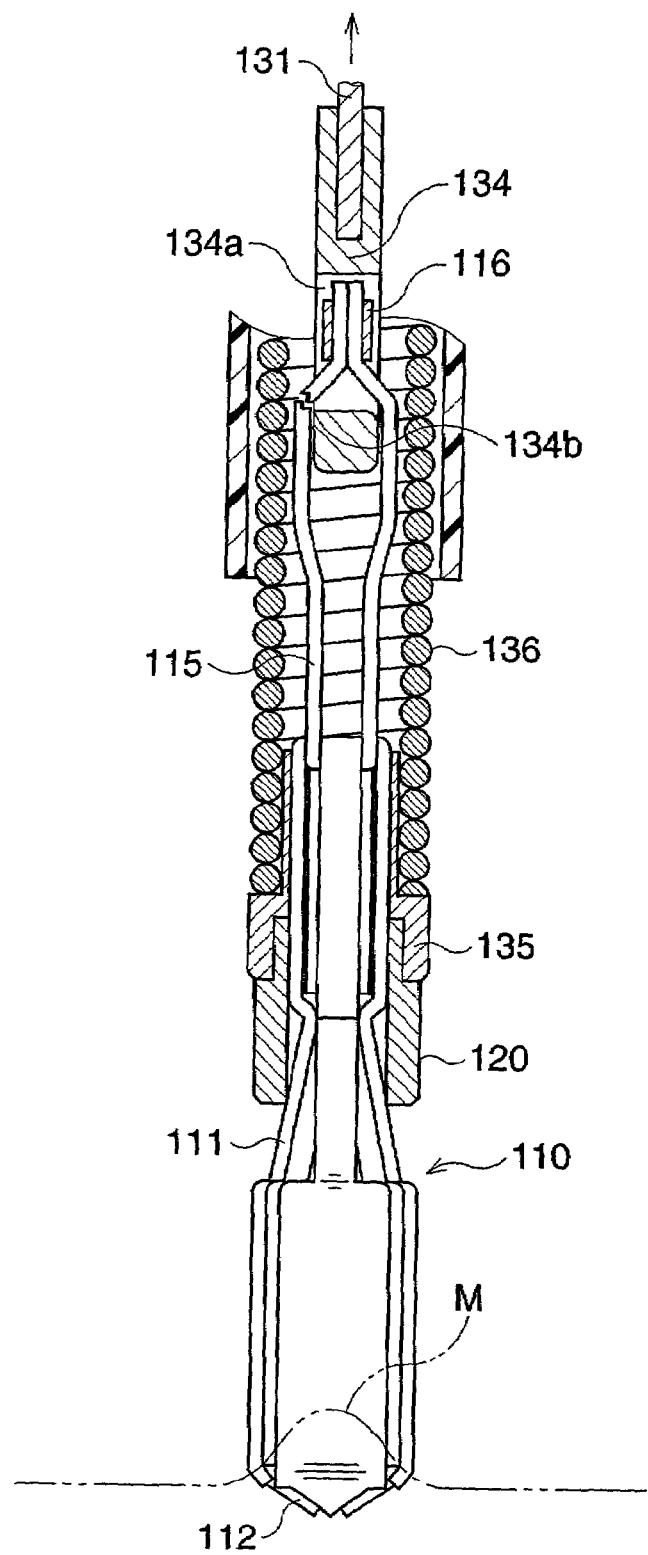
FIG. 19 is a partially sectional plan view showing a clip of a third embodiment.
Figure 20:
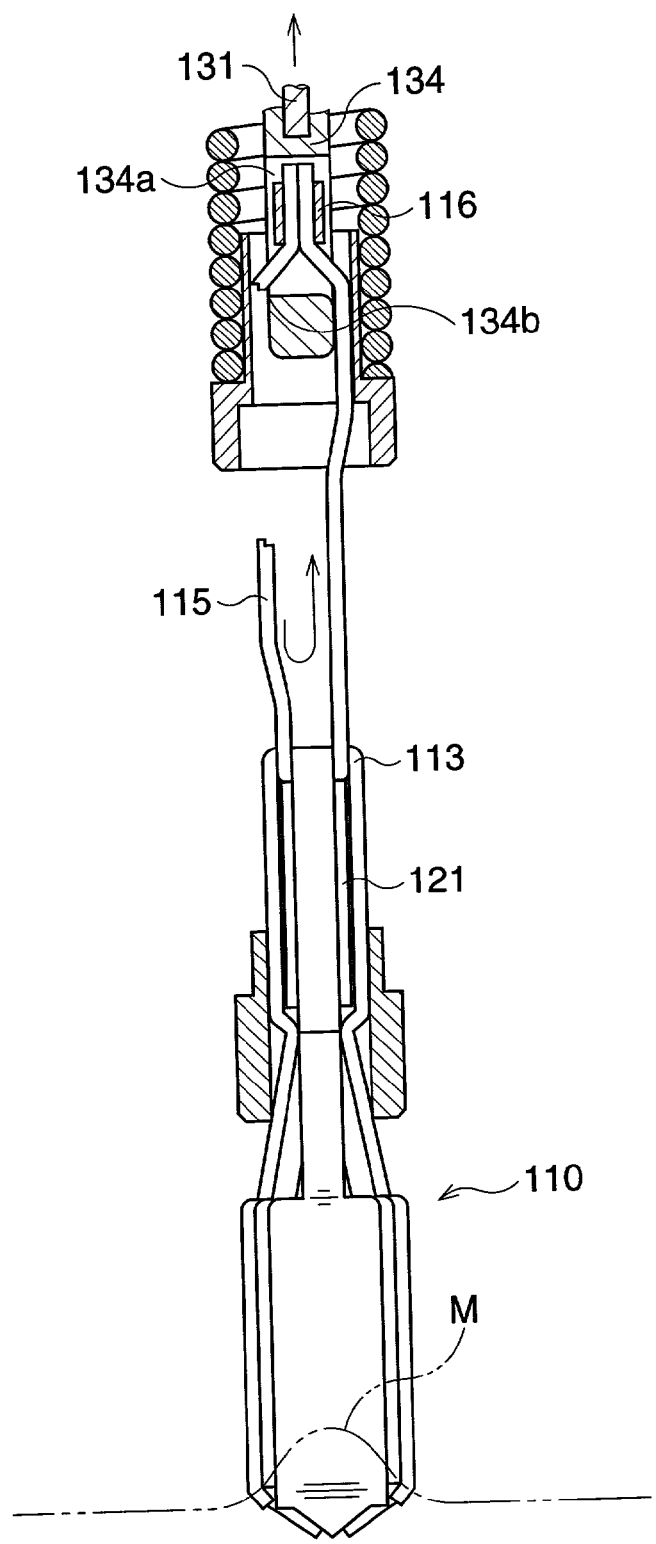
FIG. 20 is a partially sectional plan view showing a clip of the third embodiment, when a clip connecting string is released from the clip.

FIGS. 19 and 20 show a third embodiment, in which the clip connecting hook 134 has an acute angle corner 134b, which is firmly pressed onto the clip connecting string 115 to cut the string 115. Therefore, due to a series of operations in which the operating wire 131 is pulled toward the operating unit 140 step by step, the engagement of the clip connecting hook 134 and the clip connecting string 115 is released, at the last stage of the operation. Thus, the clip connecting string 115 comes off from the clip 110, as shown in FIG. 20, and is recovered with the clip connecting hook 134.

Figure 21:
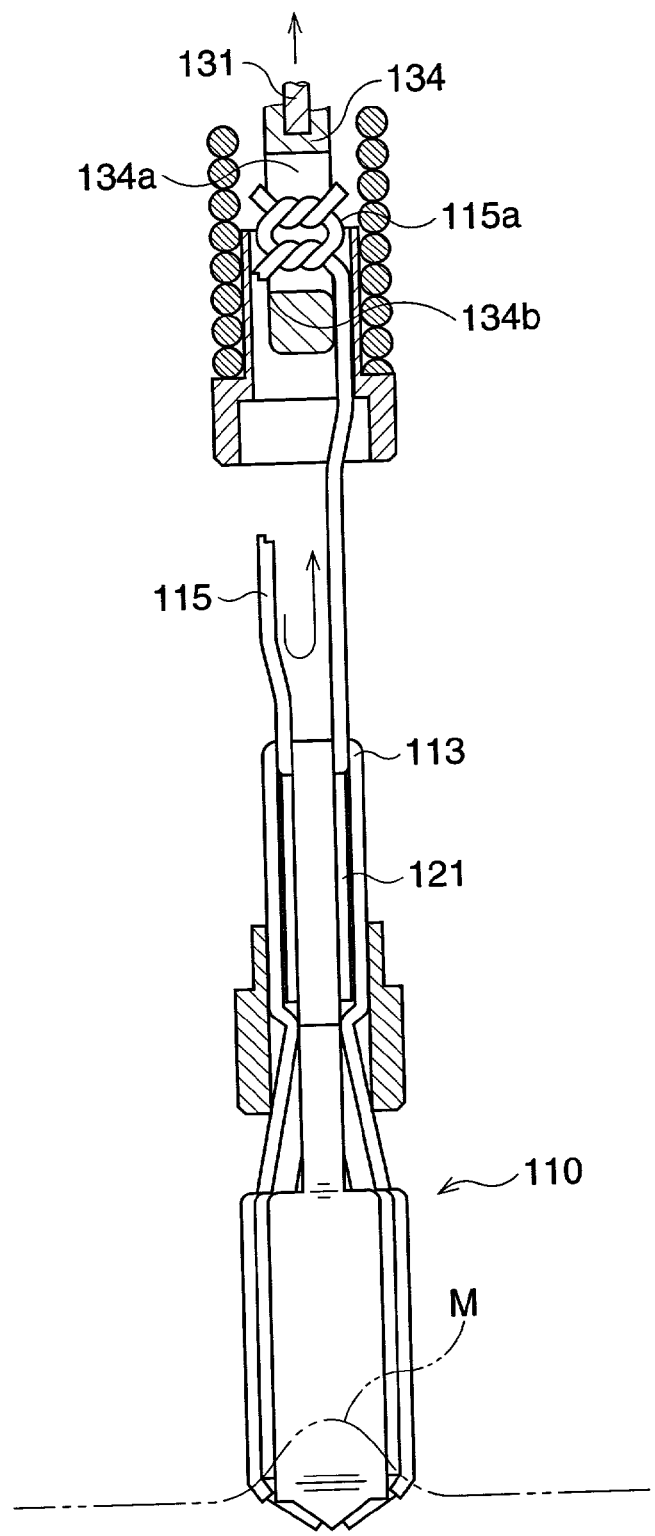
FIG. 21 is a partially sectional plan view showing a clip of a fourth embodiment.

FIG. 21 shows a fourth embodiment in which the acute angle corner 134b is formed on the clip connecting hook and the ends of the clip connecting string 115 are tied in a knot 115a.

According to the second through fourth embodiments, the same effect as the first embodiment can be obtained.

With reference to FIGS. 22 through 26, a fifth embodiment is described below, in which a cutting mechanism is provided for cutting the clip connecting string 115. The parts which correspond to those in the to the above described embodiments are indicated by the same references as those of the above described embodiments.

Figure 22:
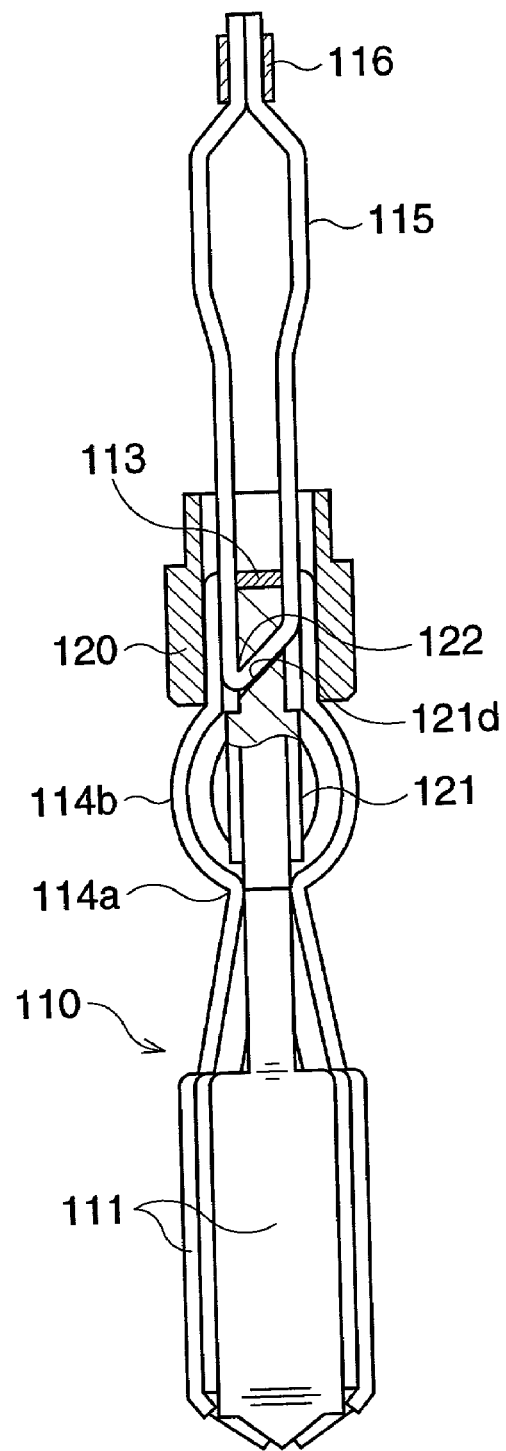
FIG. 22 is a partially sectional view showing a clip unit of a fifth embodiment.
Figure 23:
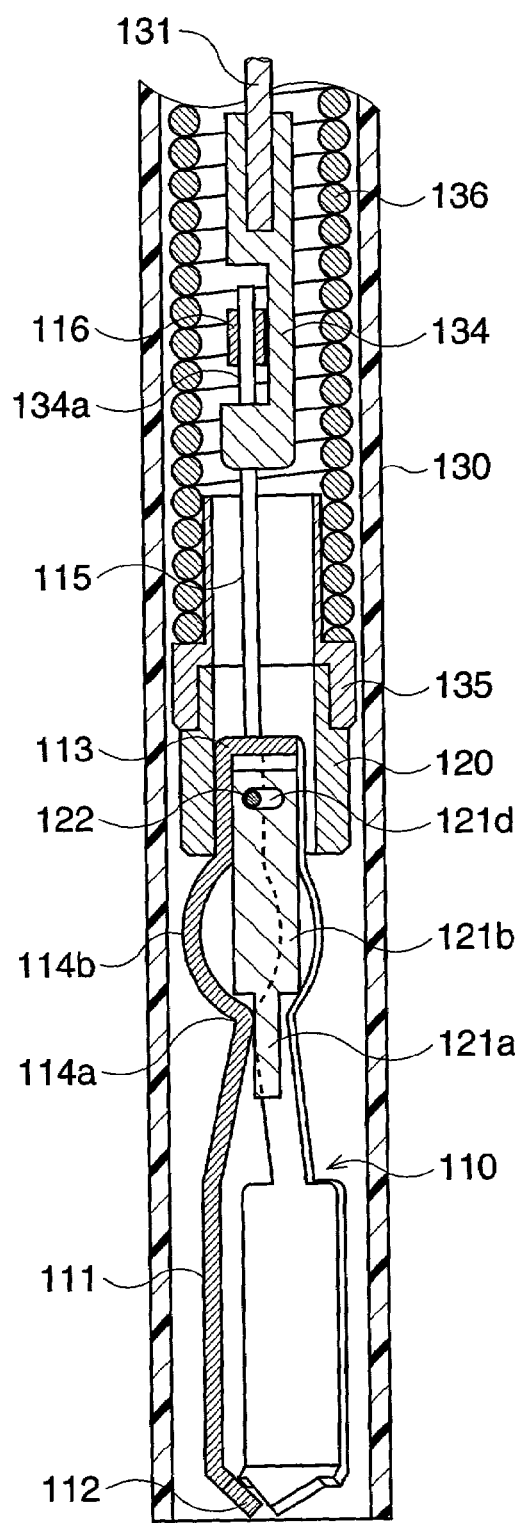
FIG. 23 is a longitudinal sectional view of a distal end of the clip device of the fifth embodiment.

FIG. 22 shows a clip unit containing the clip 110, the clip connecting string 115, the clip open-close ring 120, and the core member 121. FIG. 23 shows a state in which the clip unit is housed in the outer sheath 130. Ends of the clip connecting string 115 are bundled and combined in the pipe 116 in a similar way to that in the second embodiment shown in FIG. 18.

The clip connecting string 115 is passed through a string passing hole 121d formed in a portion close to the base end of the core member 121, and is engaged with the base end portion 113. The string passing hole 121d is inclined by 45 degrees, for example, relative to the longitudinal axis of the core member 121, so that a string cutting edge 122 is formed at an end opening of the string passing hole 121d. Namely, when the clip connecting string 115 is strongly pulled rearward (upward in the drawing), the clip connecting string 115 is cut by the string cutting edge 122. The other constructions are identical with those of the above described embodiments.

Figure 24:
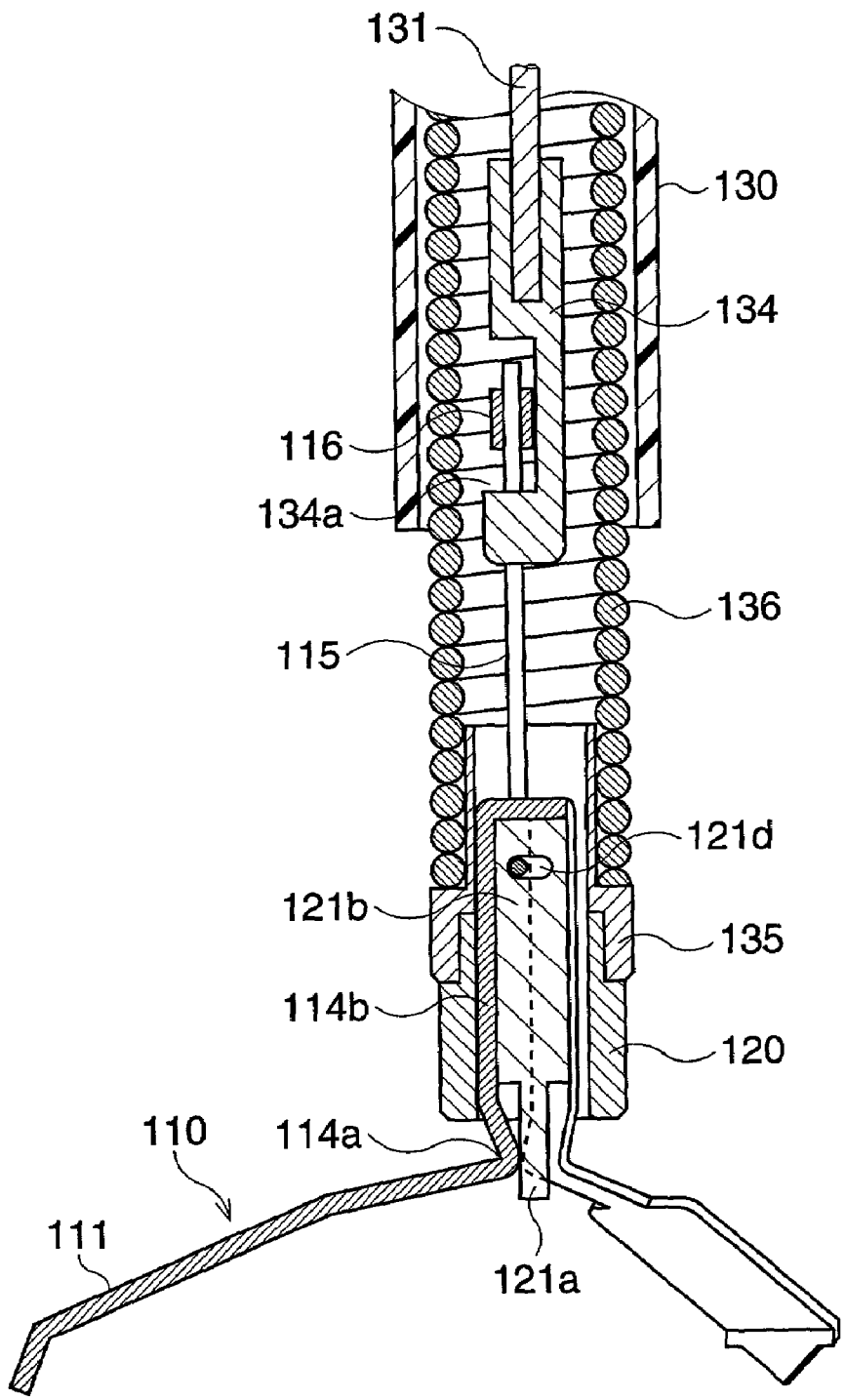
FIG. 24 is a longitudinal sectional view showing the distal end of the clip device when the clip is open, in the fifth embodiment.
Figure 25:
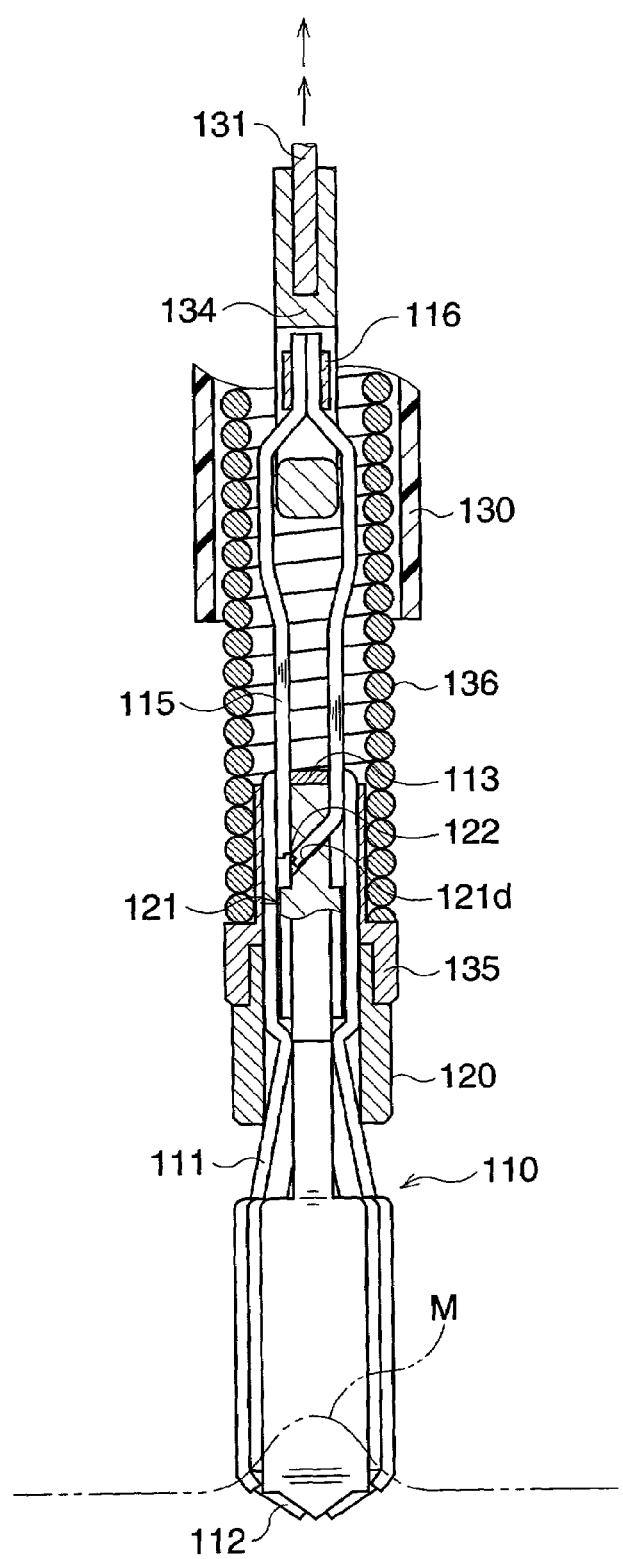
FIG. 25 is a longitudinal sectional view showing the distal end of the clip device, when the clip is closed, in the fifth embodiment.

In the usage of the clip device, while the clip 110 is housed in the outer sheath 130 as shown in FIG. 23, the distal end of the outer sheath 130 is led to the diseased part to be clipped. Then, as shown in FIG. 24, the outer sheath 130 is moved rearward (upward in the drawing), and the operating wire 131 is then pulled, so that the arms 111 are open. After this, when the operating wire 131 is further pulled from the operating unit, as shown in FIG. 25, the arms 111 are pulled into the clip open-close ring 120 and squeezed, so that the claw portions 112 bite into the mucous membrane of the diseased portion M.

When the operating wire 131 is further pulled from the operating unit, the clip connecting string 115 is cut by the string cutting edge 122. Therefore, when the clip connecting string 115 is pulled rearward together with the inner sheath 136, the ring receiving cylinder 135 is separated from the clip open-close ring 120, and the clip 110 is released from the clip connecting string 115.

Thus, the clip 110, in which the arms 111 are closed by the clip open-close ring 120, is clamped on the diseased portion M.

As described above, in the fifth embodiment, the cutting mechanism containing the string cutting edge 122 is provided close to the clip 110, and the clip connecting string 115 is surely cut, so that the clipping operation is smoothly performed.

Figure 26:
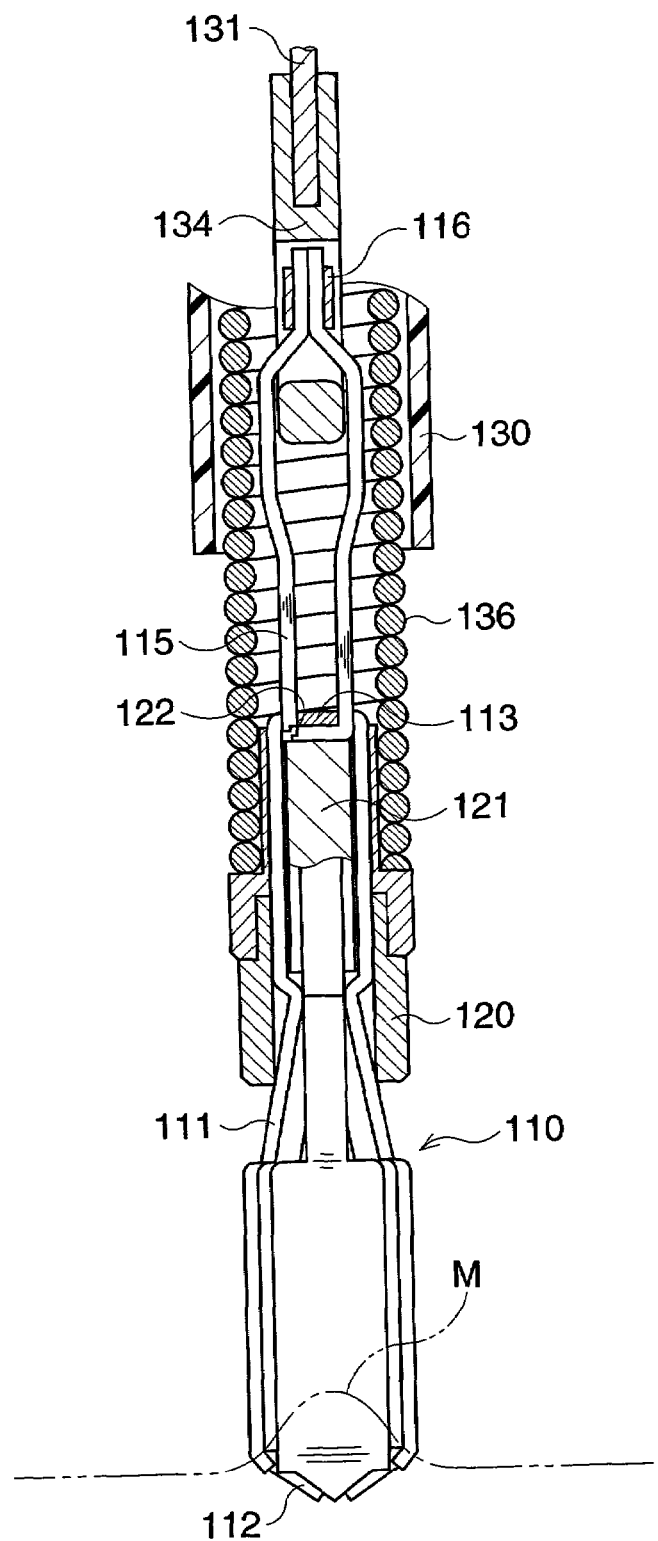
FIG. 26 is a longitudinal sectional view showing the distal end of the clip device, when the clip is closed, in a sixth embodiment.

FIG. 26 shows a sixth embodiment, in which a string cutting edge 116 is provided to a portion of the clip 110 between the base end portion 113 and the arms 111. The operation and effects of the clip device of the sixth embodiment are the same as those of the fifth embodiment.

Figure 27:
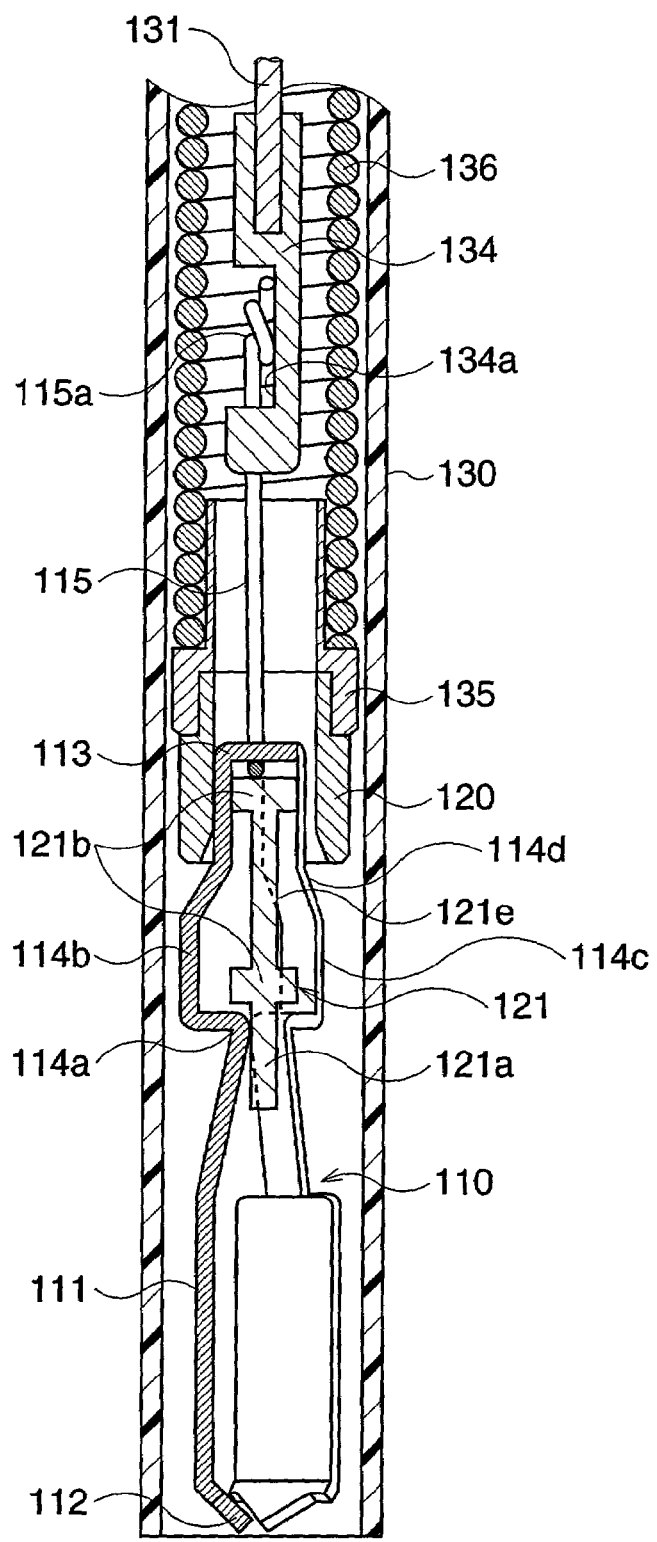
FIG. 27 is a longitudinal sectional view of a distal end of the clip device of a seventh embodiment.
Figure 28:
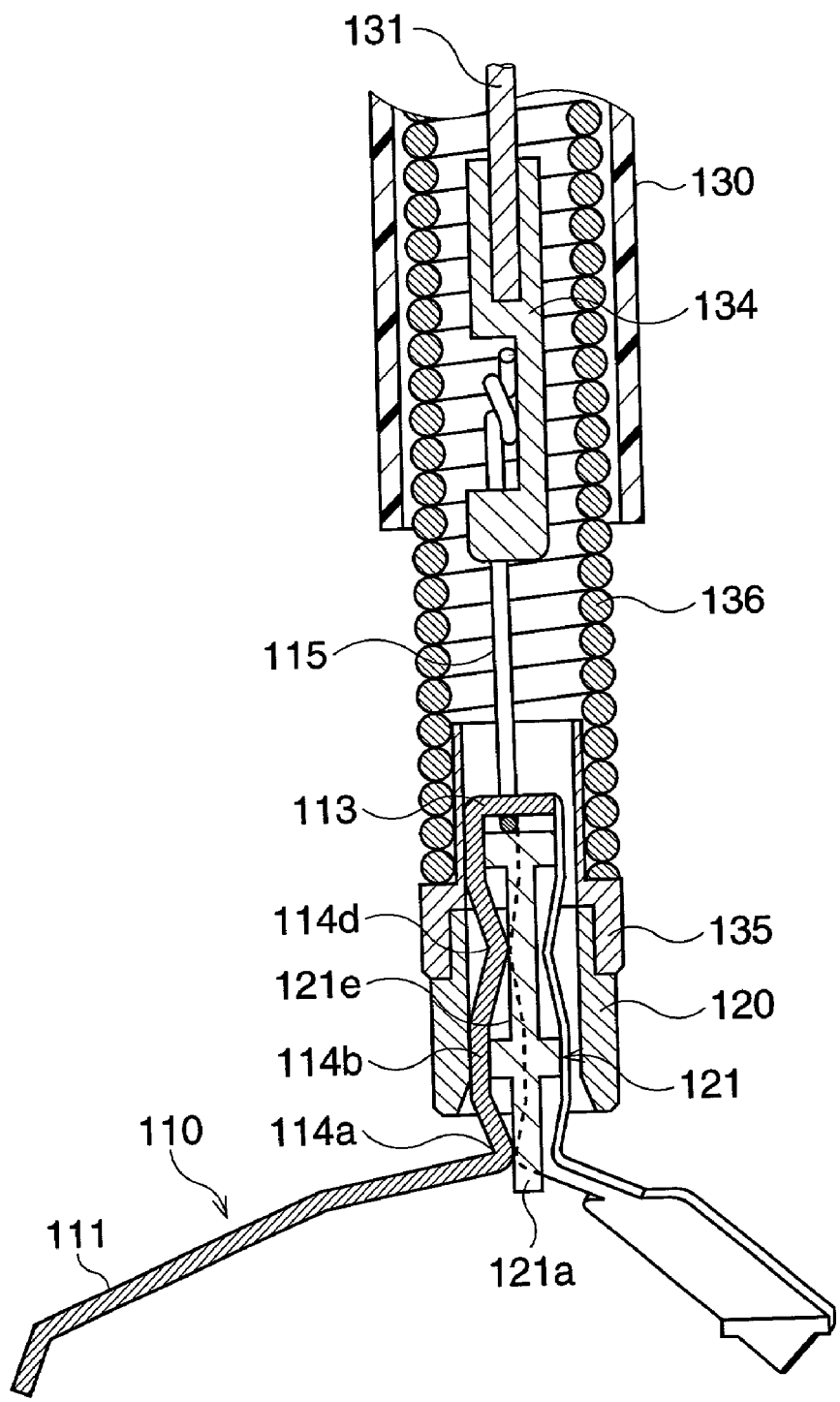
FIG. 28 is a longitudinal sectional view showing the distal end of the clip device when the clip is open, in the seventh embodiment.
Figure 29:
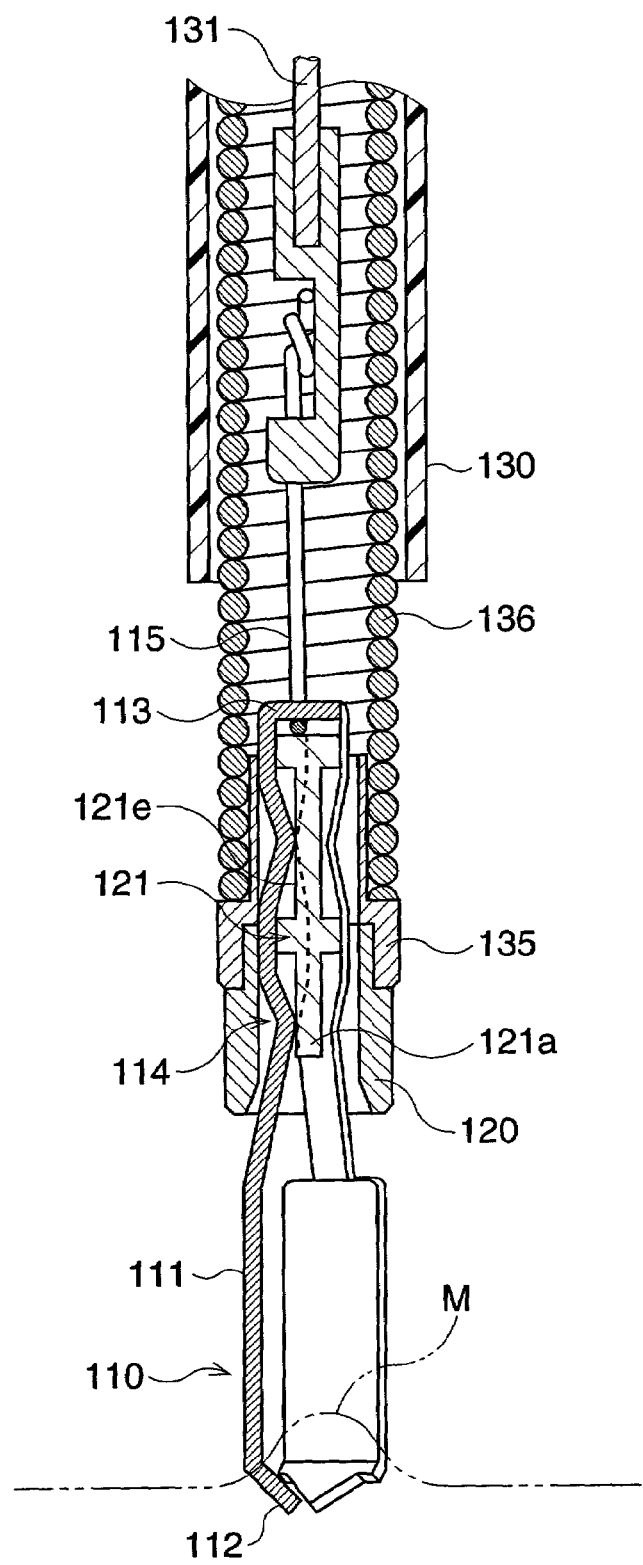
FIG. 29 is a longitudinal sectional view showing the distal end of the clip device, when the clip is closed, in the seventh embodiment.

With reference to FIGS. 27 through 29, a seventh embodiment is described below, in which a cylindrical recess 121e is formed on an outer surface of the core member 121 so as to reduce interference between the clip 110 and the core member 121 when the clip 110 opens and closes. The parts which correspond to those in the previously described embodiments are indicated by the same references.

The cylindrical recess 121e is formed by making part of the large diameter portion 121b approximately the same diameter as that of the small diameter portion 121a. The bulge portion 114b of the open-close deforming portion 114 is formed not in an arc shape in section, as in the first embodiment, but in a bottle-like shape. The bulge portion 114b has a first bent portion 114c, which is bent outwardly at an obtuse angle, and a second bent portion 114d, which is inwardly bent at an obtuse angle.

In the usage of the clip device, while the clip 110 is housed in the outer sheath 130 as shown in FIG. 27, the distal end of the outer sheath 130 is led to the diseased part to be clipped. Then, as shown in FIG. 28, the outer sheath 130 is moved rearward, and the operating wire 131 is then pulled, so that the bulge portion 114b is pulled into the clip open-close ring 120 and is deformed, to open the arms 111. After this, when the operating wire 131 is further pulled from the operating unit, as shown in FIG. 29, the arms 111 are pulled into the clip open-close ring 120 and squeezed, so that the claw portions 112 bite into the mucous membrane of the diseased portion M.

In the open-close operation of the clip 110, the bulge portion 114b is pressed inward by the open-close ring 120, so that the second bent portion 114d is pushed inward to deform toward the core member 121. However, the cylindrical recess 121e (i.e., a frictional resistance reducing portion) is formed to prevent the clip 110 from interfering with the core member 121. Therefore, the second bent portion 114d is not pressed on the core member 121 with a large force, only a small frictional resistance is generated between the core member and the clip 110, and between the clip 110 and the clip open-close ring 120. Accordingly, the clip 110 is smoothly opened and closed with a small operating force.

The other operation and effects of the clip device of the seventh embodiment are the same as those of the previously described embodiments.

Figure 30:
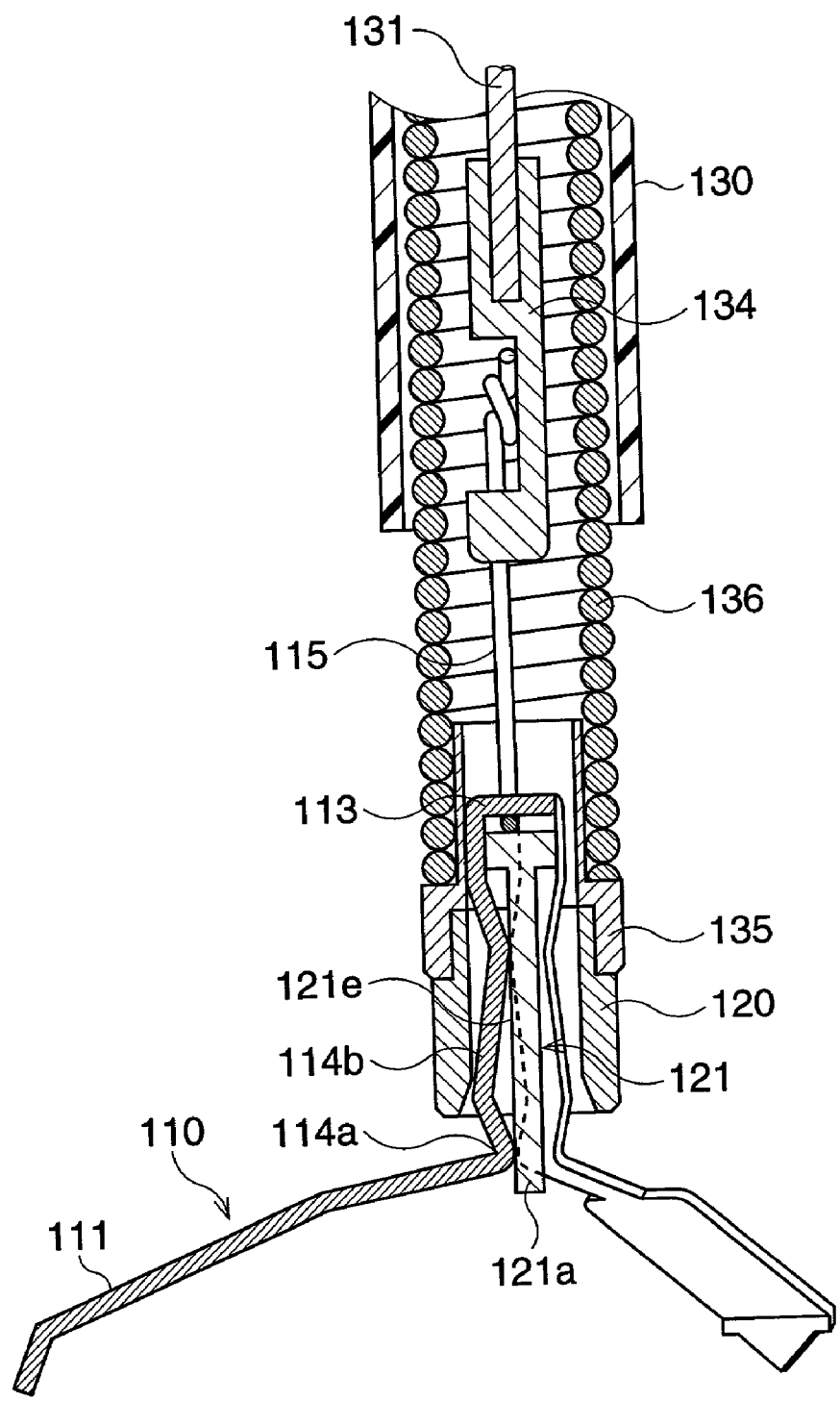
FIG. 30 is a longitudinal sectional view showing the distal end of the clip device when the clip is open, in an eighth embodiment.

FIG. 30 shows an eighth embodiment, in which the cylindrical recess 121e is continued to the small diameter portion 121a. The operation and effects of the clip device of the eight embodiment are the same as those of the seventh embodiment.

Figure 31:
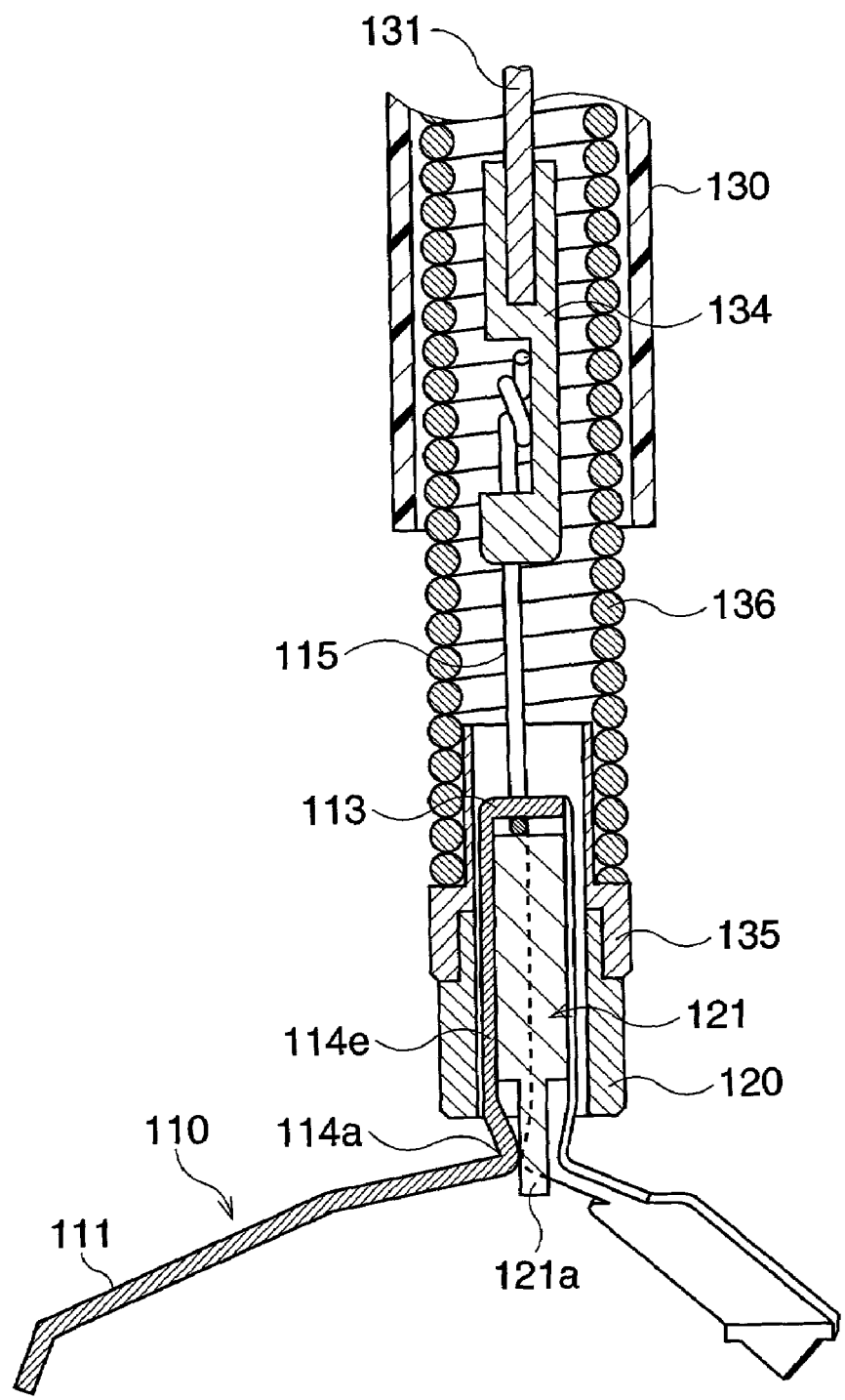
FIG. 31 is a longitudinal sectional view showing the distal end of the clip device when the clip is open, in an ninth embodiment.

FIG. 31 shows a ninth embodiment, in which the cylindrical recess is not provided, as in the seventh and eight embodiments. In the ninth embodiment, the thickness of a part of the clip 110 is less than the other portions so as to reduce frictional resistance. The thin portion 114e is in contact with the core member 121 or the clip open-close ring 120, when the clip 110 opens and closes.

With reference to FIGS. 32 through 35, a tenth embodiment is described below. In the drawings, the parts which correspond to those in the previously described embodiments are indicated by the same references.

Figure 32:
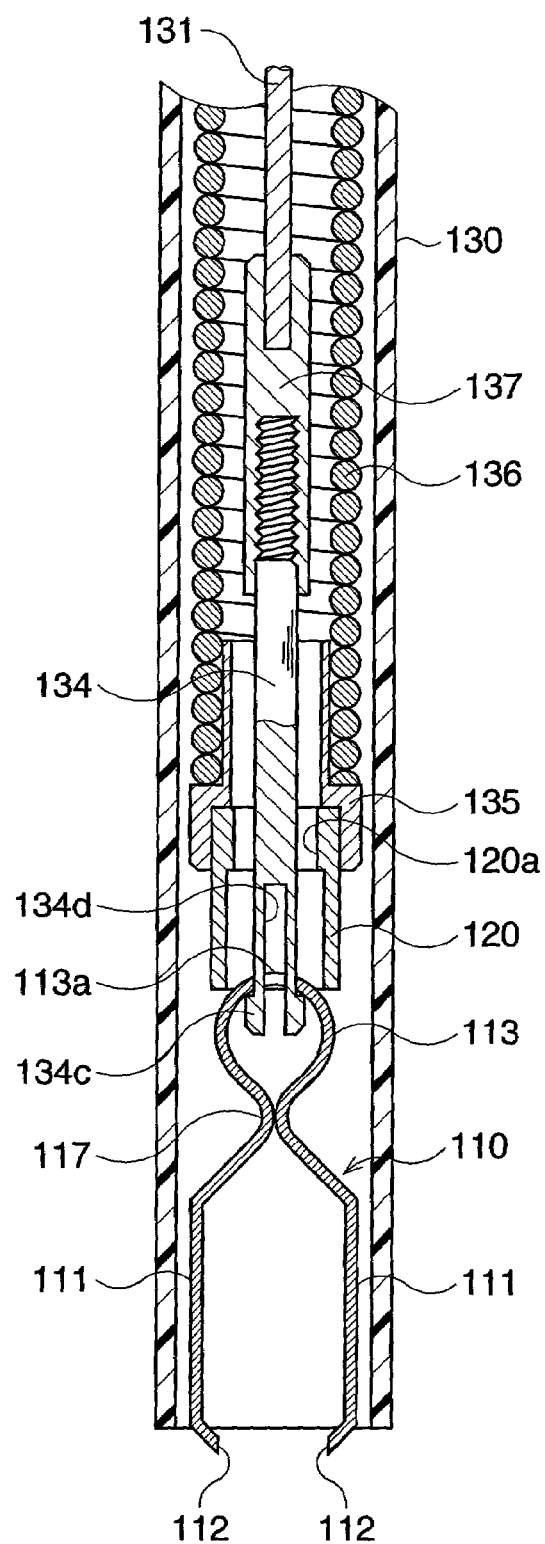
FIG. 32 is a longitudinal sectional view of a distal end of the clip device of a tenth embodiment.

In the tenth embodiment, as shown in FIG. 32, the clip 110, to which no external force applies, is substantially housed in the outer sheath 130. The clip 110 has a pair of arms 111, and in FIG. 32, the arms 111 are parallel to each other.

The clip 110 is formed from a single plate member, such as stainless steel for a spring, and has a pair of arms 111, which are parallel in the neutral condition, and a base end portion 113, to which the arms 111 are connected. The base end portion 113 is annular and extends in approximately 360 degrees. The tips of the arms 111 are inwardly bent to form claw portions 112.

The clip 110 is obtained by bending the plate member without crossing at any portion in such a manner that a boundary portion 117, between the base end portion 113 and the arms 111, is formed in a constricted shape. Namely, the plate member is bent at the boundary portion 117 in such a manner that the plate member is projected toward the inside of the boundary portion 117. Thus, the plate member has peak portions, which are projected toward the inside of the boundary portion 117 and are in contact with each other.

The clip 110, constructed as described above, does not have to be provided with a portion where the breadth is narrow, not even in the boundary portion 117. Namely, the clip 110 has a substantially uniform breadth as a whole. Therefore, the clip 110 has no weak portion, so that the clip 110 cannot be accidentally damaged or deformed while handling. Note that the claws 112 can be made thin or narrow, which does not affect the strength of the clip.

The operating wire 131 is disposed in the axial position of the outer sheath 130, and is operated by the slider 141 to move along the axis of the outer sheath 130. A connecting member 137 is fixed to the tip portion of the operating wire 131, and a clip connecting hook 134 is connected to the connecting member 137. The clip 110 can be engaged with and disengaged from the clip connecting hook 134.

The tip portion 134c of the clip connecting hook 134 has a greater diameter than the other portions thereof. A slot 134d, extending along the axis of the clip connecting hook 134, is formed therein to transverse the tip portion 134c. A connecting hole 113a is formed in the base end portion 113, and the tip portion 134c is engaged with the connecting hole 113a, so that the clip 110 is connected to the clip connecting hook 134. Thus, by elastically deforming the clip connecting hook 134 into the narrowing slot 134d, the clip connecting hook 134 can be released from the clip 110.

A clip open-close ring 120, for deforming the base end portion 113, is mounted in the outer sheath 130. An inner wall of a base end portion 120a of the clip open-close ring 120 is cylindrical, and has a diameter less than the other portion of the clip open-close ring 120. The base end portion 113 of the clip 110 is deformed by engaging with an inner wall of the clip open-close ring 120.

The other constructions are identical with those of the previously described embodiments.

An operation of the tenth embodiment is as follows. First, the outer sheath 130 is inserted into a treatment tool insert channel of an endoscope not shown, and keeping a state in which the clip 110 is projected from the outer sheath 130, the clip open-close ring 120 is pushed out toward the clip 110, by pulling the operating wire 131.

Figure 33:
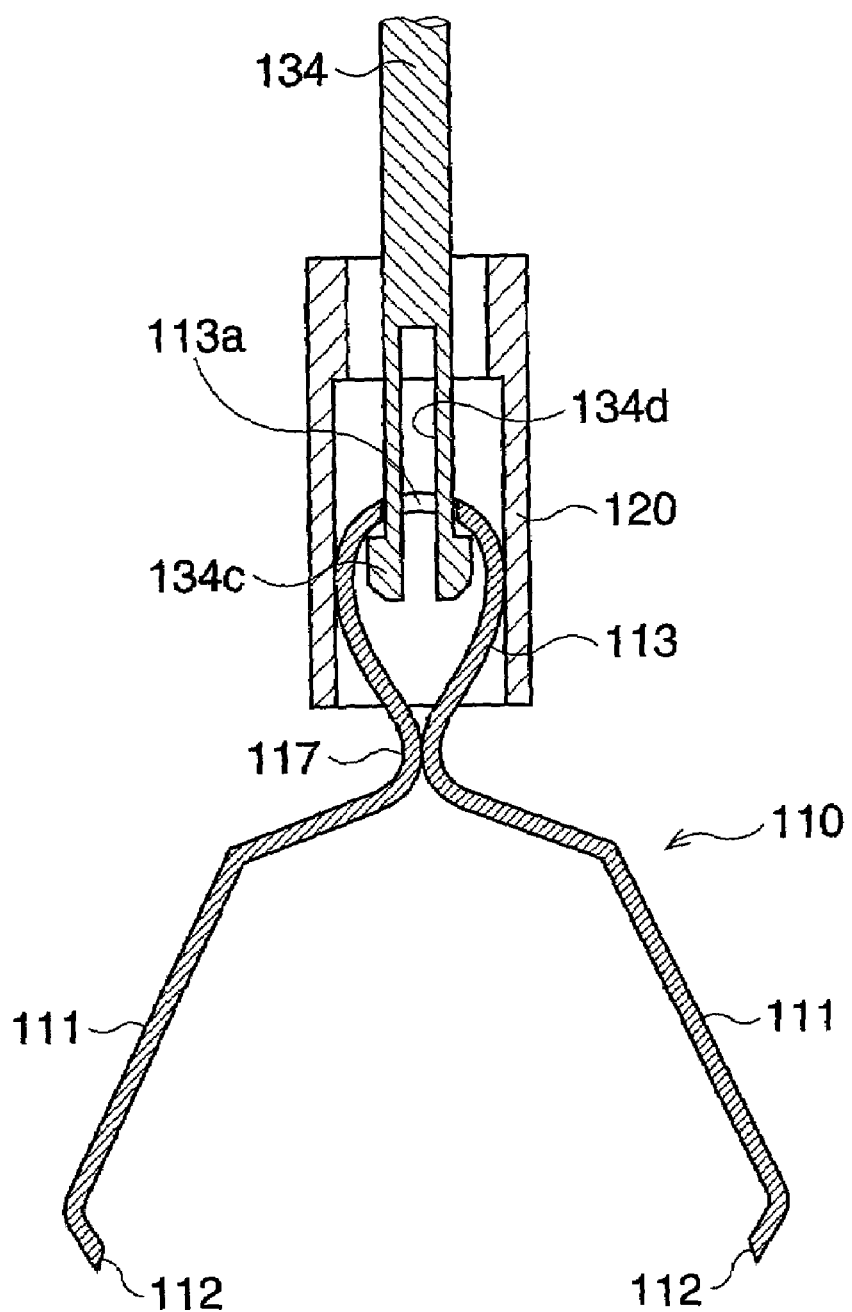
FIG. 33 is a sectional view of a clip of the tenth embodiment, when open.

As a result, as shown in FIG. 33, the base end portion 113 is pulled into the clip open-close ring 120, and deformed, so that the arms 111 are open.

Figure 34:
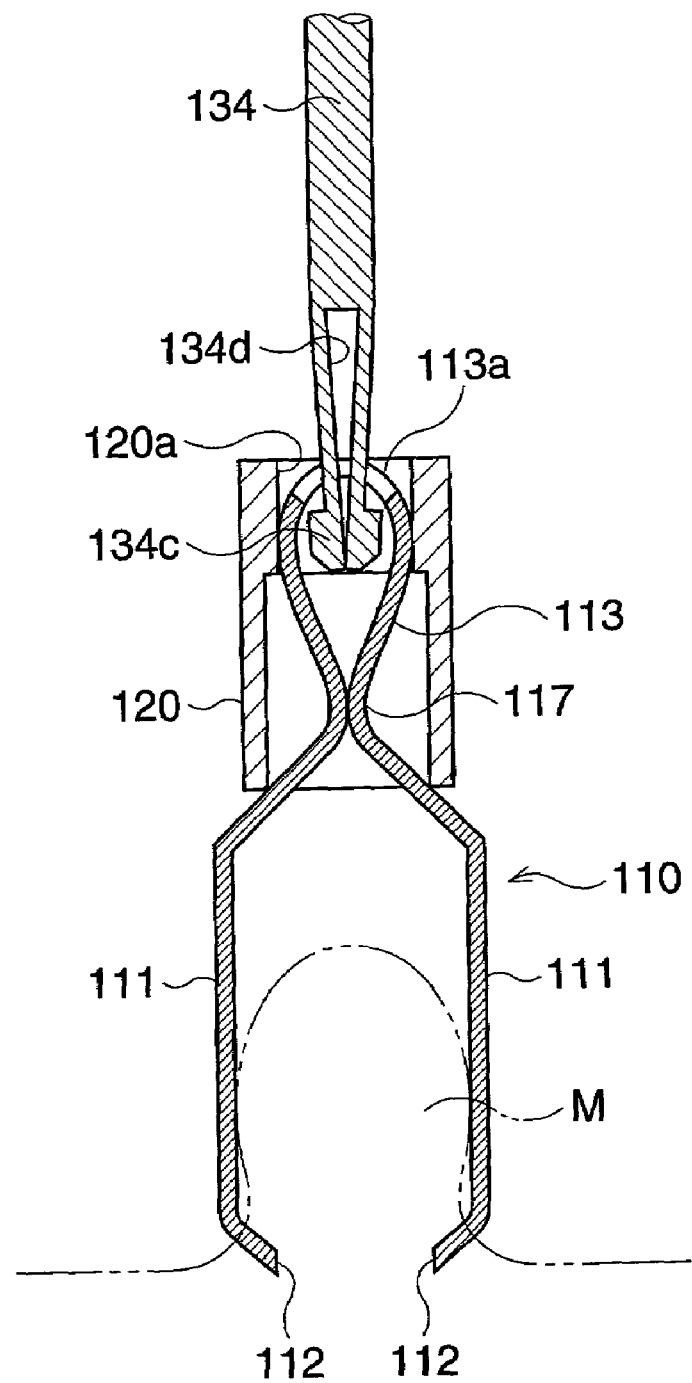
FIG. 34 is a sectional view of the clip of the tenth embodiment, when closed.

Maintaining this condition, the distal end of the outer sheath 130 is positioned in such a manner that the diseased portion M lies between the arms 111. After that, when the clip open-close ring 120 is pushed out toward the clip 110, as shown in FIG. 34, the tip portion of the clip open-close ring 120 presses the arms 111 while the base end portion 113 is further deformed, so that the arms 111 become parallel to each other, and the claw portions 112 bite into a mucous membrane of the diseased portion M.

The base end portion 113 of the clip 110 is pulled into the base end portion 120a of the clip open-close ring 120, and is squeezed or deformed by the clip open-close ring 120. Due to this, the clip connecting hook 134 is pressed, so that the clip connecting hook 134 can pass through the connecting hole 113a.

Figure 35:
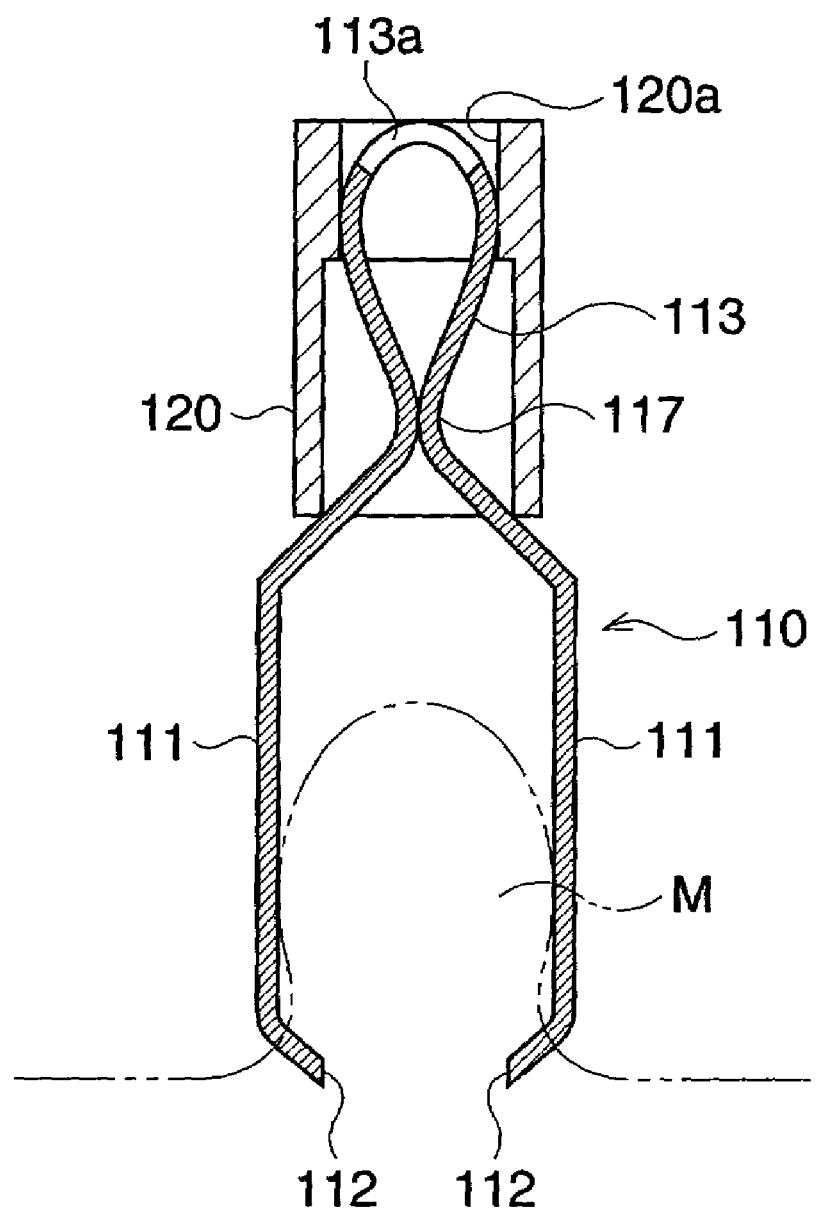
FIG. 35 is a sectional view of the clip of the tenth embodiment, when clamped.
Figure 36:
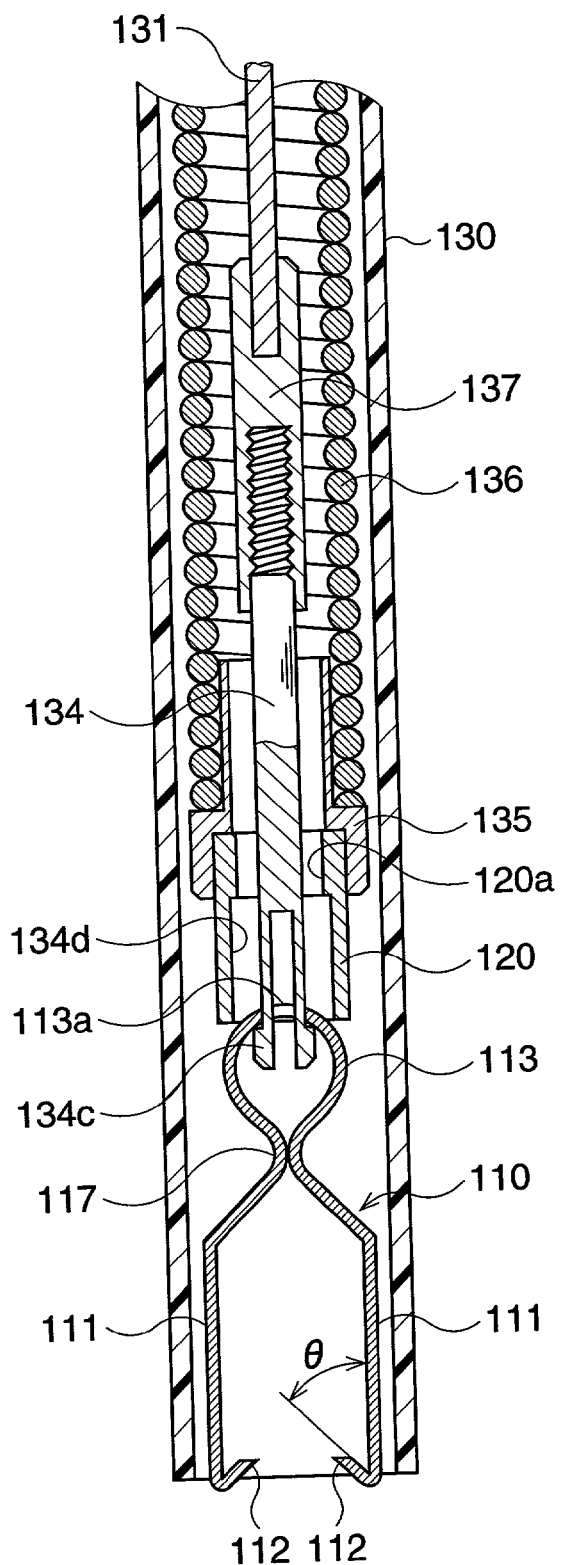
FIG. 36 is a longitudinal sectional view of a distal end of the clip device of an eleventh embodiment.
Figure 37:
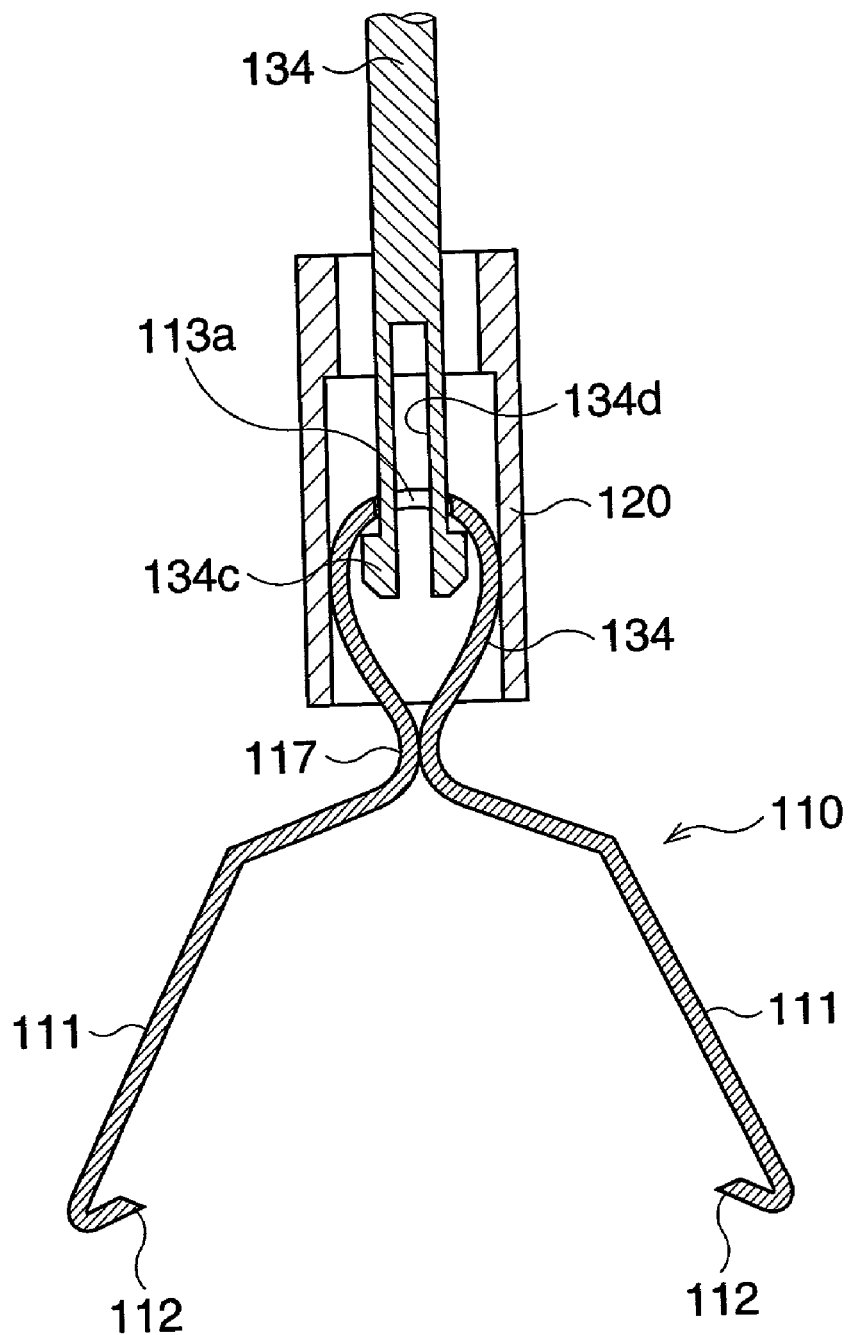
FIG. 37 is a sectional view of a clip of the eleventh embodiment, when open.
Figure 38:
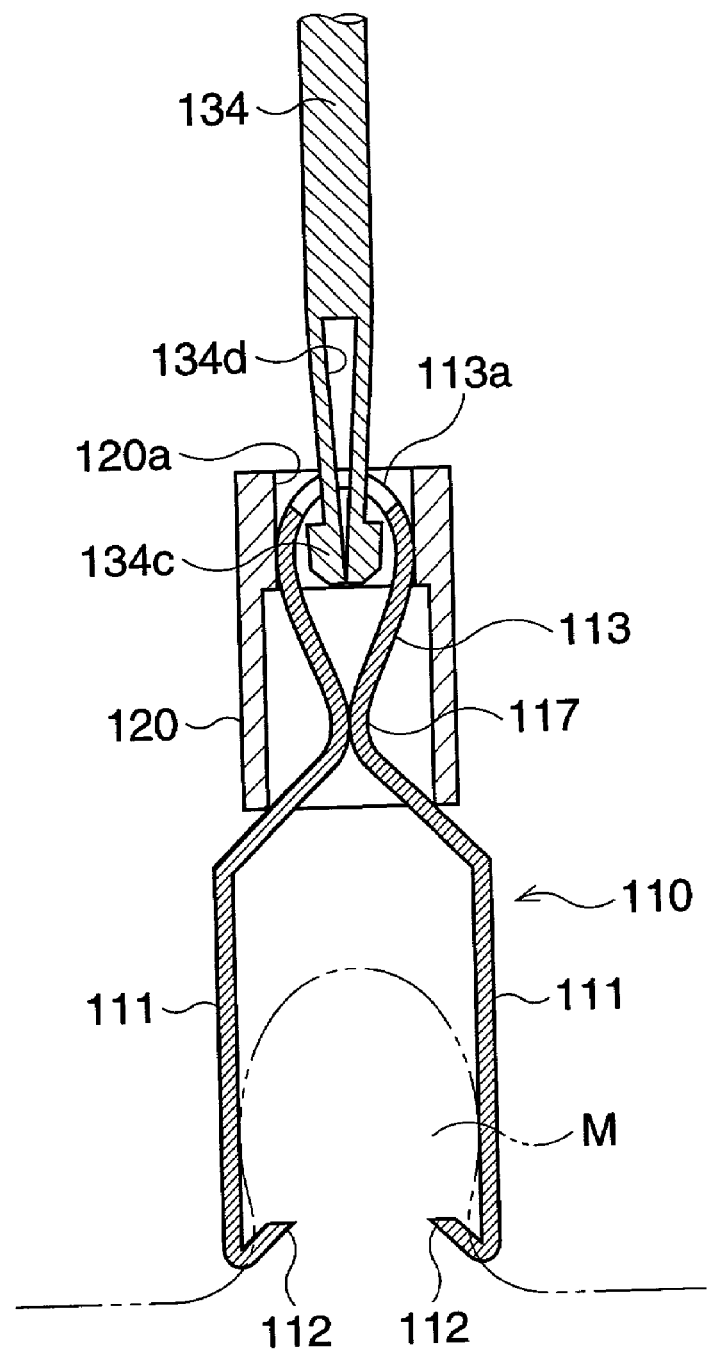
FIG. 38 is a sectional view of the clip of the eleventh embodiment, when closed.
Figure 39:
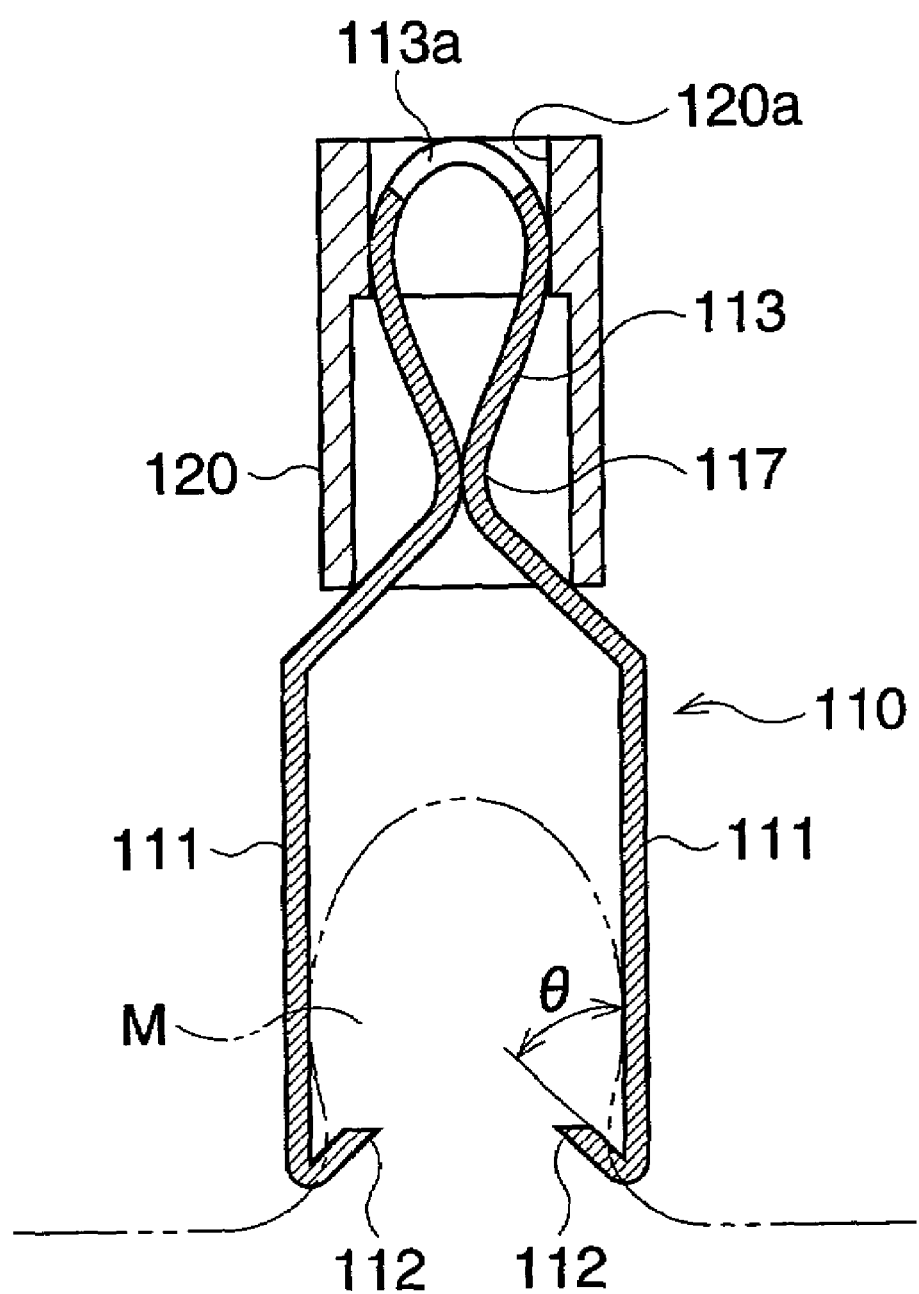
FIG. 39 is a sectional view of the clip of the eleventh embodiment, when clamped.
Figure 40:
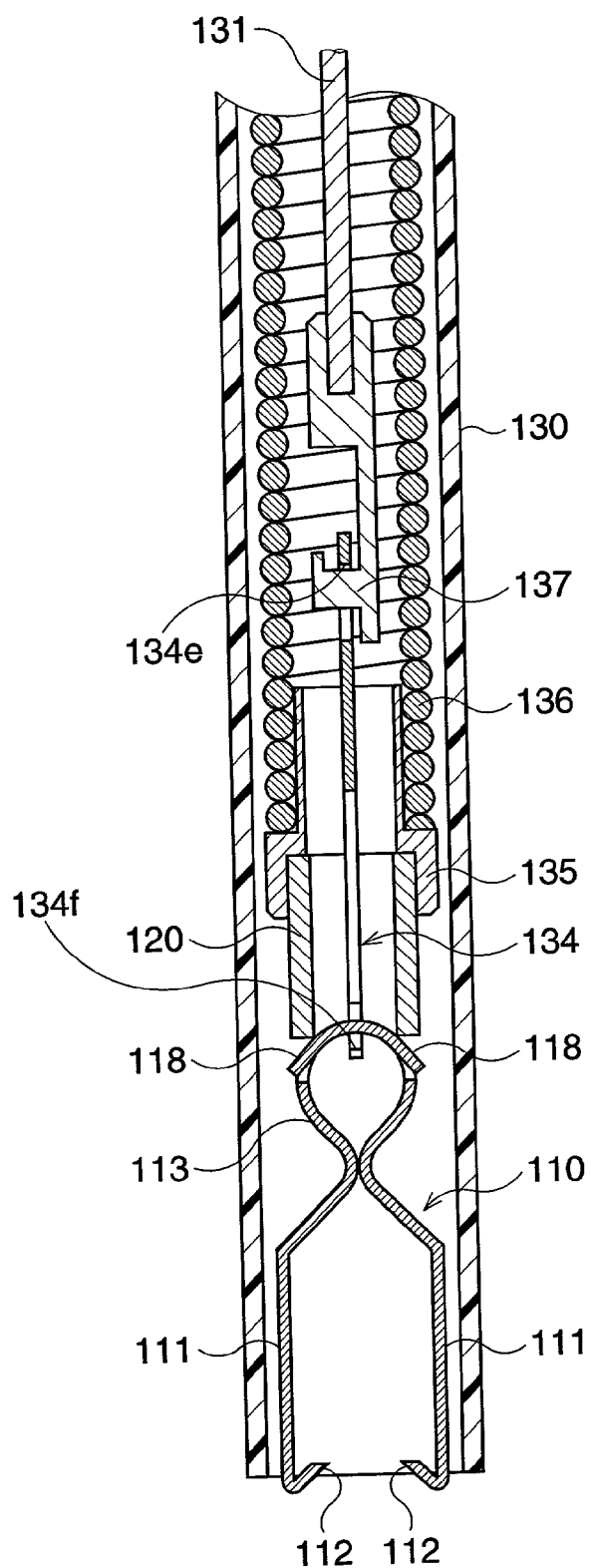
FIG. 40 is a longitudinal sectional view of a distal end of the clip device of a twelfth embodiment.

Thus, the clip connecting hook 134 is released from the clip 110, and the outer sheath 130 is removed from the diseased portion M. Thus, as shown in FIG. 35, the clip 110 to which the clip open-close ring 120 is attached, remains clamping on the mucous membrane of the diseased portion M.

As described above, according to the tenth embodiment, since the clip 110 has a uniform breadth along any portion thereof, there is no weak portion, and thus, the clip 110 cannot be accidentally damaged or deformed during handling.

With reference to FIGS. 36 through 39, which correspond to FIGS. 32 through 35 of the tenth embodiment, respectively, an eleventh embodiment is described below. In the drawings, the parts which correspond to those in the previously de-scribed embodiments are indicated by the same references.

In the eleventh embodiment, the difference from the tenth embodiment is the shape of the claw portions 112, which are bent inward with an acute angle (i.e., the angle θ is less than 90 degrees). The angle θ can be between 30 degrees and 60 degrees. The other constructions are identical with those of the tenth embodiment.

Although the operation of the eleventh embodiment is basically the same as that of the tenth embodiment, the merit of the eleventh embodiment is that the claw portions 112 more firmly bite into mucous membrane of a diseased portion M, in comparison with the tenth embodiment, since the claw portions 112 are engaged with the mucous membrane in a hook-like manner. Therefore, the clip 110 does not come off the diseased portion M easily.

Note that, if the angle θ is close to 90 degrees, the claw portions 112 may easily come off the mucous membrane M, and if the angle θ is close to 0 degrees, the claw portions 112 hardly bite into the mucous membrane M. If the angle θ is from 30 to 60 degrees, the claw portions 112 easily bite into the mucous membrane M, and do not come off easily.

With reference to FIGS. 40 through 44, a twelfth embodiment is described below. In the drawings, the parts which correspond to those of the previously described embodiments are indicated by the same references.

Figure 41:
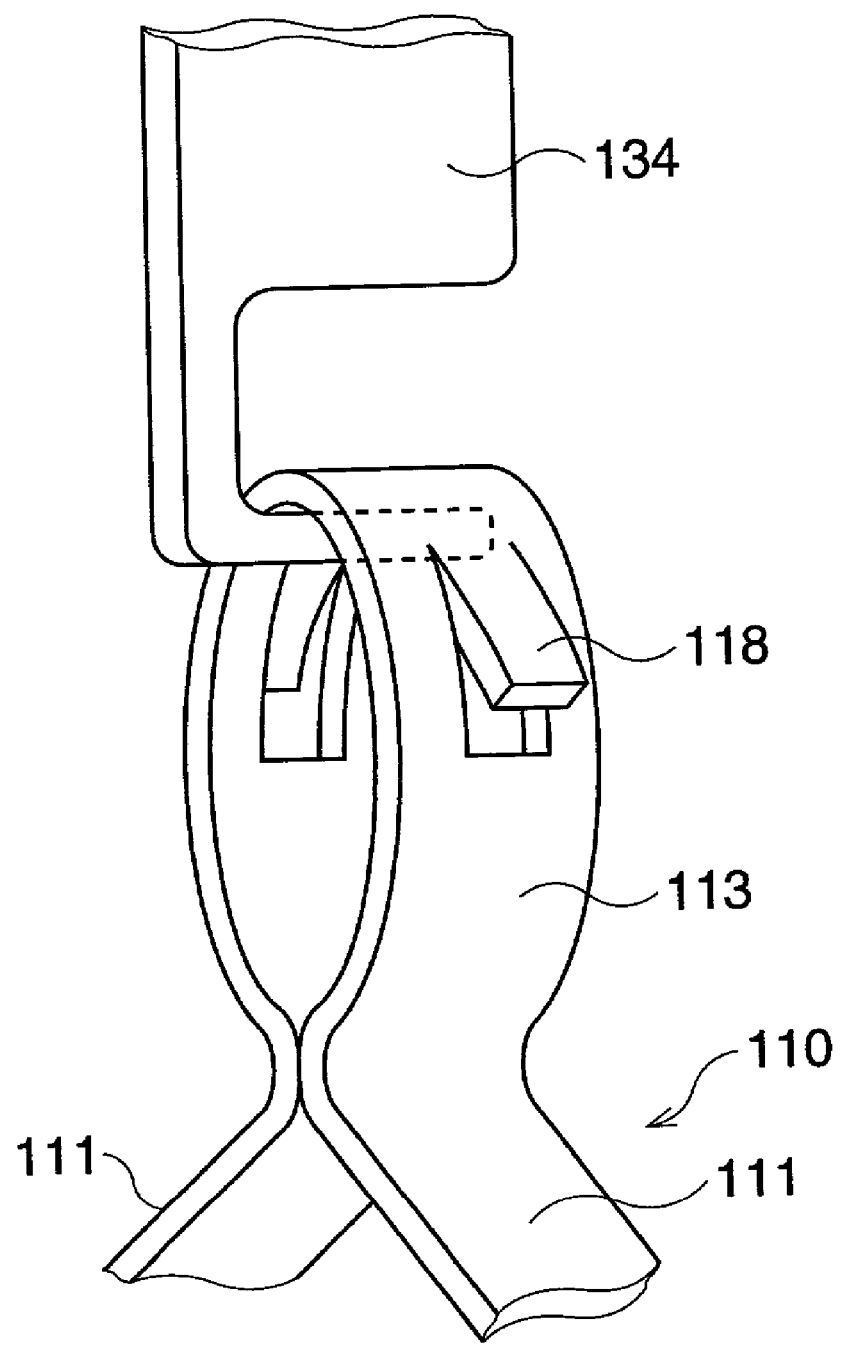
FIG. 41 is a partial perspective view of a base end portion of a clip of the twelfth embodiment.

In the twelfth embodiment, the clip connecting hook 134 has an upper hook portion 134e and a lower hook portion 134f. The upper hook portion 134e is engaged with the connecting member 137 connected to the tip of the operating wire 131. The base end portion 113 of the clip 110 is detachably engaged with the lower hook portion 134f. A pair of stoppers 118 is provided to the base end portion 113. As shown in FIG. 41, each of the stoppers 118 is formed by cutting a part of the base end portion 113, and is extended outward from the base end portion 113 to function as a flat spring. The clip open-close ring 120 is a cylindrical member in which a small diameter portion is not provided, as in the eleventh embodiment (see FIG. 36, for example).

The other constructions are identical with those of the eleventh embodiment.

Figure 42:
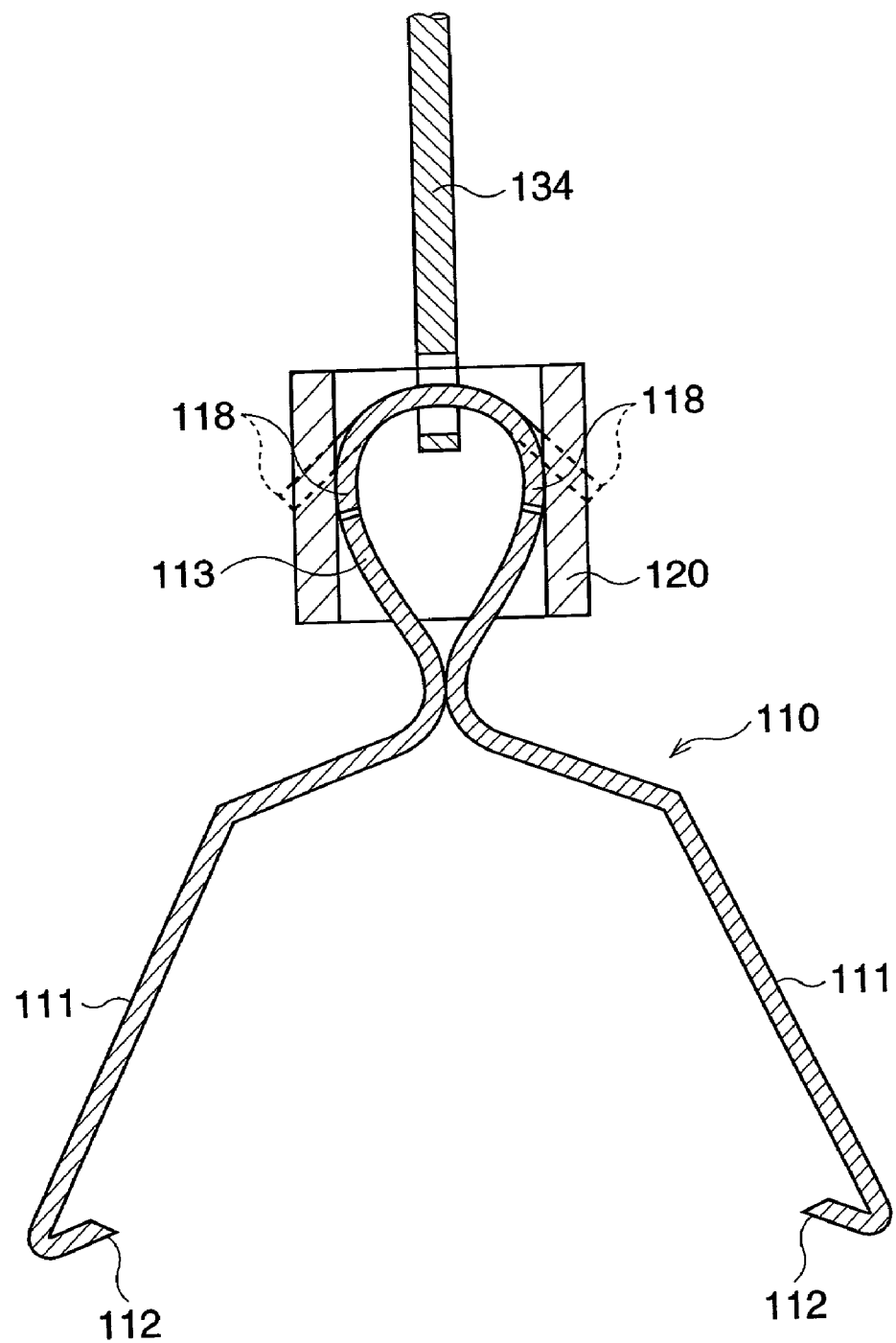
FIG. 42 is a sectional view of the clip of the twelfth embodiment, when open.

The operation of the twelfth embodiment is as follows. First, the clip 110 is projected from the outer sheath 130, and the clip open-close ring 120 is then pushed out toward the clip 110, by pulling the operating wire 131. Due to this, as shown in FIG. 42, the base end portion 113 is pulled into the clip open-close ring 120, and deformed, so that the arms 111 are open. At this time, the stoppers 118 are engaged with an inner wall of the clip open-close ring 120, so that the stoppers 118 are deformed and squeezed.

Figure 43:
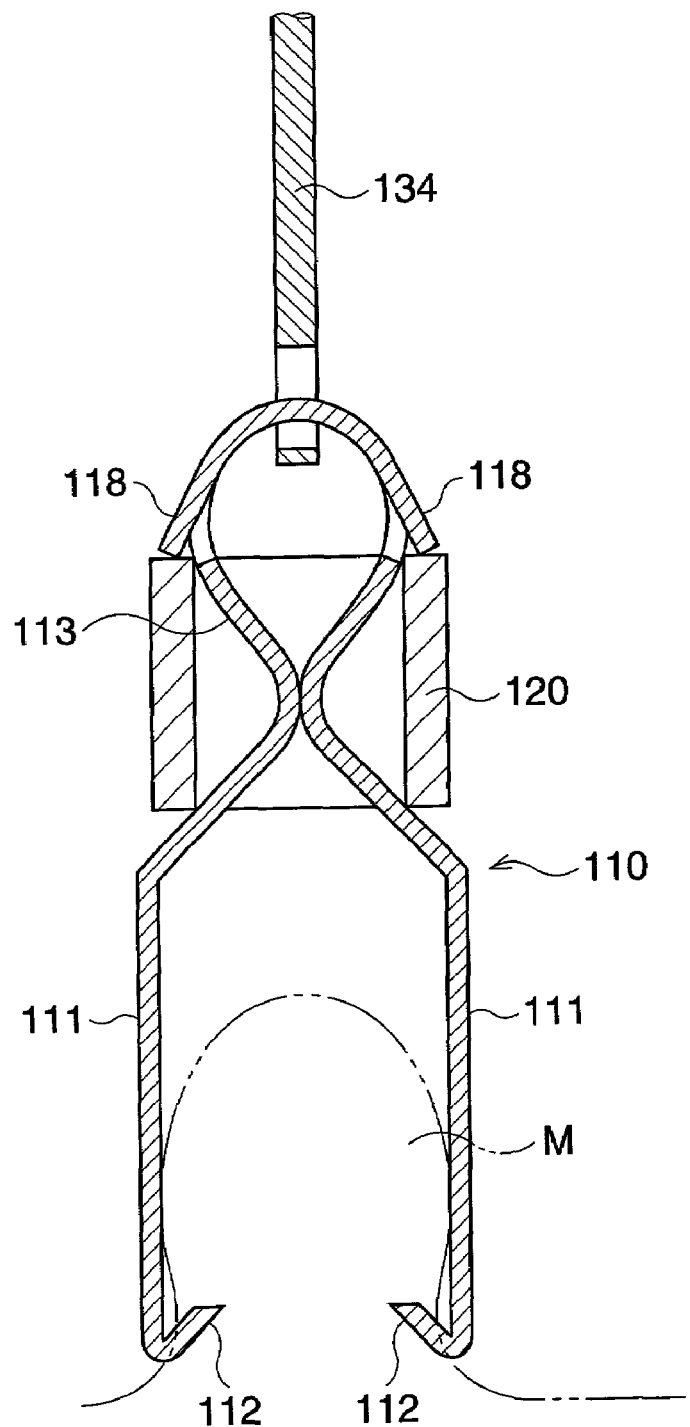
FIG. 43 is a sectional view of the clip of the twelfth embodiment, when closed.

Keeping this condition, the distal end of the outer sheath 130 is positioned in such a manner that the diseased portion M lies between the arms 111. After that, when the clip open-close ring 120 is pushed out toward the clip 110, as shown in FIG. 43, the tip portion of the clip open-close ring 120 presses the arms 111 while the base end portion 113 is further deformed, so that the arms 111 become parallel to each other, and the claw portions 112 stick into the mucous membrane of the diseased portion M. At the same time, the stoppers 118 are projected from the upper end of the clip open-close ring 120.

Figure 44:
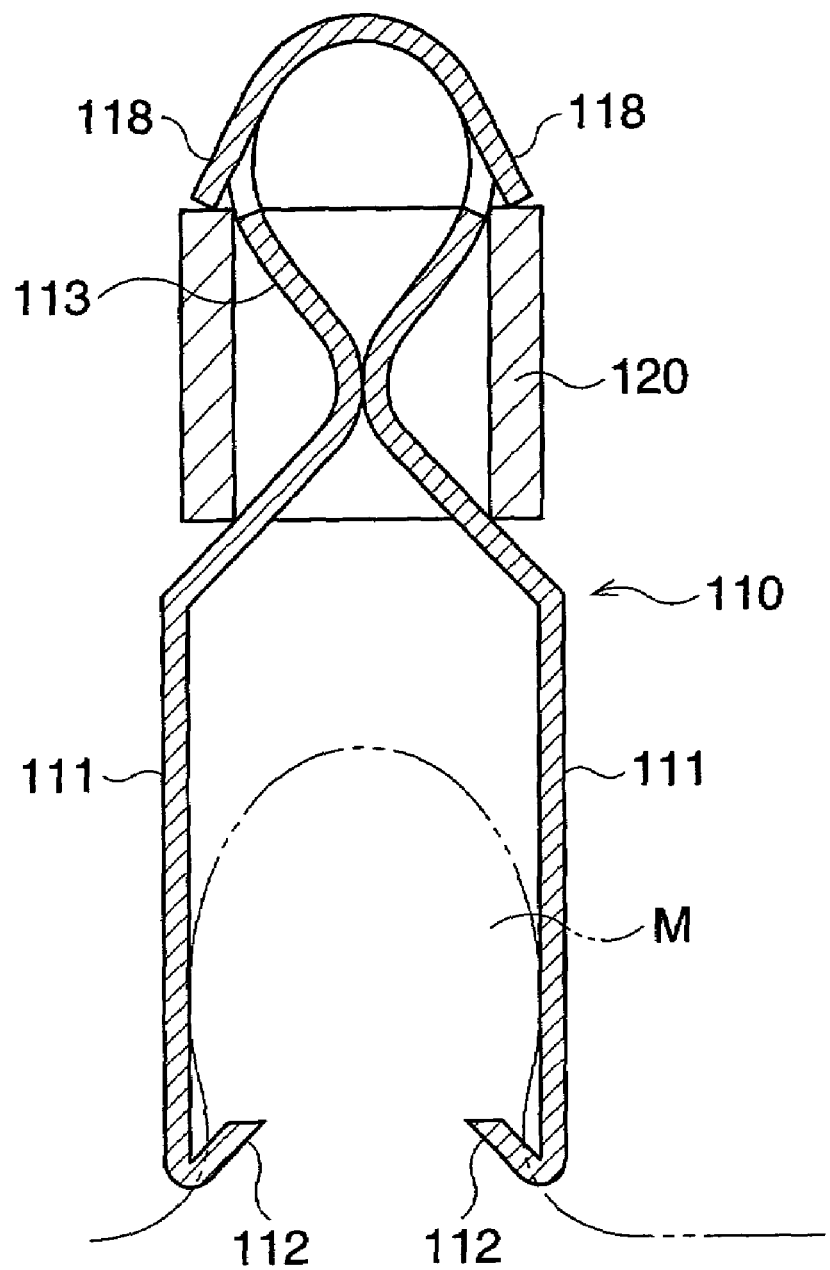
FIG. 44 is a sectional view of the clip of the twelfth embodiment, when clamped.
Figure 45:
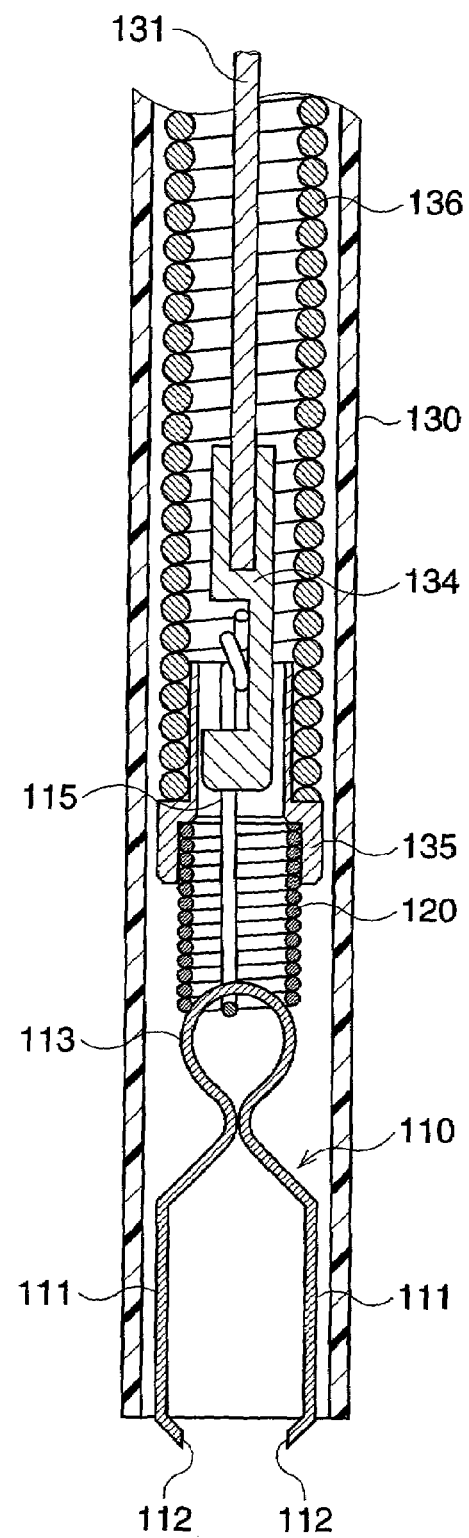
FIG. 45 is a longitudinal sectional view of a distal end of the clip device of a thirteenth embodiment.

Then, the clip connecting hook 134 is disengaged from the base end portion 113, and is moved upward in FIG. 43, so that the clip 110, in which the arms 111 are kept in the closed condition by the clip open-close ring 120, remains at the diseased portion M after being clamped, as shown in FIG. 44.

In this clamping condition, since the stoppers 118 are engaged with the upper end of the clip open-close ring 120, the clip open-close ring 120 is prevented from disengaging from the clip 110. Accordingly, even if an external force is applied to the clip open-close ring 120, the clip open-close ring 120 is not released from the clip 110, and therefore, the clip 110 does not come off the diseased portion M.

As described above, according to the twelfth embodiment, when the clip open-close ring 120 is engaged with the clip 110, the engaging condition is maintained by the stoppers 118. Therefore, the clip is held closed, so that the clip 110 does not easily come off the diseased portion M because of an external force.

With reference to FIGS. 45 through 49, a thirteenth embodiment is described below. In the drawings, the parts which correspond to those in the previously described embodiments are indicated by the same references.

In the thirteenth embodiment, the clip open-close ring 120 is a coil pipe, which is obtained by tightly winding stainless steel wire at a constant diameter. The base end portion 113 of the clip 110 is pulled into the clip open-close ring 120, and is pressed to deform from a circular shape to an oval shape in section.

Figure 46:
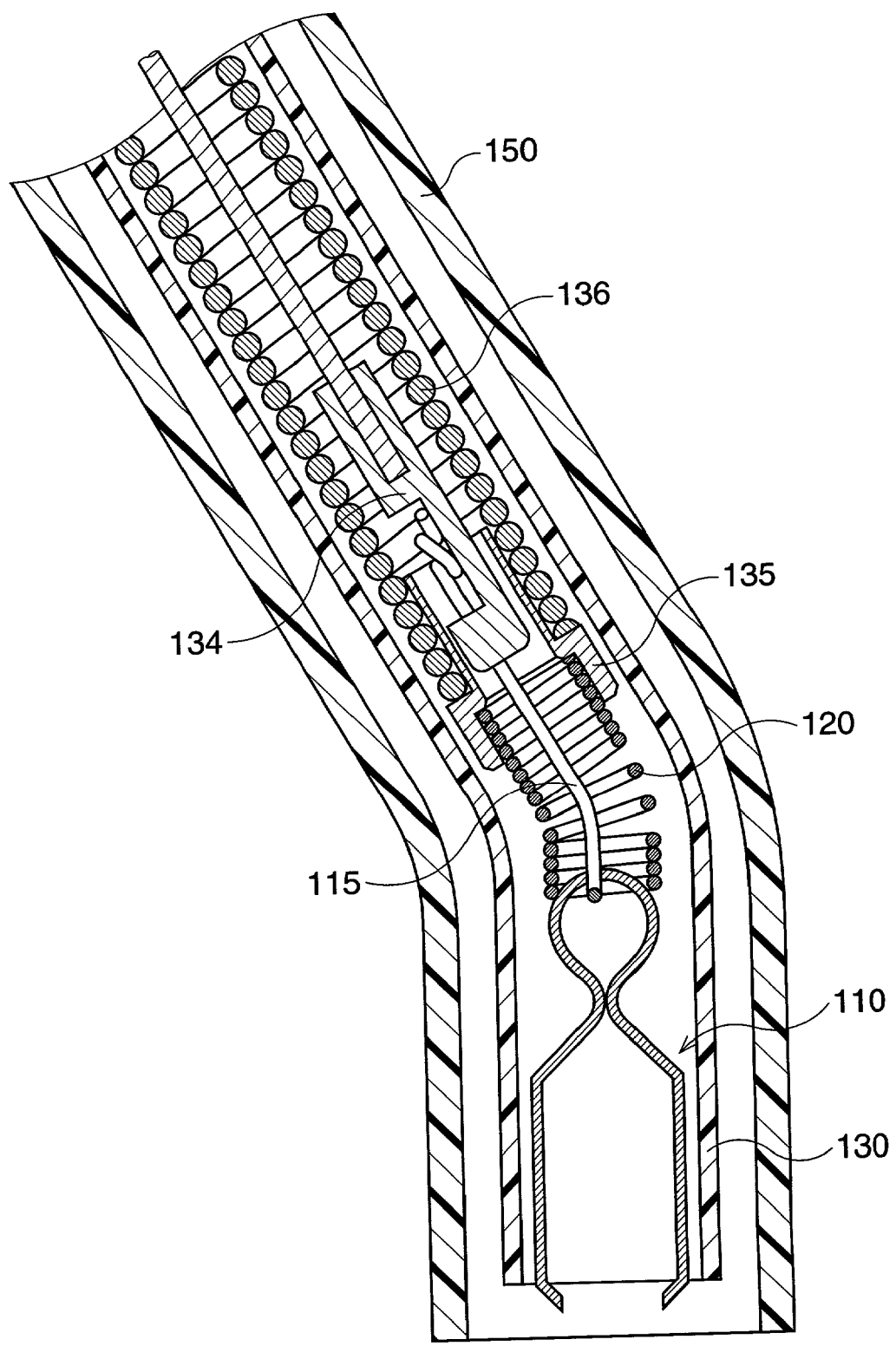
FIG. 46 is a longitudinal sectional view of the clip device shown in FIG. 45, which is inserted in a treatment tool insert channel of an endoscope.
Figure 47:
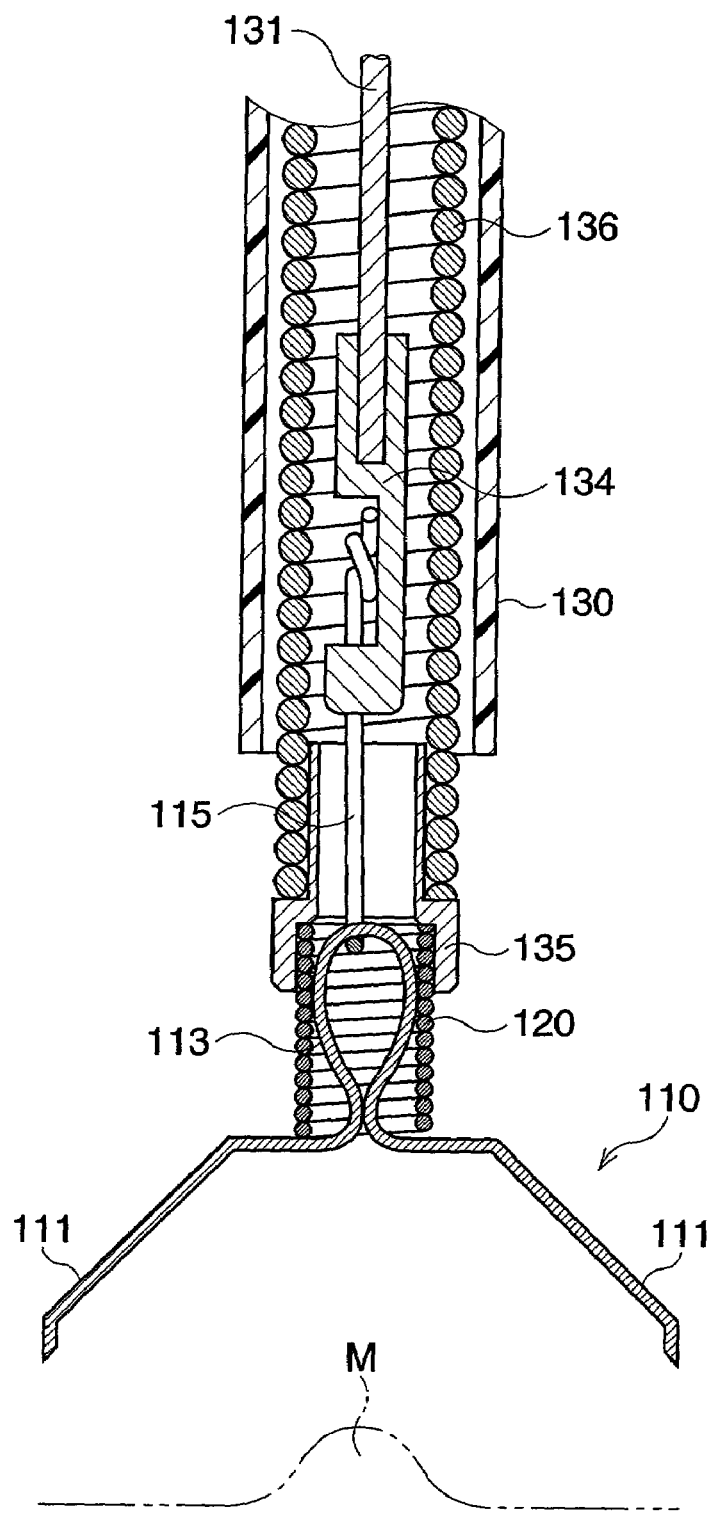
FIG. 47 is a longitudinal sectional view showing the distal end of the clip device when the clip is open, in the thirteenth embodiment.

The clip device of the thirteenth embodiment is inserted into a treatment tool insert channel 150 of an endoscope, and as shown in FIG. 46, the clip device passes through a bending portion of the treatment tool insert channel 150, in which the clip open-close ring 120 is bent with the clip connecting string 115 and the outer sheath 130.

Thus, in the distal portion of the clip device, the only hard portion, which will not bend freely, is the clip 110. Therefore, even when the treatment tool insert channel 150 is bent with a considerably small radius of curvature, the clip device can smoothly pass through the treatment tool insert channel 150.

When the distal end of the clip device is projected from the distal end of the treatment tool insert channel 150 to the inside of a human body, the outer sheath 130 is slightly pulled to the operating unit 140 so that the clip 110 is projected from the distal end of the outer sheath 130, and the operating wire 131 is then pulled toward the operating unit 140.

Thus, the base end portion 113 of the clip 110 is pulled into the clip open-close ring 120, to deform from a circular shape to an oval shape, so that the pair of arms 111 are opened.

Figure 48:
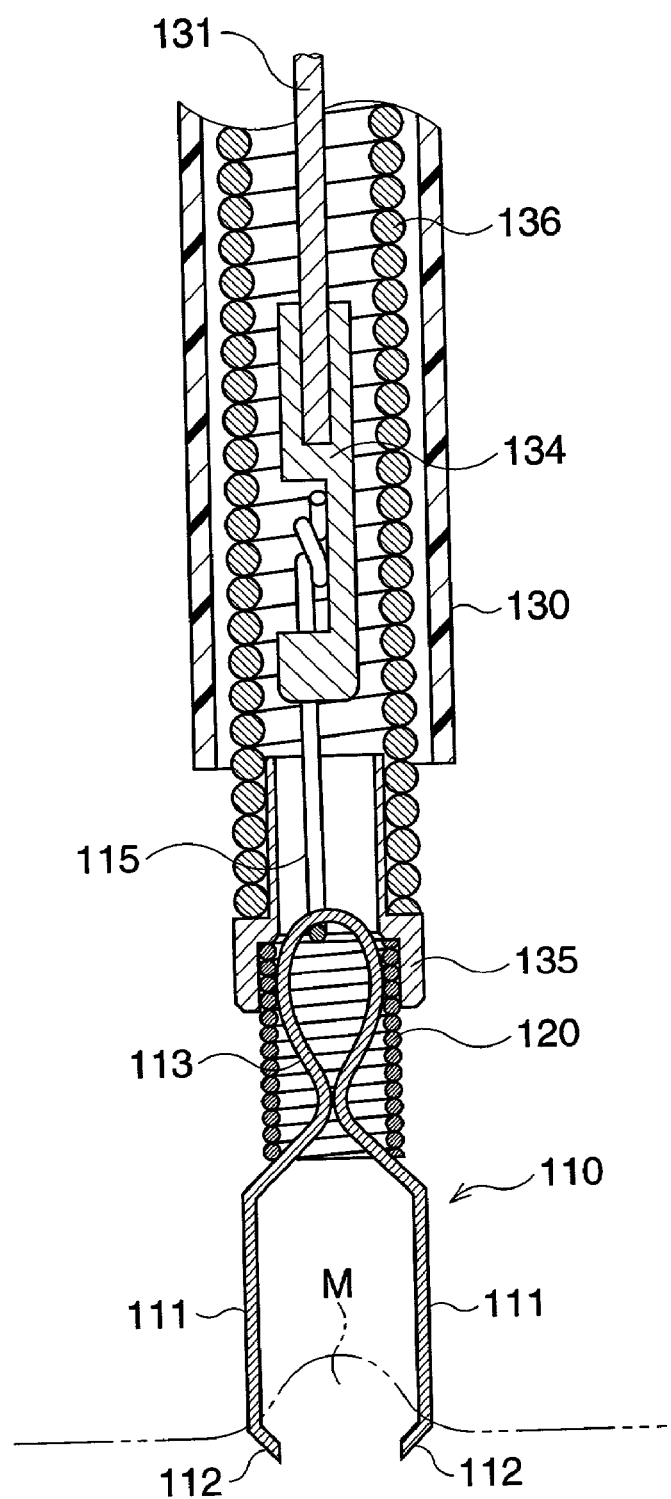
FIG. 48 is a longitudinal sectional view showing the distal end of the clip device, when the clip is closed, in the thirteenth embodiment.

While maintaining this condition, the distal end of the outer sheath 130 is positioned in such a manner that the diseased portion M lies between the arms 111. Then, when the operating wire 131 is further pulled toward the operating unit 140, the clip open-close ring 120 pushes the arms 111, so that the arms 111 become parallel to each other, and the claw portions 112 bite into the mucous membrane of the diseased portion M, as shown in FIG. 48.

Figure 49:
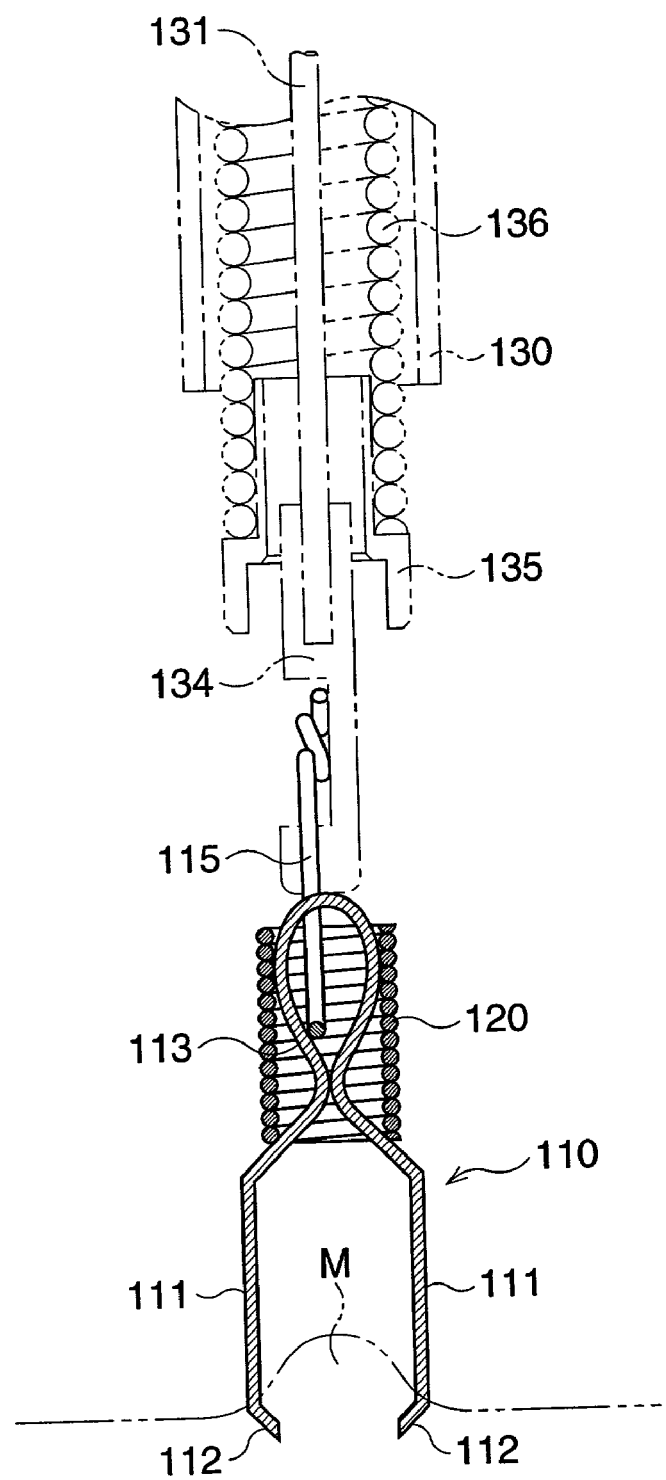
FIG. 49 is a longitudinal sectional view showing the clip when clamped.

Then, the outer sheath 130 is laterally moved while the operating wire 131 is slightly pushed to the distal end, so that the engagement between the clip connecting string 115 and the clip open-close hook 134 is loosened. Therefore, when the distal end of the outer sheath 130 is properly moved, the clip 110 is disengaged from the outer sheath 130 while biting into the mucous membrane of the diseased portion M. The clip is kept closed by the clip open-close ring 120. Thus, the clip 110 is clamped there as shown in FIG. 49.

As described above, according to the thirteenth embodiment, since the clip open-close ring 120 is formed from a flexible cylindrical body such as a coil pipe, the hard non-bending portion of the distal end of the clip device is shortened, and therefore, even when the treatment tool insert channel 150 is bent with a considerably small radius of curvature, the clip device can smoothly pass through the treatment tool insert channel 150 without being damaged.

Figure 50:
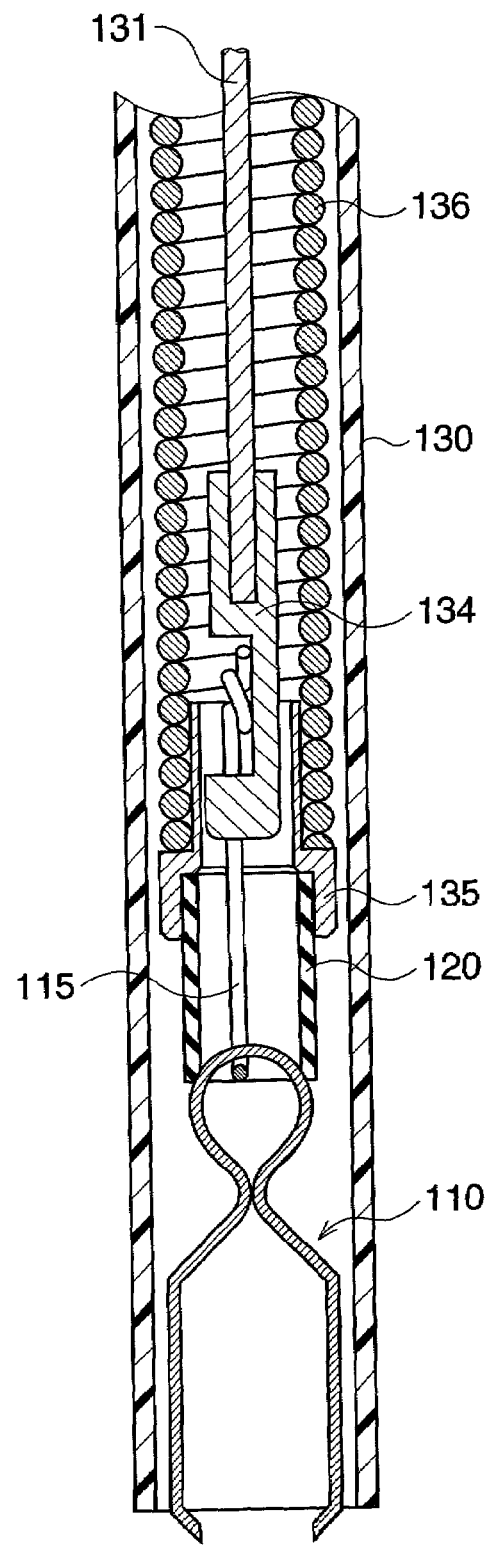
FIG. 50 is a longitudinal sectional view of a distal end of the clip device of a fourteenth embodiment.
Figure 51:
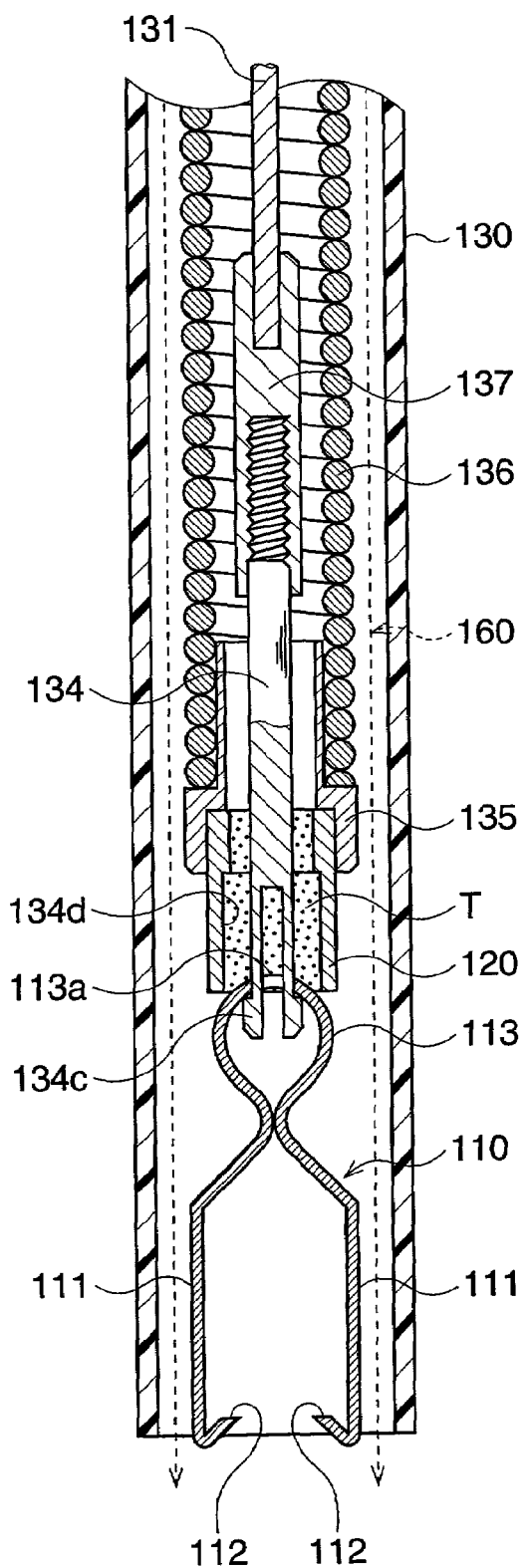
FIG. 51 is a longitudinal sectional view of a distal end of the clip device of a fifteenth embodiment.

FIG. 50 shows a fourteenth embodiment, in which the clip open-close ring 120 is a cylindrical body made of rubber having elasticity. According to this embodiment, the same effect as the thirteenth embodiment is obtained.

With reference to FIGS. 51 through 54, a fifteenth embodiment is described below. The general construction is basically the same as that shown in FIG. 1. In the drawings, the parts which correspond to those in the previously described embodiments are indicated by the same references.

Note that the basic construction of the fifteenth embodiment is the same as the eleventh embodiment shown in FIGS. 36 through 39, except that a water supply passage 160 is provided in the outer sheath 130 and a temporal-fixing agent is filled in the clip open-close ring 120. The other constructions are the same as those in the eleventh embodiment.

Water is supplied into the outer sheath 130 through a syringe, for example, attached to the water supply tube 133 (see FIG. 1). The base end cylinder 132 is sealed so that water supplied from the water supply tube 133 does not leak out through the base end cylinder 132.

A temporal-fixing agent T, composed of tackiness agent and so on, having a low tackiness, such as silicone system tackiness agent, is filled in the clip open-close ring 120. Due to this, the clip 110, the clip connecting hook 134, and the clip open-close ring 120 are integrally temporally fixed to each other.

The inner sheath 136 is loosely inserted in the outer sheath 130 over the whole length thereof. The space between the outer surface of the inner sheath 136 and the inner surface of the outer sheath 130 defines the water supply passage 160, through which water supplied from the water supply tube 133 passes.

The water supplied from the water supply tube 133 passes outside the clip open-close ring 120, and spouts out from the distal end of the outer sheath 130. At this time, since the water pressure does not act on the temporal-fixing agent T, the temporal fixing condition of the clip 110, the clip connecting hook 134, and the clip open-close ring 120 is not loosened.

The operation of the fifteenth embodiment is as follows. First, the outer sheath 130 is inserted into a treatment tool insert channel of an endoscope not shown, and while maintaining the state in which the clip 110 is projected from the outer sheath 130, the clip open-close ring 120 is pushed out toward the clip 110, by pulling the operating wire 131.

Figure 52:
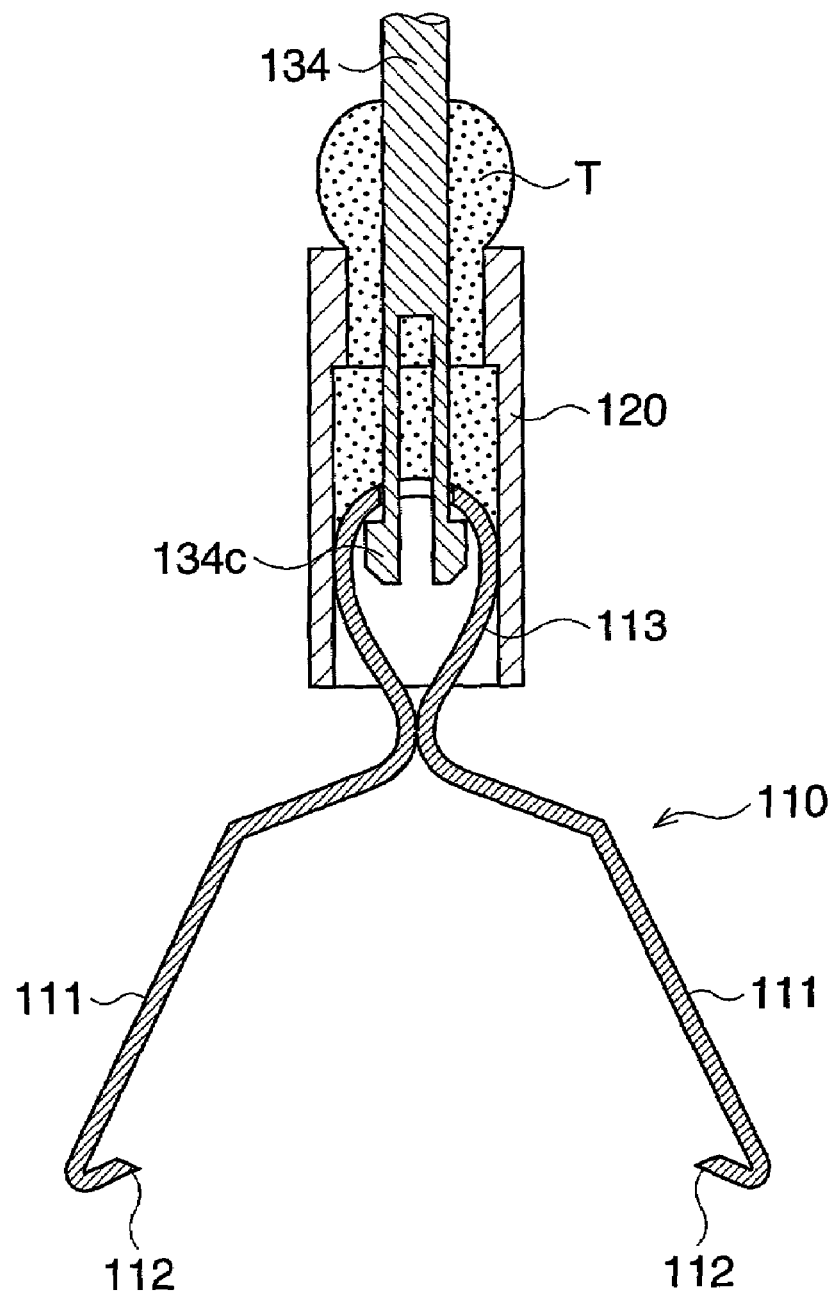
FIG. 52 is a longitudinal sectional view showing the distal end of the clip device when the clip is open, in the fifteenth embodiment.

As a result, as shown in FIG. 52, the base end portion 113 is pulled into the clip open-close ring 120, and deformed, so that the arms 111 are open. At the same time, the temporal-fixing agent T is pushed out, to some extent from the inside of the clip open-close ring 120.

While maintaining this condition, the distal end of the outer sheath 130 is positioned in such a manner that the diseased portion M lies between the arms 111. At this time, if the target diseased portion cannot be recognized visually because of bleeding and so on, irrigating water is supplied through the water supply tube 133, while directing the distal end of the outer sheath 130 to the target. Thus, the irrigating water spouts out from the outer sheath 130, so that the blood and so on can be washed away while maintaining the state in which the clip 110 is temporarily fixed to the clip connecting hook 134, and the clip open-close ring 120.

Figure 53:
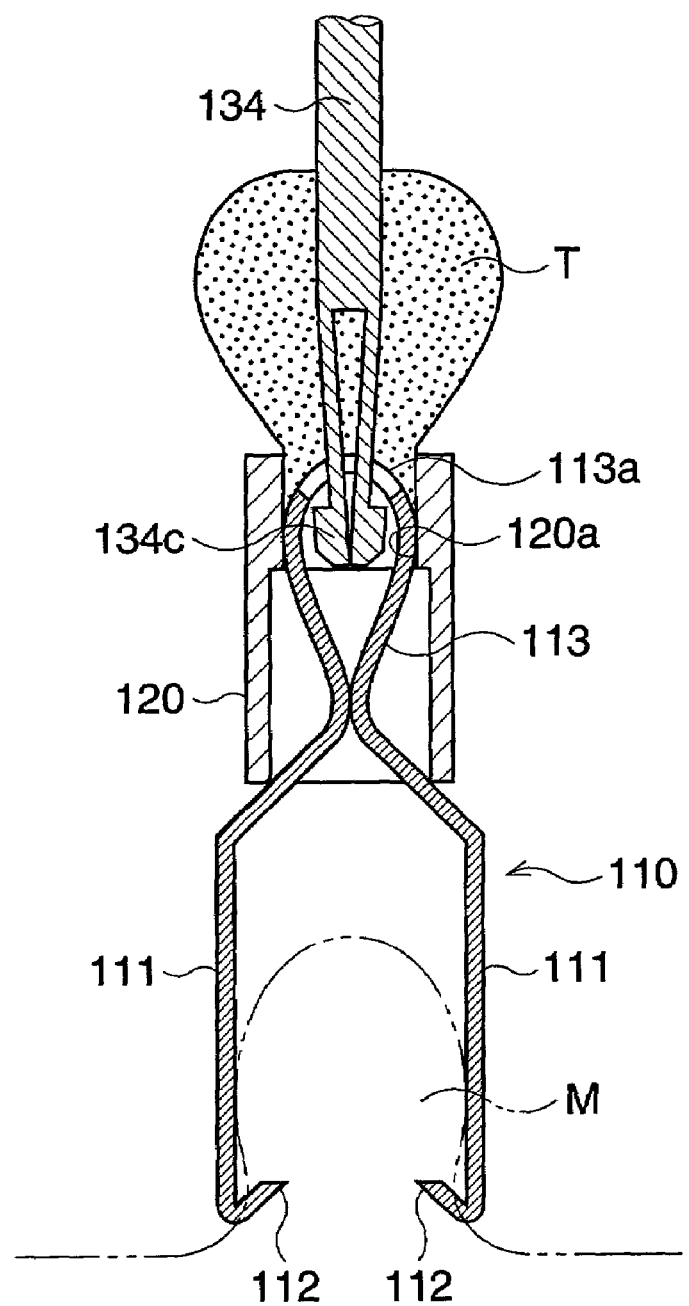
FIG. 53 is a longitudinal sectional view showing the distal end of the clip device, when the clip is closed, in the fifteenth embodiment.

Then, when the clip open-close ring 120 is pushed out toward the clip 110, as shown in FIG. 53, the base end portion 113 is further deformed, and the tip of the clip open-close ring 120 presses the rear surfaces of the arms 111. Due to this, almost all of the temporal-fixing agent T is pushed out from the clip open-close ring 120, and the arms 111 become parallel to each other, so that the claw portions 112 bite into the mucous membrane of the diseased portion M.

The base end portion 113 of the clip 110 is fit in the base end portion 120a of the clip open-close ring 120, and is squeezed or deformed by the clip open-close ring 120. Due to this, the clip connecting hook 134 is pressed, so that the clip connecting hook 134 can pass through the connecting hole 113a.

Figure 54:
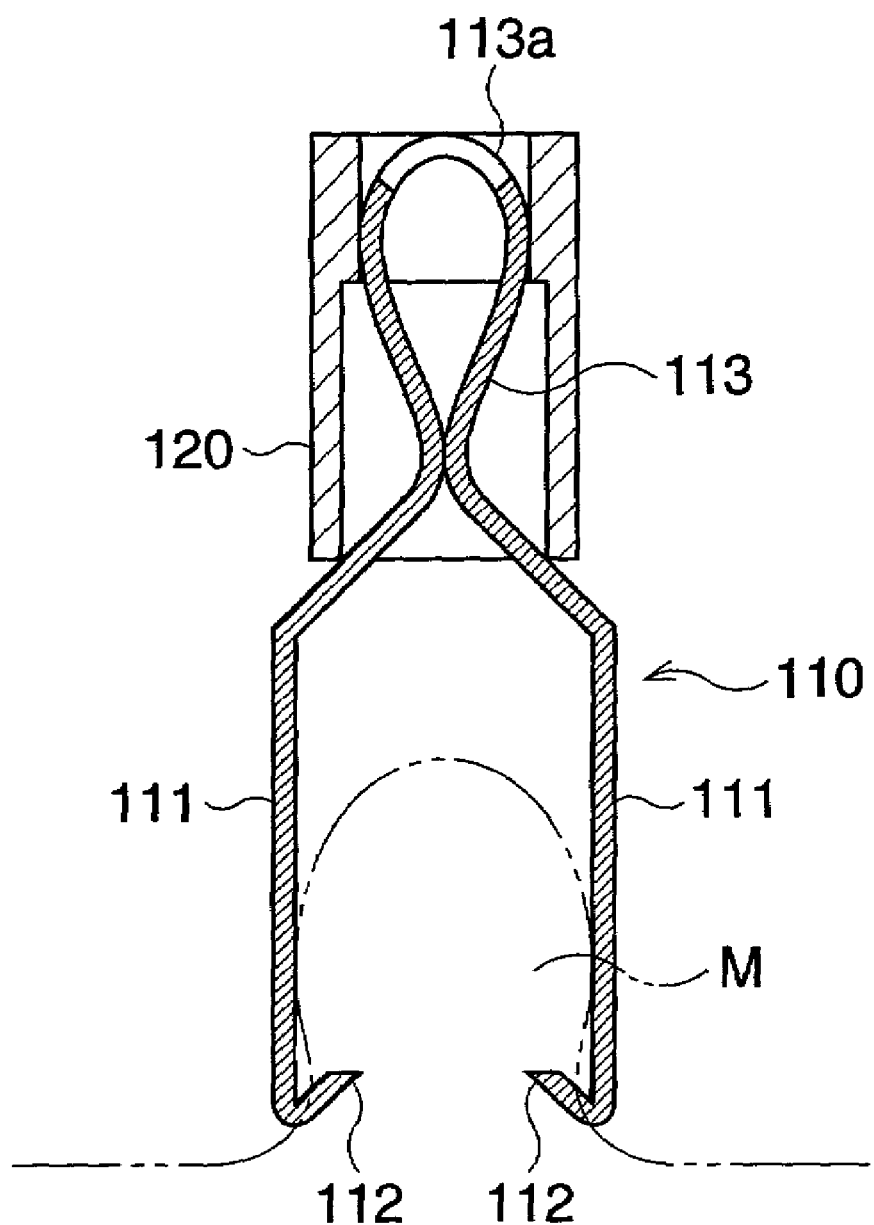
FIG. 54 is a longitudinal sectional view showing the clip when clamped.

Thus, the clip connecting hook 134 is released from the clip 110, and the outer sheath 130 is removed from the diseased portion M. Thus, as shown in FIG. 54, the clip 110 to which the clip open-close ring 120 is attached, is clamped to the mucous membrane of the diseased portion M.

As described above, according to the fifteenth embodiment, the water supply passage 160 is formed in such a manner that the water supply passage 160 does not interfere with the temporal-fixing agent T. Accordingly, water is supplied from the distal end of the outer sheath 130 to perform irrigation of the bleeding are and to aid clamping, without shaking the clip 110, which is temporarily fixed with the temporal-fixing agent T.

Figure 55:
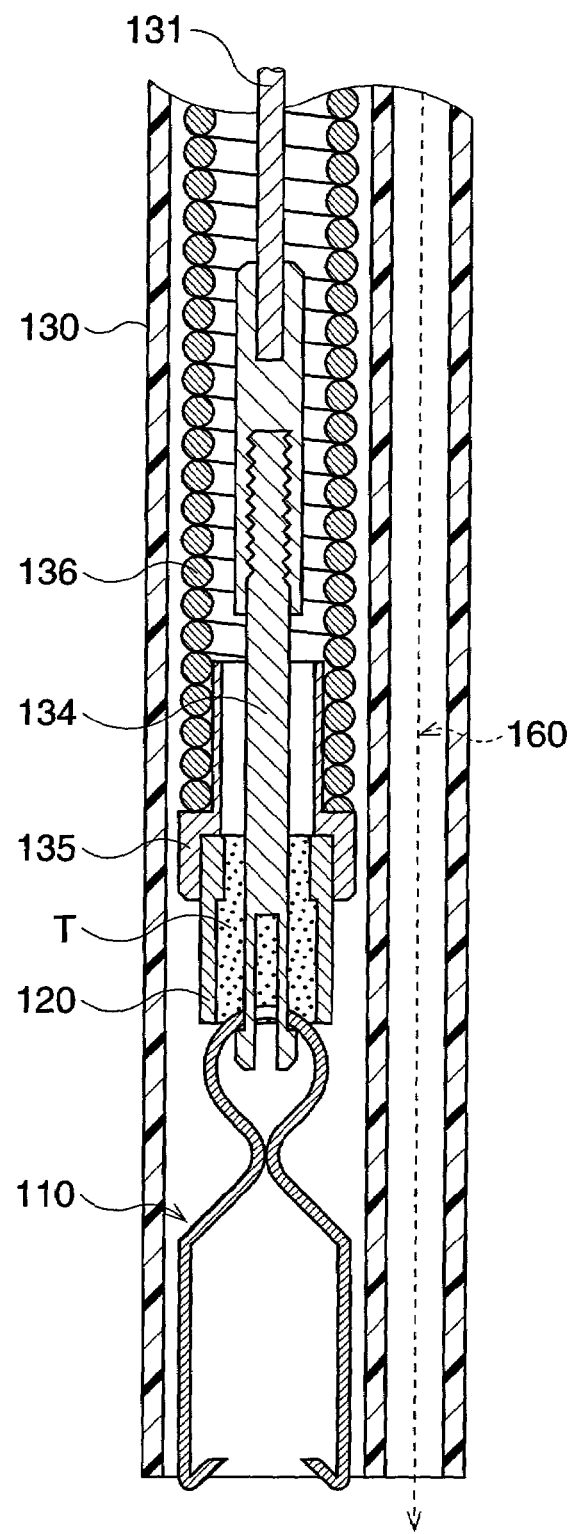
FIG. 55 is a longitudinal sectional view of a distal end of the clip device of a sixteenth embodiment.

FIG. 55 shows a sixteenth embodiment, in which the outer sheath 130 is a so called multi-lumen tube. Namely, the outer sheath 130 is divided into two parts, and one of the parts is the water supply passage 160, while the inner sheath 136, and the other elements are housed in another part.

Figure 56:
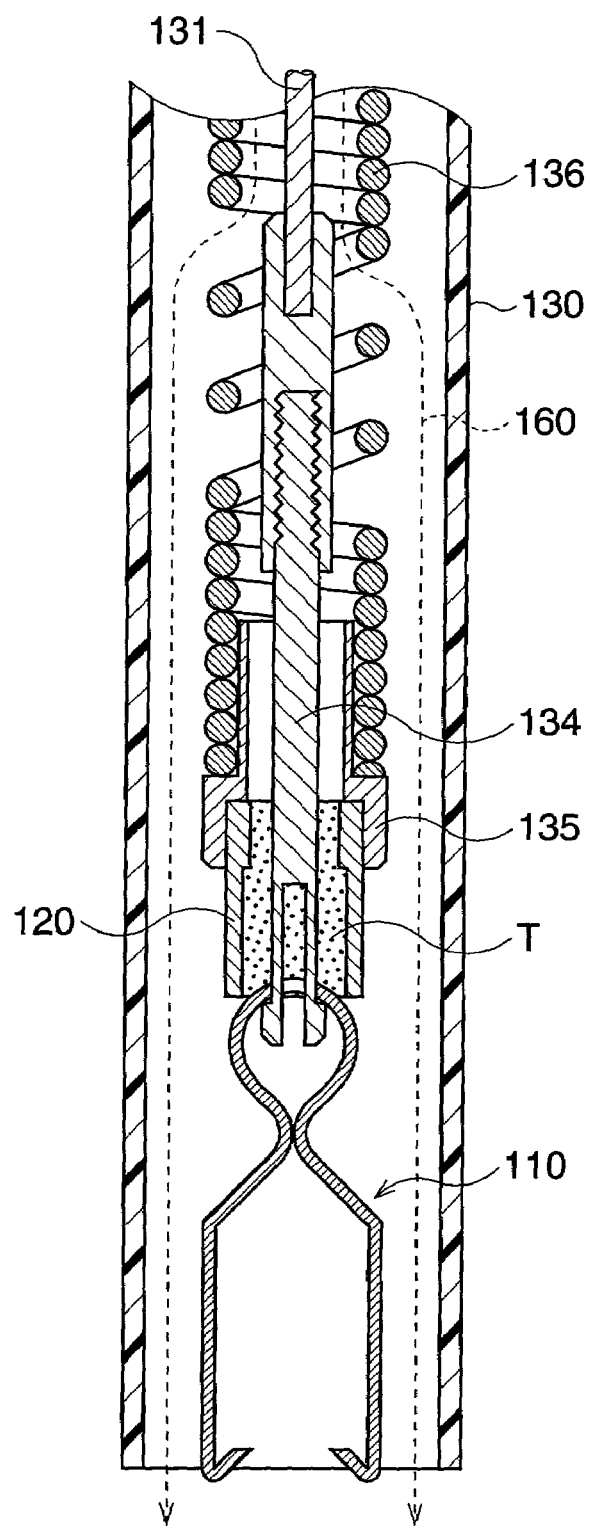
FIG. 56 is a longitudinal sectional view of a distal end of the clip device of a seventeenth embodiment.

FIG. 56 shows a seventeenth embodiment, in which the pitch of a part of the coil of the clip open-close ring 120 is made coarser at a portion close to the distal end of the inner sheath 136, in comparison with the other part, so that the water supply passage 160 is formed.

Figure 57:
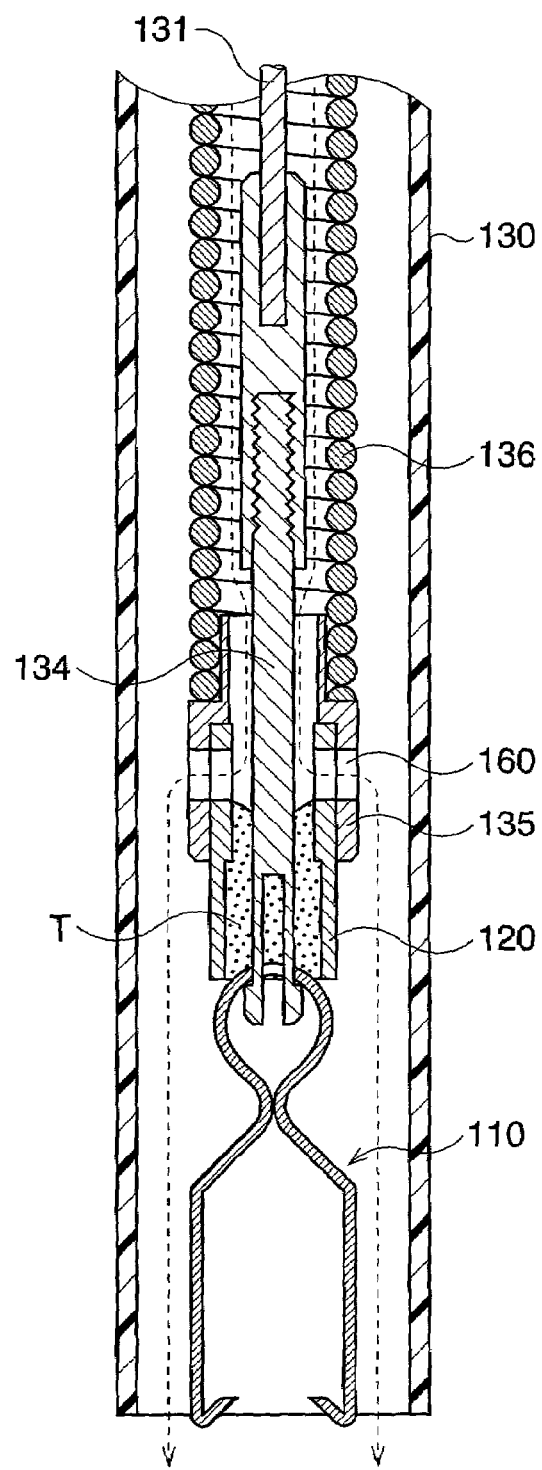
FIG. 57 is a longitudinal sectional view of a distal end of the clip device of an eighteenth embodiment.

FIG. 57 shows an eighteenth embodiment, in which a hole is formed in each of the clip open-close ring 120 and the ring receiving cylinder 135 to enable communication between the inside of the clip open-close ring 120 and the ring receiving cylinder 135, and the outside of the clip open-close ring 120 and the ring receiving cylinder 135. Thus, the hole is the water supply passage 160, through which water passing through the inner sheath 136 is supplied to the outside of the clip open-close ring 120 and is spouted out from the distal end of the outer sheath 130.

Figure 58:
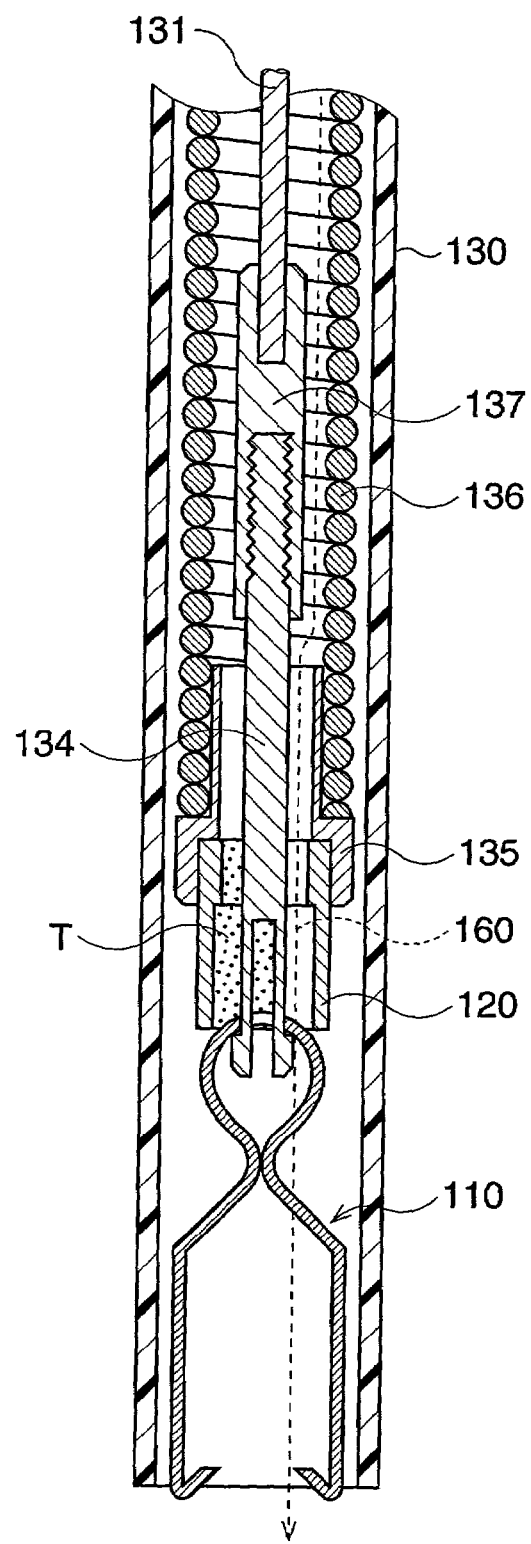
FIG. 58 is a longitudinal sectional view of a distal end of the clip device of a nineteenth embodiment.

FIG. 58 shows a nineteenth embodiment, in which the clip open-close ring 120 is formed with a passage in which the temporal-fixing agent T is not filled, the passage functions as the water supply passage 160. In this embodiment, the irrigating water supplied is spouted out from the outer sheath 130, while the temporal-fixing agent T is kept in the clip open-close ring 120.

As described above, according to the sixteenth through nineteenth embodiments, the same effect as the fifteenth embodiment is obtained.

With reference to FIGS. 59 through 64, a twentieth embodiment is described below. The general construction of the clip device is basically the same as that shown in FIG. 1. In the drawings, the parts which correspond to those in the previously described embodiments are indicated by the same references.

Figure 59:
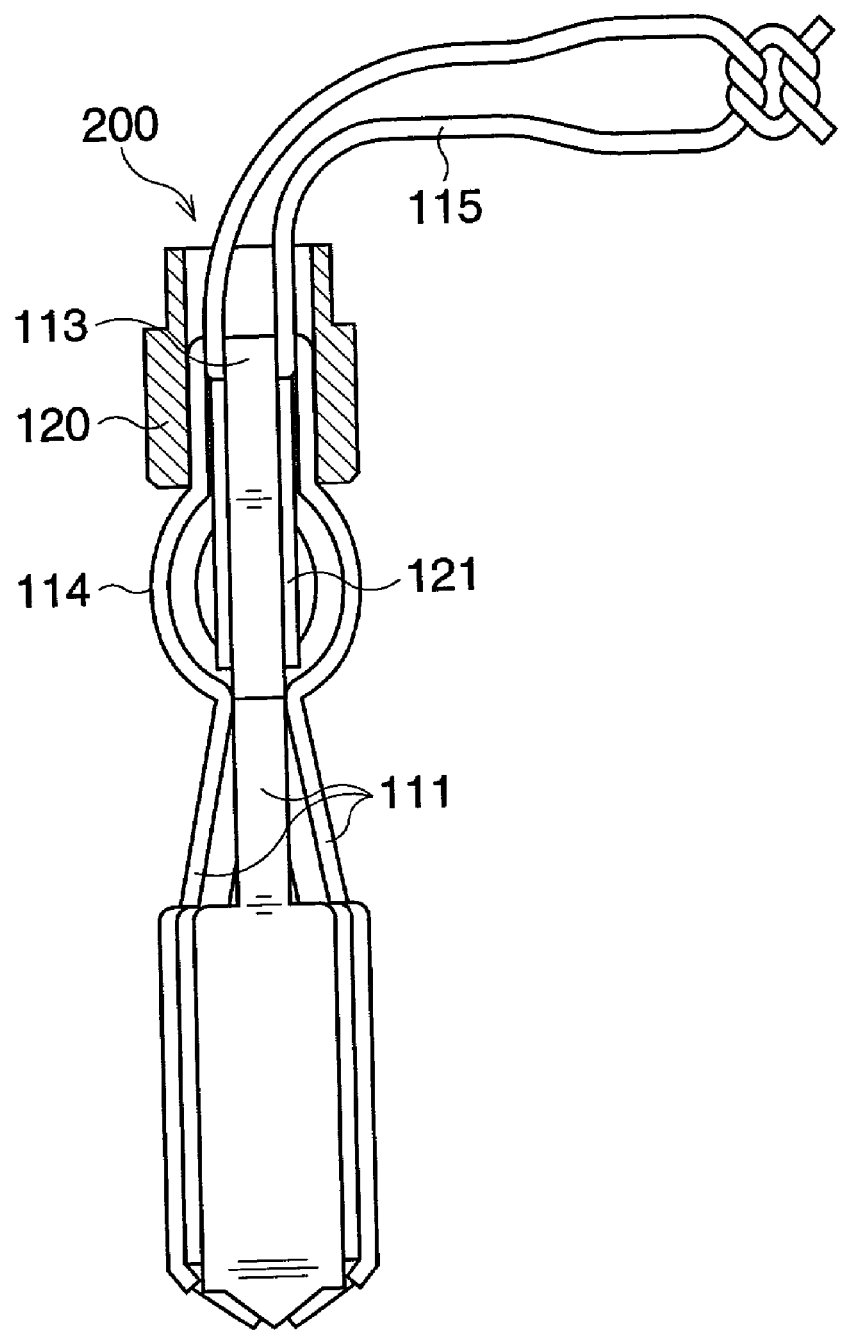
FIG. 59 is a partially sectional plan view of the clip unit of a twentieth embodiment.

FIG. 59 shows a clip unit 200, which has the clip 120, the clip open-close ring 120, the clip connecting string 115, and the core member 121. The construction of the clip unit 200 is identical with that of the first embodiment shown in FIG. 5.

Figure 60:
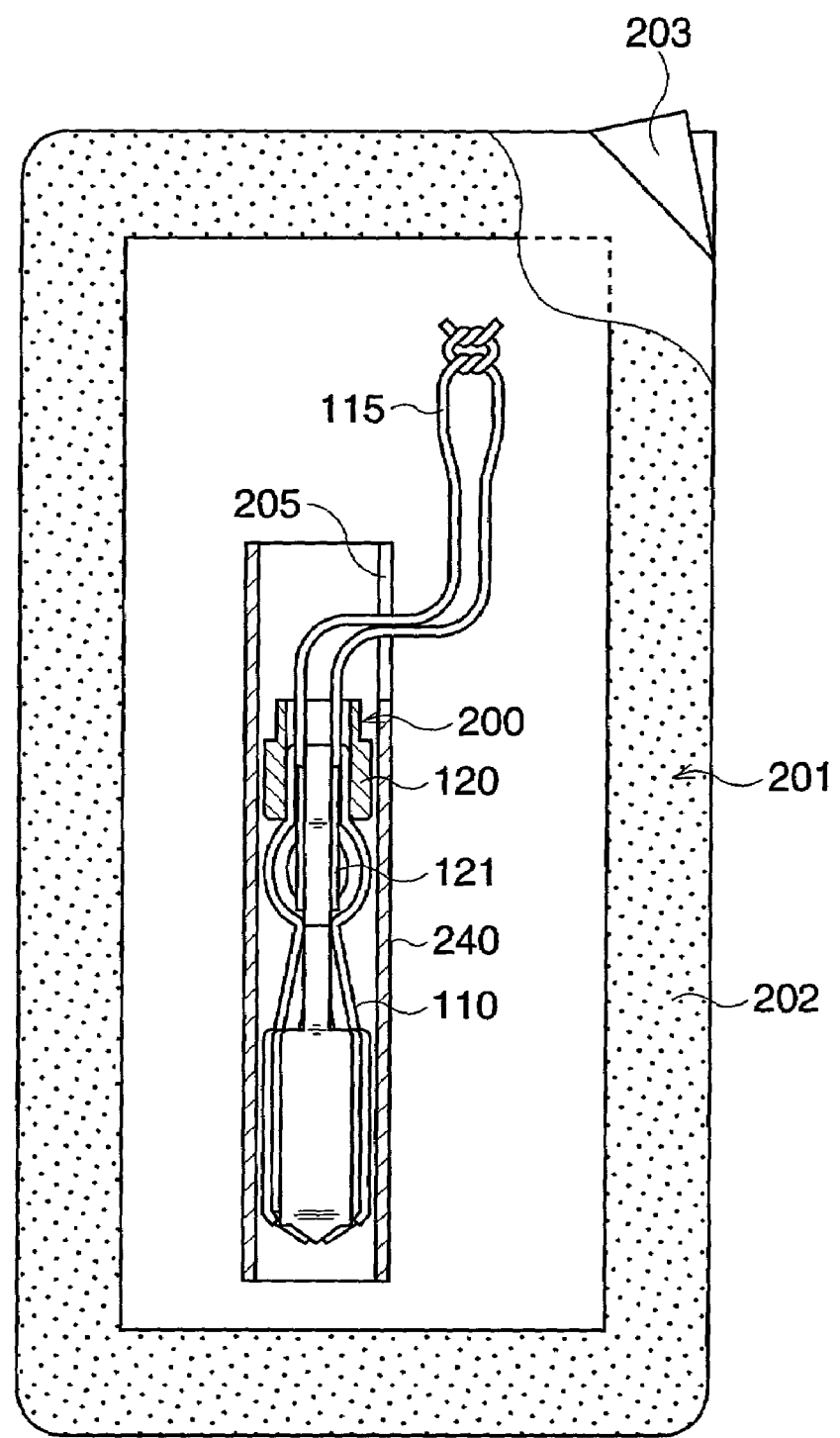
FIG. 60 is a partially sectional plan view of the clip unit enclosed in a sterile pack.

When the clip unit 200 is shipped to a user, the clip unit 200 is enclosed in a sterile pack 201, which is sealed along an enclosed portion 202 provided along the outer periphery of the sterile pack 201, as shown in FIG. 60. The enclosed portion 202 is easily opened at an easy open flap 203 at a corner of the sterile pack 201. In the sterile pack 201, the clip unit 200 is housed in a preserving member 204, which is a cylindrical member made of synthetic resin such as tetrafluoroethylene resin, or metal, and the clip unit 200 and the preserve member 204 have been sterilized.

Therefore, the clip unit 200 enclosed in the sterile pack 201 is not deformed nor damaged even if they are handled carelessly. The preserve member 204 has a slit 205, and the clip connecting string 115 extends to the outside of the preserve member 204, being sandwiched by the slit 205.

Figure 61:
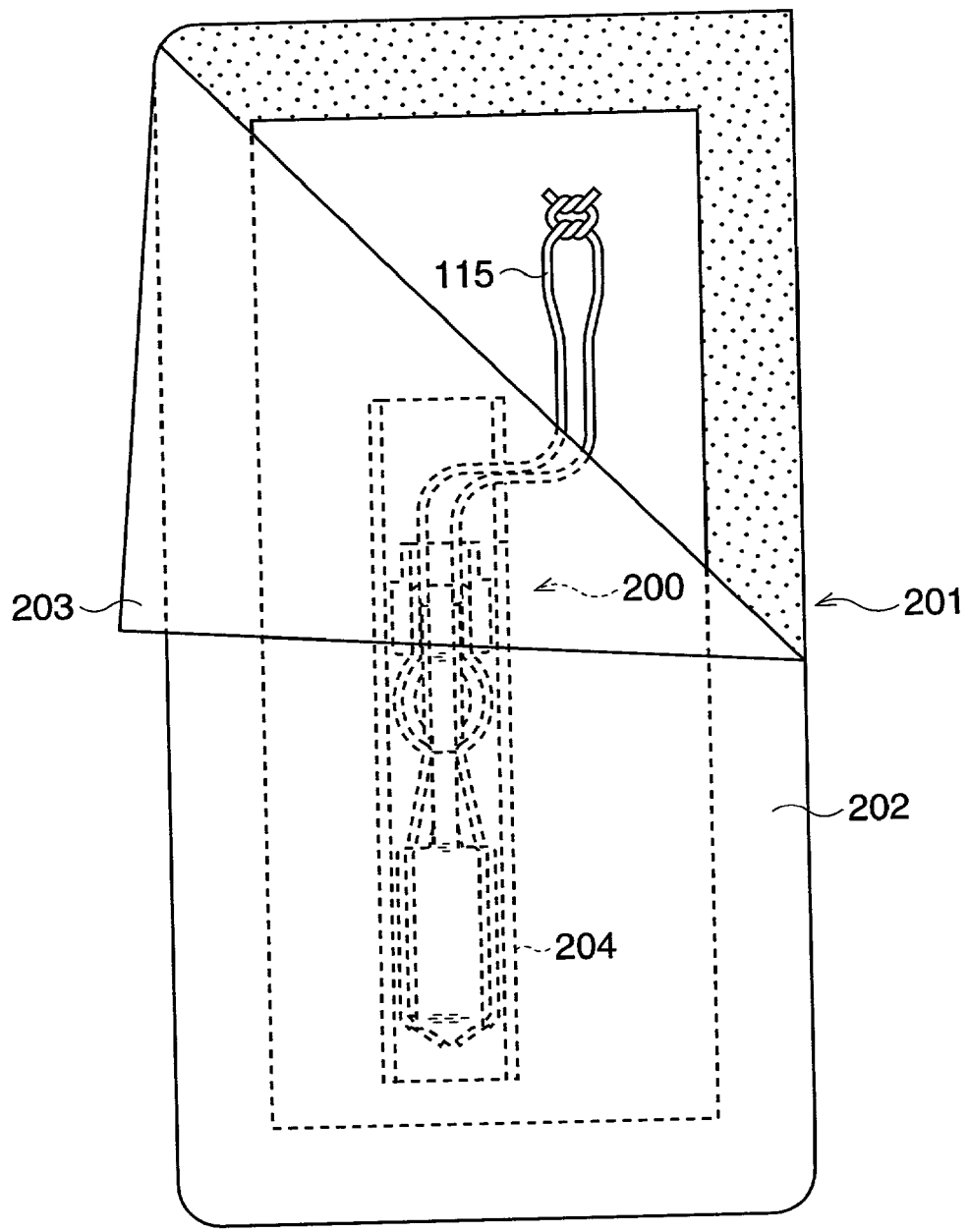
FIG. 61 is a plan view showing that the sterile pack is partially open.
Figure 62:
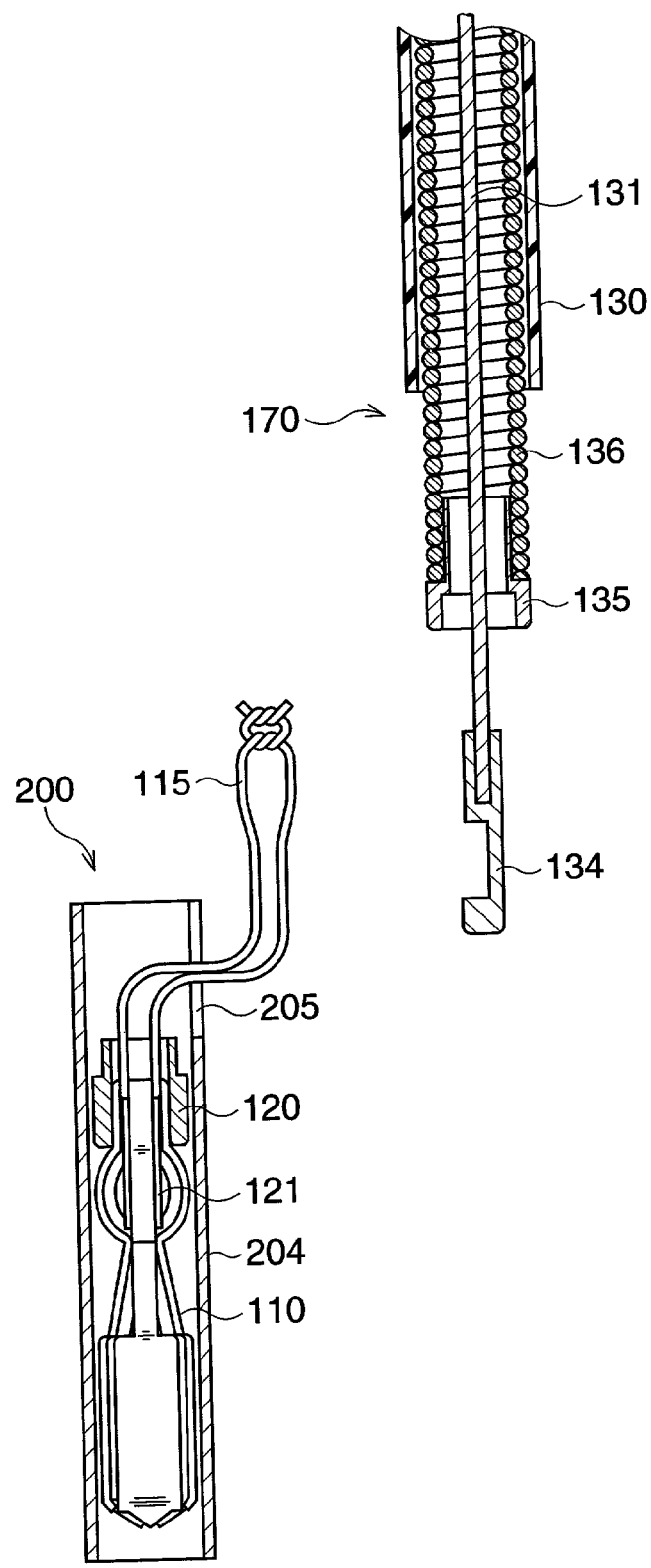
FIG. 62 is a longitudinal sectional view showing the clip unit before it is connected to a sheath unit.

When the clip unit 200, enclosed in the sterile pack 201, is to be used, as shown in FIG. 61, the easy open flap 203 is pealed back by the fingers to open the sterile pack 201. Then, the clip unit 200 housed in the preserve member 204 is taken out of the sterile pack 201, and the clip connecting string 115 extending through the slit 205 is engaged with the clip connecting hook 134 provided to a sheath portion 170, as shown in FIG. 62.

The sheath portion 170 is constructed in such a manner that the inner sheath 136 is inserted or disposed in the flexible outer sheath 130, which is formed with roughly the same diameter as that of the preserve member 204, and the clip connecting string 115 is connected to the tip portion of the operating wire 131. The ring receiving cylinder 135 for receiving the clip open-close ring 120 is attached to the distal end of the inner sheath 136.

Figure 63:
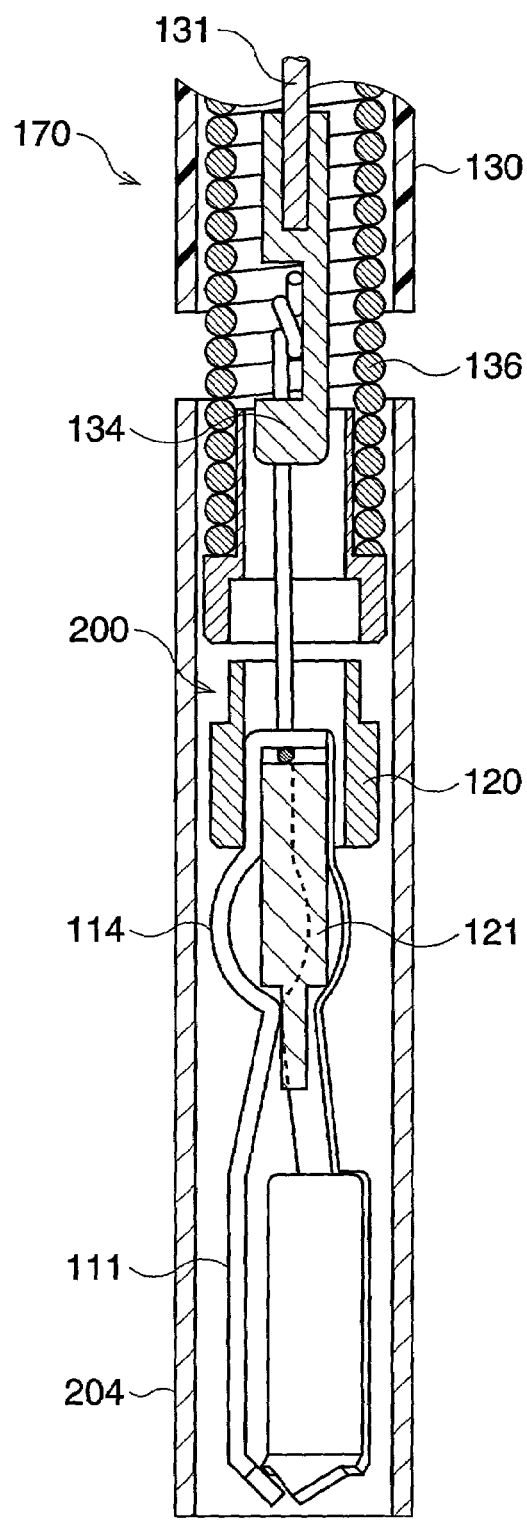
FIG. 63 is a longitudinal sectional view showing an operation in which the clip unit is being connected to the sheath unit.

Then, as shown in FIG. 63, the operating wire 131 is pulled into the inner sheath 136 by an operation performed with the operating unit 140 (see FIG. 1), and at the same time, the preserve member 204 is fit to the outside of the inner sheath 136.

Figure 64:
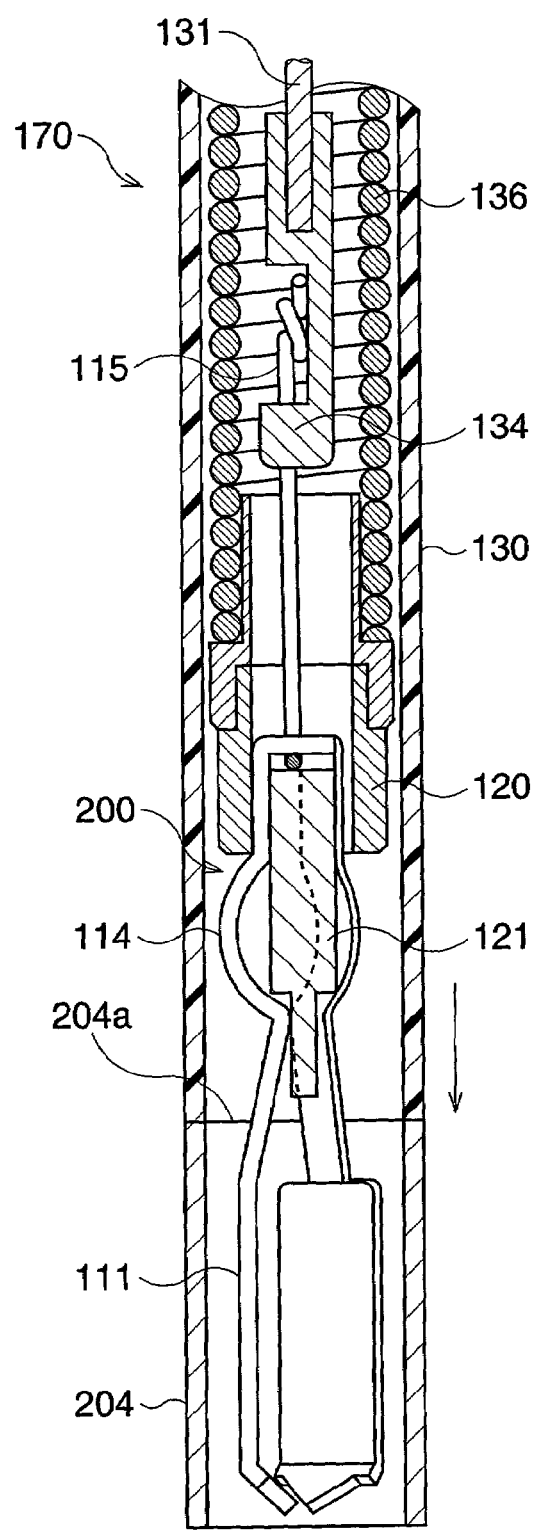
FIG. 64 is a longitudinal sectional view showing an operation in which the clip unit is being connected to the sheath unit, after the state shown in FIG. 63.

After this, as shown in FIG. 64, when the outer sheath 130 is moved forward (downward in the drawing), the preserve member 204 is pushed out by the outer sheath 130 to move relative to the clip unit 200 along the axial direction of the preserve member 204 and disengage from the clip 110, so that the clip 110 is set to a usable state. Thus, the preserve member 204 may have an opening at least at an upper end 204a.

According to the twentieth embodiment, the clip unit 200 is housed in the preserve member 204, and is enclosed in the sterile pack 201, which can be opened using the easy open flap 203. Therefore, the clip unit 200 cannot be deformed until the clip unit 200 is attached to the sheath portion 170, even if the clip unit 200 enclosed in the sterile pack 201 is carelessly handled. Namely, the clip unit 200 can be used when it is needed.

With reference to FIGS. 65 through 70, a twenty-first embodiment is described below. The general construction of the clip device is basically the same as that of the tenth embodiment shown in FIGS. 32 through 35, except for the outer sheath 130. In the drawings, the parts which correspond to those in the previously described embodiments are indicated by the same references.

Figure 65:
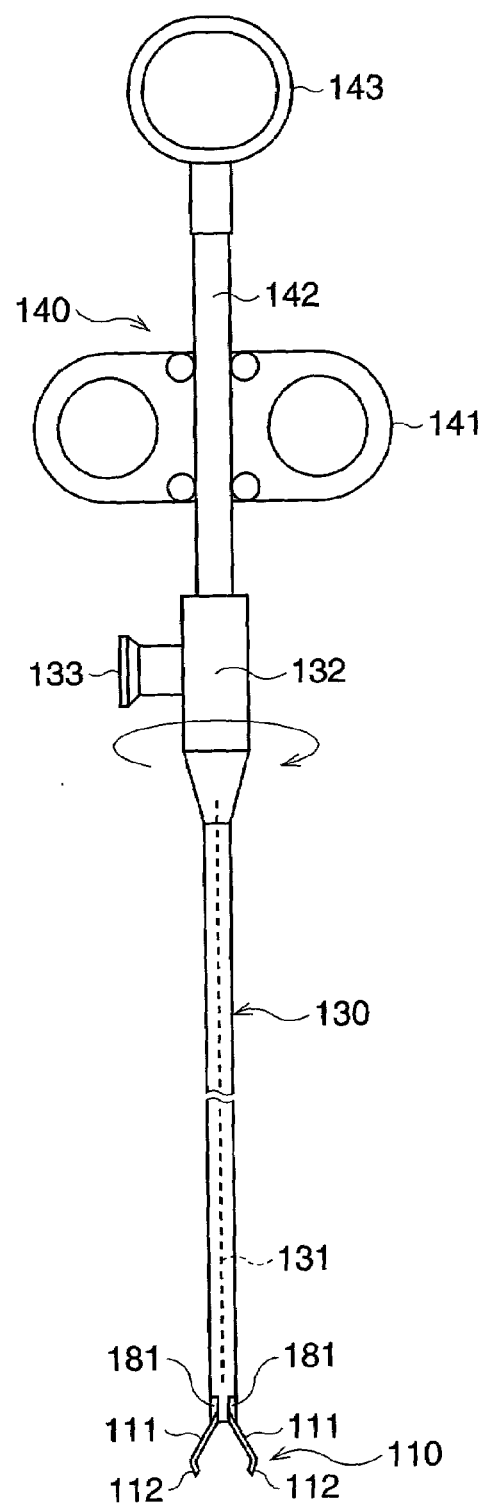
FIG. 65 is an external view showing a general construction of the clip device of a twenty-first embodiment.

FIG. 65 shows a general construction of the clip device of the twenty-first embodiment, which is basically the same as that of the first embodiment shown in FIG. 1, except that notches 181 are formed at the distal end of the outer sheath 130. The notches 181 open to the distal end of the outer sheath 130 so that the arms 111 of the clip 110 can be open and closed.

The outer sheath 130 can be rotated about the axis thereof, while the arms 111 are engaged with the notches 181. Namely, the clip 110 can be rotated about the axis by rotating the outer sheath 130, and the arms 111 are open and closed by moving the outer sheath 130 along the axis relative to the slider 141.

Figure 66:
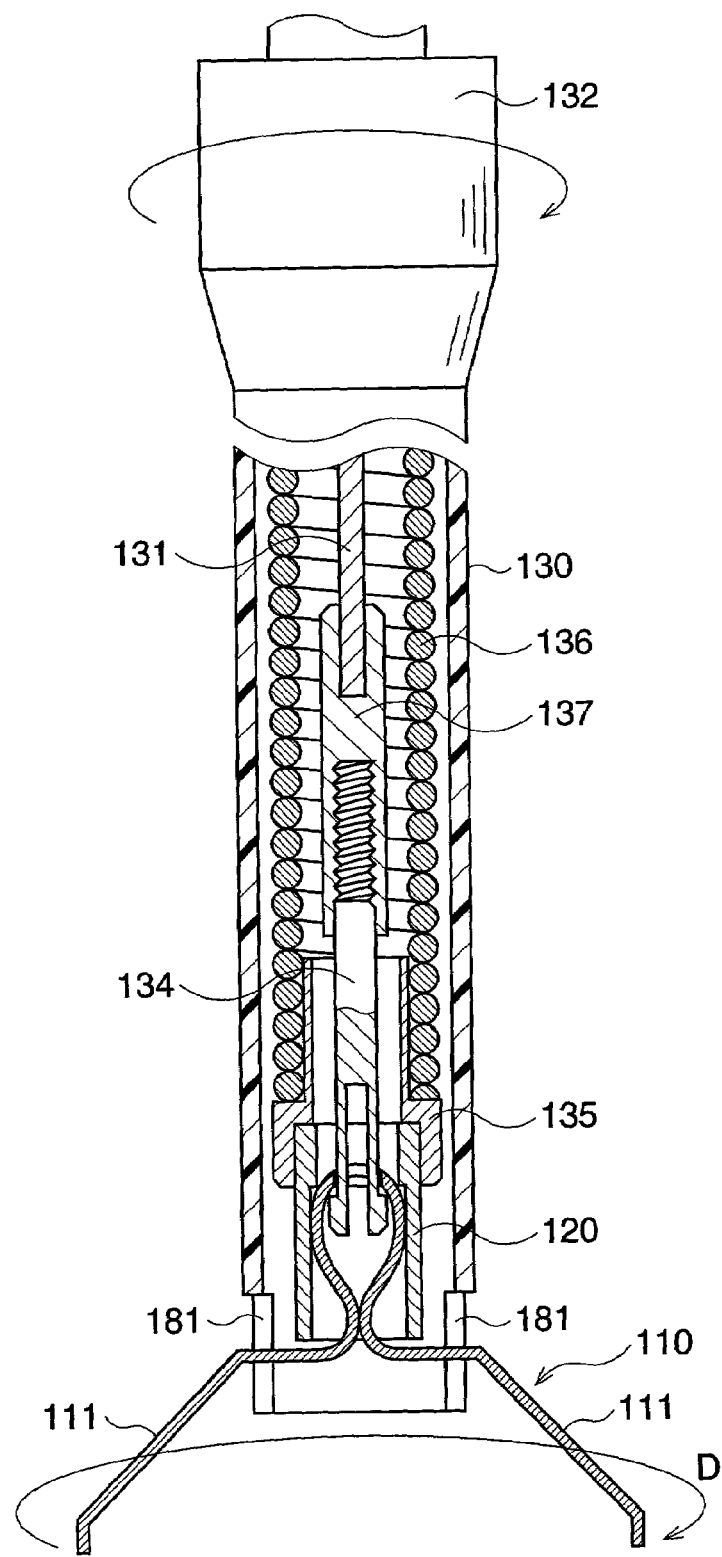
FIG. 66 is a longitudinal sectional view of a distal end of the clip device, when the clip is open and engaged with notches, in the twenty-first embodiment.
Figure 67:
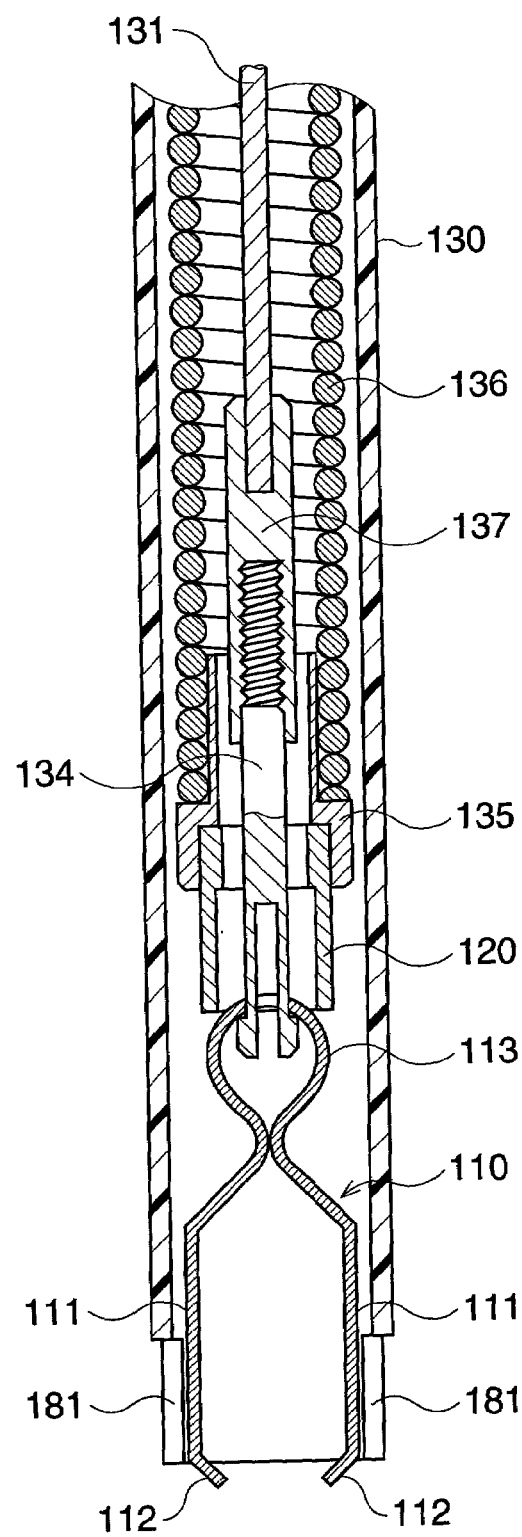
FIG. 67 is a longitudinal sectional view of the distal end of the clip device, when the clip is closed, in the twenty-first embodiment.

FIG. 66 shows a distal end of the clip device. The construction of the distal end is basically the same as that in the tenth embodiment shown in FIG. 32, except for the notches 181. In the drawing, the arms 111 are open, and no external force applies on the arms 111.

The operation of the twenty-first embodiment is as follows. First, the outer sheath 130 is inserted into a treatment tool insert channel of an endoscope not shown, while keeping the state shown in FIG. 67, in which the arms 111 are housed in the outer sheath 130 and closed. Then, the outer sheath 130 is pulled to the operating unit 140, so that the clip 110 is projected from the outer sheath 130, and the operating wire 131 is pulled to the operating unit 140. As a result, as shown in FIG. 68, the base end portion 113 of the clip 110 is pulled into the clip open-close ring 120, so that the base end portion 113 is deformed to open the arms 111.

Figure 69:
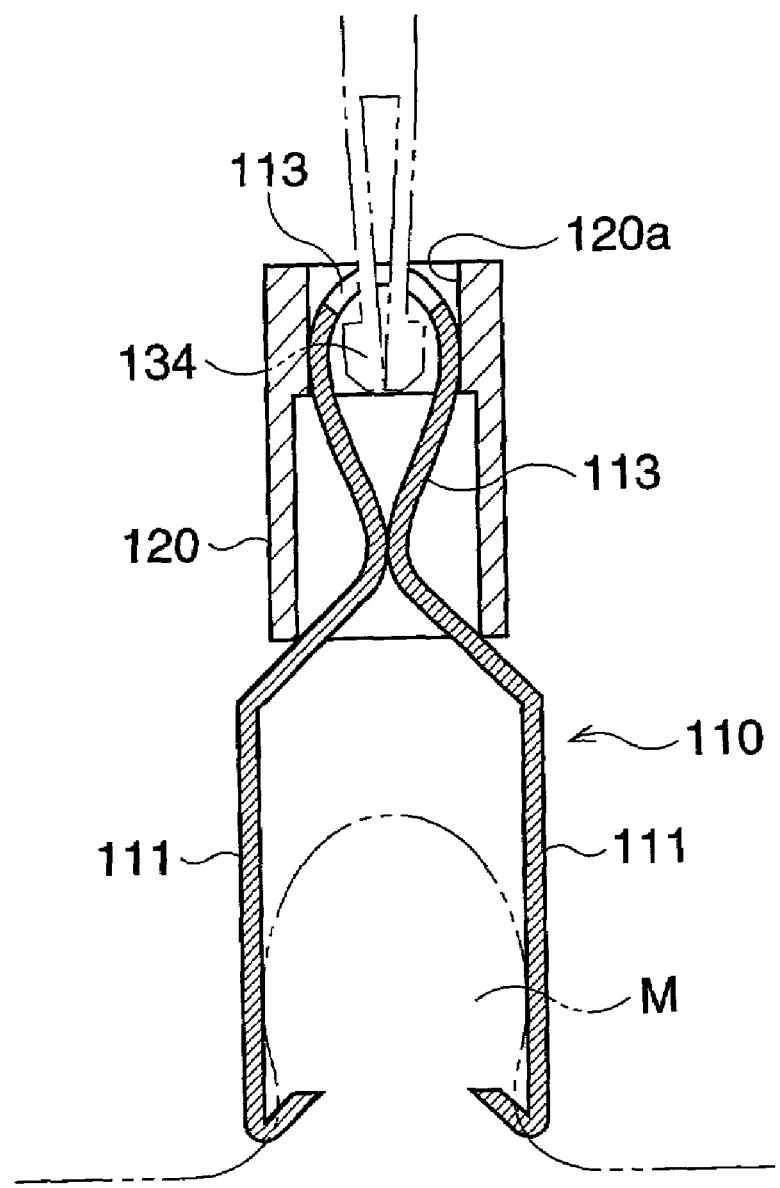
FIG. 69 is a longitudinal sectional view showing the clip when clamped, in the twenty-first embodiment.

Maintaining this condition, the distal end of the outer sheath 130 is positioned in such a manner that the diseased portion M lies between the arms 111, and the operating wire 131 is then further pulled to the operating unit 140. Due to this, as shown in FIG. 69, the tip portion of the clip open-close ring 120 presses the arms 111 while the base end portion 113 is further deformed, so that the arms 111 become parallel to each other, and the claw portions 112 bite into the mucous membrane of the diseased portion M.

The base end portion 113 of the clip 110 is fit in the base end portion 120a of the clip open-close ring 120, and is squeezed or deformed by the clip open-close ring 120, so that the clip connecting hook 134 can be released from the clip 110. Thus, the clip 110 is clamped to the mucous membrane of the diseased portion M.

Figure 68:
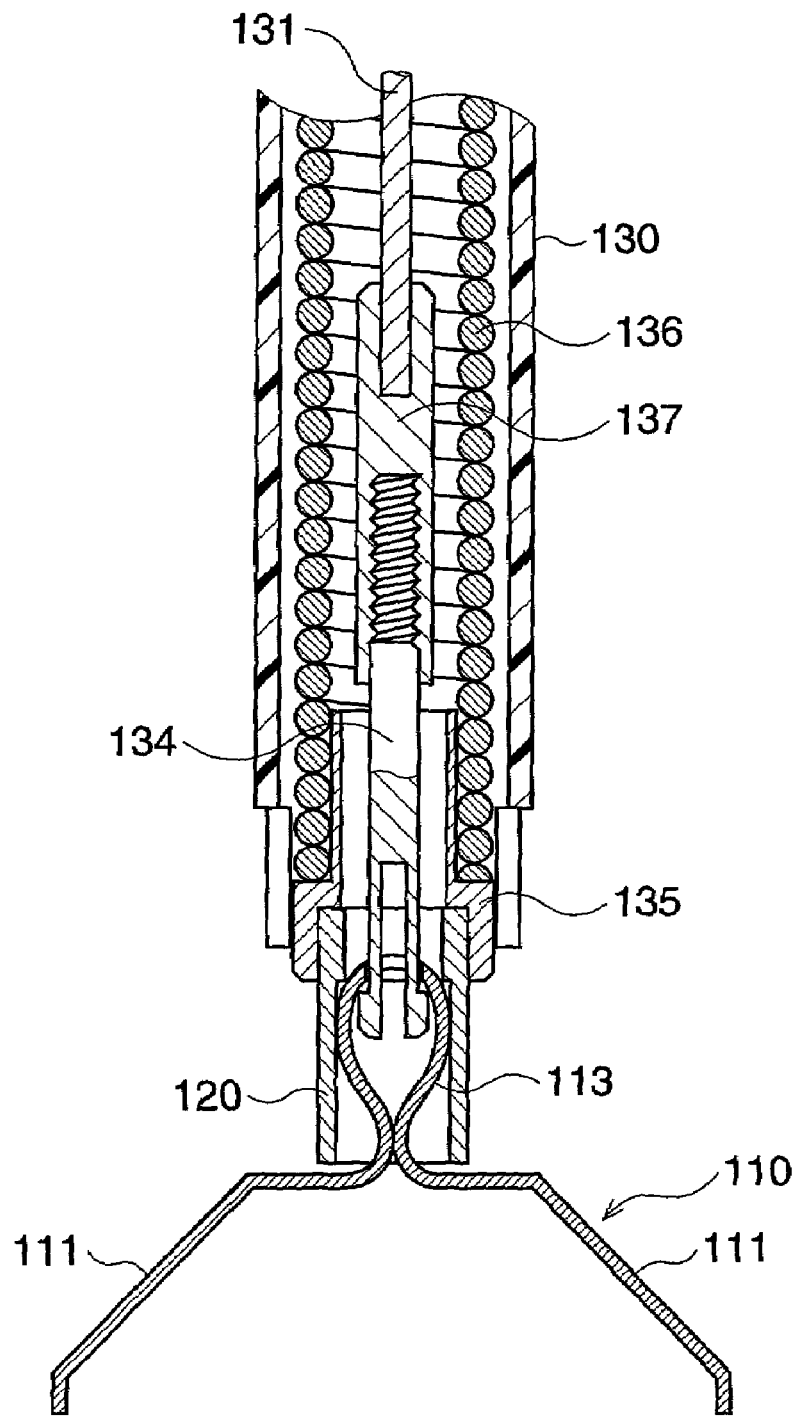
FIG. 68 is a longitudinal sectional view of the distal end of the clip device, when the clip is open, in the twenty-first embodiment.
Figure 70:
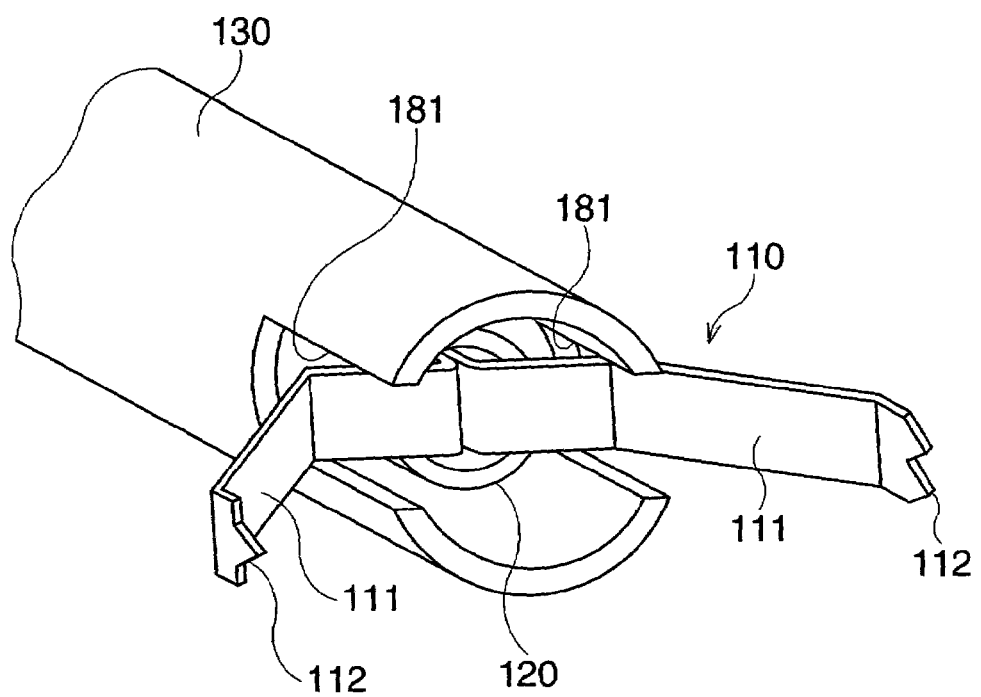
FIG. 70 is a perspective view showing the distal end of the clip device of the twenty-first embodiment.

In the clipping operation described above, if the rotational position of the clip 110 about the axis is to be changed when the clip 110 is open as shown in FIG. 68, the outer sheath 130 is moved toward the distal end relative to the inner sheath 136. Thus, the notches 181 formed on the distal end of the outer sheath 130 are engaged with the arms 111 of the clip 110 as shown in FIG. 70. The base end cylinder 132 or the outer sheath 130 is then rotated as shown in FIGS. 65 and 66, so that the clip 110, engaged with the notches 181, is rotated about the axis as shown by the arrow D in FIG. 66.

The ability of the outer sheath 130 to rotate the clip is superior to that of a wire and so on. Therefore, even when the inner sheath 136 is bent, the rotational movement of the base end cylinder 132 is transmitted to the notches 181.

Therefore, in any conditions, the angular position of the clip 110 about the axis can be controlled arbitrarily, so that the clip 110 can be set to the most preferable direction to bite into the diseased portion T. Further, by engaging the notches 181 with the clip 110, the clip 110 is prevented from rotating accidentally.

Figure 71:
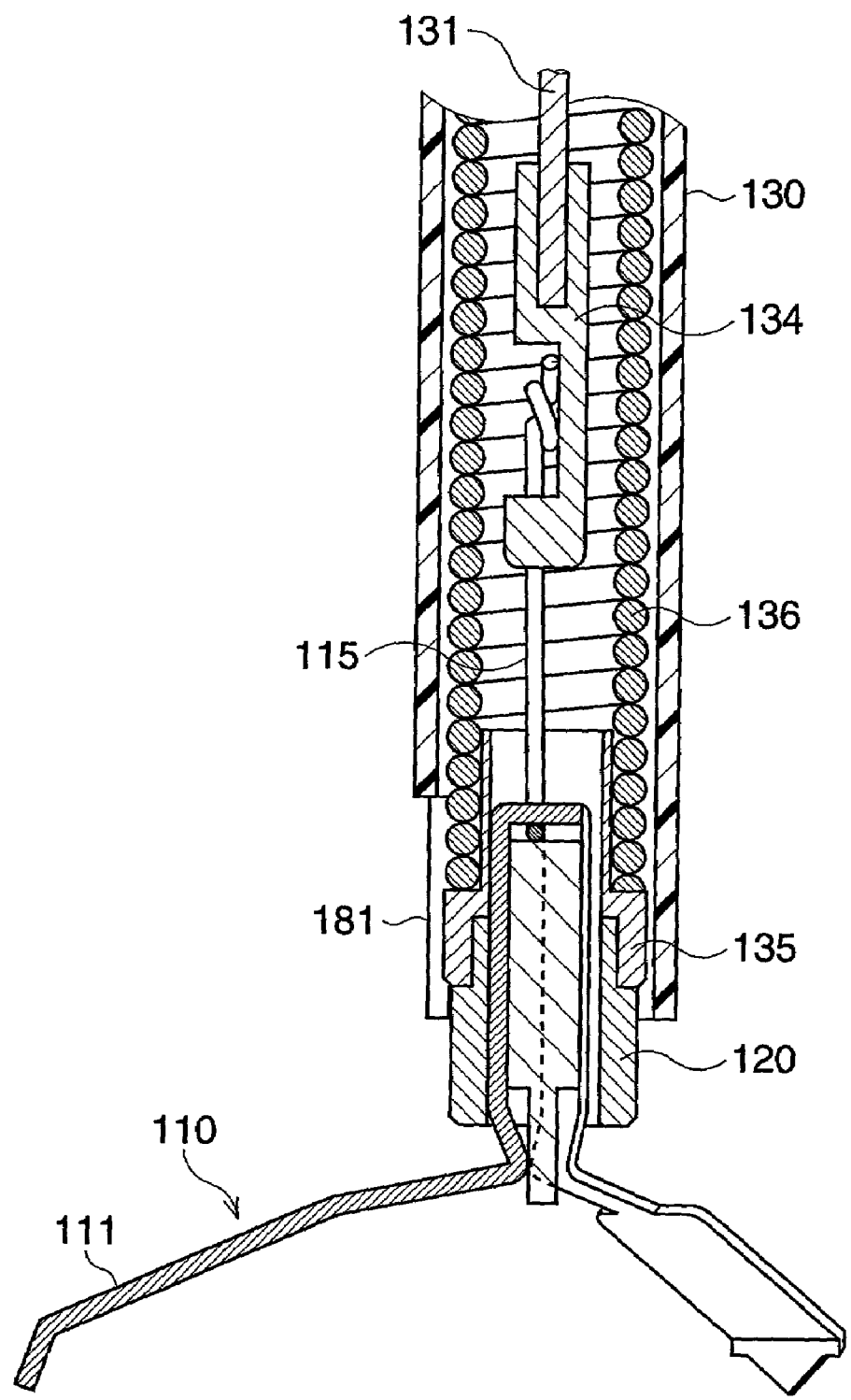
FIG. 71 is a longitudinal sectional view of the distal end of the clip device, when the clip is open, in a twenty-second embodiment.
Figure 72:
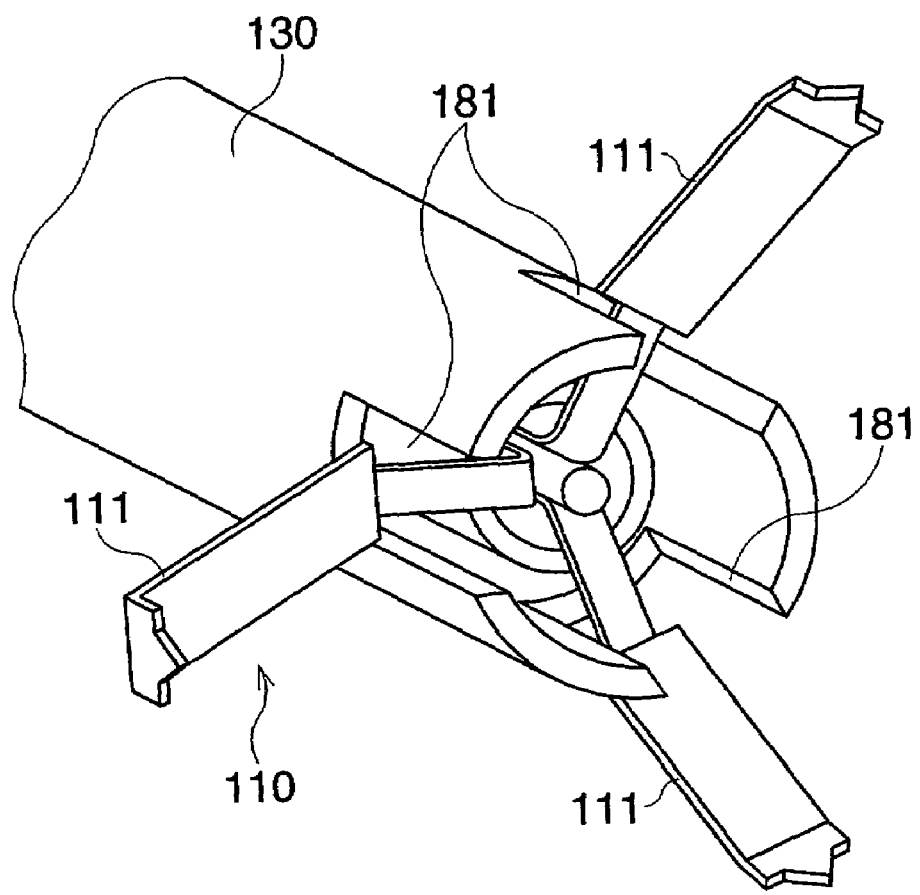
FIG. 72 is a perspective view showing the distal end of the clip device of the twenty-first embodiment.

FIGS. 71 and 72 show a twenty-second embodiment, in which the number of arms 111 is three, and the notches 181 are formed in three portions at the distal end of the outer sheath 130. Further, the operating wire 131 and the clip 110 are connected by the clip connecting string 115. The other constructions are the same as those of the twenty-first embodiment.

In the first through twenty-second embodiments, the number of the arms 111 is not restricted to two or three as shown in the corresponding drawings, but can be changed.

Further, in the fifth, sixth, eleventh through twenty-second embodiments, when the number of the arms 111 is two, the clip may be obtained by bending a metal plate strip, such as a stainless steel strip, in an α-shape.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application Nos. 2001-153658, 2001-

154804, 2001-177831, 2001-184360, 2001-247927, 2001-249834, 2001-343985, 2001-346965, 2001-349642, and 2001-353218 (filed on May 23, May 24, Jun. 13, Jun. 19, Aug. 17, Aug. 21, Nov. 9, Nov. 13, Nov. 15, and Nov. 19, 2001, respectively), which are expressly incorporated herein, by reference, in their entireties.

What is claimed is:

1. A clip device of an endoscope, comprising:
a clip that is provided with at least three arms and a base end portion to which said arms are connected, each of said arms having an open-close deforming portion located close to said base end portion, said clip being inserted in a sheath, in a state in which said arms are closed, and positioned at a distal end of said sheath;
a core member that is provided inside said clip to be in contact with an inner surface of said open-close deforming portion at least when said arms are open; and
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other.

2. A clip device according to claim 1, wherein said open-close deforming portion has a constriction and a bulge portion formed between said constriction and said base end portion.

3. A clip device according to claim 2, wherein said core member has a small diameter portion positioned inside said constriction and a large diameter portion positioned closer to said base end portion in comparison with said small diameter portion.

4. A clip device according to claim 1, further comprising an operating wire provided in said sheath to move along the axis of said sheath, a string connecting said operating wire and said clip, and a cutting mechanism that is provided close to said clip, said clip being engaged with said open-close member to open and close when said operating wire is pulled from the base end of said sheath, said string being cut said cutting mechanism when said operating wire is further pulled from the base end.

5. A clip device according to claim 4, wherein said cutting mechanism is provided to said core member.

6. A clip device according to claim 4, wherein said cutting mechanism is provided to said clip at a position between said base end portion and said arms.

7. A clip device according to claim 1, further comprising a reducer of frictional resistance occurring between said core member and said clip, and/or between said clip and said open-close member, when said clip opens and closes.

8. A clip device according to claim 7, wherein said reducer of frictional resistance comprises a recess formed on said core member so as to reduce interference between said clip and said core member when said clip opens and closes.

9. A clip device according to claim 7, wherein said reducer of frictional resistance comprises a thin portion of said clip, of which the thickness is less than the other portions of said clip, said thin portion being in contact with one of said core member and said open-close member when said clip opens and closes.

10. A clip device according to claim 1, wherein said clip is obtained by bending a single plate member without crossing at any portion in such a manner that a boundary portion, between said base end portion and said arms, is formed into a constricted shape.

11. A clip device according to claim 10, wherein said plate member is bent at said boundary portion in such a manner that said plate member is projected toward the inside of said boundary portion.

12. A clip device according to claim 10, wherein said plate member has peak portions which are projected toward the inside of said boundary portion and are in contact with each other.

13. A clip device according to claim 10, wherein said clip has a substantially uniform breadth as a whole.

14. A clip device according to claim 1, wherein each of said arms has a claw portion, which is formed at a tip portion of the arm and bent inward with an acute angle.

15. A clip device according to claim 14, wherein said acute angle is between 30 degrees and 60 degrees.

16. A clip device according to claim 1, wherein said open-close member is engaged with said base end portion, which is provided with a stopper for preventing said open-close member from disengaging from said clip.

17. A clip device according to claim 16, wherein said stopper is a flat spring extending from said base end portion.

18. A clip device according to claim 1, wherein said open-close member is a flexible cylindrical body.

19. A clip device according to claim 18, wherein said open-close member is a coil pipe, which is formed of a metal wire coiled with a constant diameter.

20. A clip device according to claim 18, wherein said open-close member is formed of rubber material having elasticity.

21. A clip device according to claim 1, further comprising a clip connecting hook detachably connected to said base end portion of said clip, said clip connecting hook and said open-close member being temporarily connected to each other by a temporal-fixing agent, which is filled in said open-close member, so that said clip is inserted in said sheath, a water supply passage, the outlet of which is said distal end of said sheath, being formed in said sheath in such a manner that said water supply passage does not interfere with said temporal-fixing agent.

22. A clip device according to claim 21, wherein said water supply passage is formed to pass outside said open-close member.

23. A clip device according to claim 21, wherein said open-close member is formed with a passage in which said temporal-fixing agent is not filled, said passage functioning as said water supply passage.

24. A clip device according to claim 1, wherein a clip unit, containing said clip and said open-close member, inserted in said sheath when in use, is housed in a preserve member.

25. A clip device according to claim 24, wherein said clip unit housed in said preserve member is enclosed in a sterile pack, which can be opened.

26. A clip device according to claim 24, wherein said preserve member is a cylindrical member.

27. A clip device according to claim 26, wherein said preserve member is movable relative to said clip unit along the axial direction of said preserve member.

28. A clip device according to claim 26, wherein said clip unit further comprises a string provided for engaging with a hook member provided in said sheath, said preserve members having a slit, said string extending outside said preserve member, being sandwiched by said slit.

29. A clip device according to claim 1, further comprising a cover tube having a clip engaging portion at a distal end thereof, with which said clip can be engaged, said cover tube covering said sheath and being rotatable about the axis of said cover tube, said cover tube being rotated by a rotating operation performed from the base end of said sheath, so that an angular position of said clip about the axis can be controlled to any arbitrary angle.

30. A clip device according to claim 29, wherein said clip engaging portion comprises a notch opening to said distal end of said sheath, so that said arms can be closed.

31. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath, wherein each of said arms has at least one peak portion which is projected toward the inside of said boundary portion and is in contact with a peak portion of the other arm and
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other.

32. A clip device according to claim 31, wherein said plate member is bent at said boundary portion in such a manner that said plate member is projected toward the inside of said boundary portion.

33. A clip device according to claim 31, wherein said clip has a substantially uniform breadth as a whole.

34. A clip device according to claim 31, wherein each of said arms has a claw portion, which is formed at a tip portion of the arm and bent inward with an acute angle.

35. A clip device according to claim 34, wherein said acute angle is between 30 degrees and 60 degrees.

36. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath;
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other; and
a core member that is provided inside said clip to be in contact with an inner surface of said open-close deforming portion at least when said arms are open.

37. A clip device according to claim 36, wherein said core member has a small diameter portion positioned inside said constriction and a large diameter portion positioned closer to said base end portion in comparison with said small diameter portion.

38. A clip device according to claim 35, wherein said cutting mechanism is provided to said core member.

39. A clip device according to claim 36, further comprising a reducer of frictional resistance occurring between said core member and said clip, and/or between said clip and said open-close member, when said clip opens and closes.

40. A clip device according to claim 39, wherein said reducer of frictional resistance comprises a recess formed on said core member so as to reduce interference between said clip and said core member when said clip opens and closes.

41. A clip device according to claim 39, wherein said reducer of frictional resistance comprises a thin portion of said clip, in which the thickness is less than the other portion of said clip, said thin portion being in contact with said core member when said clip opens and closes.

42. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath;
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other; and
an operating wire provided in said sheath to move to and fro along the longitudinal axis of said sheath, a string connecting said operating wire and said clip, and a cutting mechanism that is provided close to said clip, said clip being engaged with said open-close member to open and close when said operating wire is pulled from the base end of said sheath, said string being cut by said cutting mechanism when said operating wire is further pulled from the base end.

43. A clip device according to claim 42, wherein said cutting mechanism is provided to said clip at a position between said base end portion and said arms.

44. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath; and
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other,
wherein said open-close member is engaged with said base end portion, which is provided with a stopper for preventing said clip from dropping off from said open-close member.

45. A clip device according to claim 44, wherein said stopper is a flat spring extending from said base end portion.

46. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath; and
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other,
wherein said open-close member is a flexible cylindrical body.

47. A clip device according to claim 46, wherein said open-close member is a coil pipe, which is formed of a metal wire coiled with a constant diameter.

48. A clip device according to claim 46, wherein said open-close member is formed of rubber material having elasticity.

49. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath;
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other; and
a clip connecting hook detachably connected to said base end portion of said clip, said clip connecting hook and said open-close member being temporarily connected to each other by a temporal-fixing agent, which is filled in said open-close member, so that said clip is inserted in said sheath, a water supply passage, the outlet of which is said distal end of said sheath, being formed in said sheath in such a manner that said water supply passage does not interfere with said temporal-fixing agent.

50. A clip device according to claim 49, wherein said water supply passage is formed to pass outside said open-close member.

51. A clip device according to claim 49, wherein said open-close member is formed with a passage in which said temporal-fixing agent is not filled, said passage functioning as said water supply passage.

52. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath; and
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other,
wherein a clip unit, containing said clip and said open-close member, inserted in said sheath when in use, is housed in a preserve member.

53. A clip device according to claim 52, wherein said clip unit housed in said preserve member is enclosed in a sterile pack, which can be opened.

54. A clip device according to claim 52, wherein said preserve member is a cylindrical member.

55. A clip device according to claim 54, wherein said preserve member is movable relative to said clip unit along the axial direction of said preserve member.

56. A clip device according to claim 54, wherein said clip unit further comprising a string provided for engaging with a member provided in said sheath, said preserve member having a slit, said string extending outside said preserve member and being sandwiched by said slit.

57. A clip device of an endoscope, comprising:
a clip that is provided with a pair of arms and a base end portion to which said arms are connected, each of said arms having an open-close deforming portion located close to said base end portion, said clip being obtained by bending a single plate member without crossing at any portion in such a manner that a boundary portion, between said base end portion and said arms, is formed into a constriction, said clip being inserted in a sheath, in a state in which said arms are closed, and positioned at a distal end of said sheath;
an open-close member that is operated by remote control performed from the base end of said sheath, which is opposite to said distal end, said open-close member being engaged with said open-close deforming portion to open and close said arms with a substantially equivalent angular interval and so as to prevent each of said arms from crossing each other; and
a cover tube having a clip engaging portion at a distal end thereof, with which said clip can be engaged, said cover tube covering said sheath and being rotatable about the axis of said cover tube, said cover tube being rotated by a rotating operation performed from the base end of said sheath, so that an angular position of said clip about the axis can be controlled to an arbitrary angle.

58. A clip device according to claim 57, wherein said clip engaging portion comprises a notch opening to said distal end of said sheath so that said arms can be closed.

* * * * *